(12) United States Patent
Gonzales et al.

(10) Patent No.: US 9,474,915 B2
(45) Date of Patent: Oct. 25, 2016

(54) SYSTEMS, DEVICES AND METHODS FOR PROVIDING THERAPY TO AN ANATOMICAL STRUCTURE USING HIGH FREQUENCY PRESSURE WAVES AND/OR CRYOGENIC TEMPERATURES

(75) Inventors: Donald A. Gonzales, San Antonio, TX (US); Fred B. Dinger, III, San Antonio, TX (US); Prasad Nalluri, Boerne, TX (US)

(73) Assignee: Entrigue Surgical, Inc., Austin, TX (US)

(*) Notice: Subject to any disclaimer, the term of this patent is extended or adjusted under 35 U.S.C. 154(b) by 440 days.

(21) Appl. No.: 13/242,291

(22) Filed: Sep. 23, 2011

(65) Prior Publication Data

US 2012/0078377 A1     Mar. 29, 2012

Related U.S. Application Data

(60) Provisional application No. 61/386,336, filed on Sep. 24, 2010, provisional application No. 61/387,314, filed on Sep. 28, 2010.

(51) Int. Cl.
| | |
|---|---|
| A61F 2/04 | (2013.01) |
| A61B 18/02 | (2006.01) |
| A61N 7/00 | (2006.01) |
| A61M 29/02 | (2006.01) |
| A61B 18/14 | (2006.01) |
| A61B 18/00 | (2006.01) |
| A61M 31/00 | (2006.01) |

(52) U.S. Cl.
CPC ............... *A61N 7/00* (2013.01); *A61B 18/02* (2013.01); *A61M 29/02* (2013.01); *A61B 18/1492* (2013.01); *A61B 34/20* (2016.02); *A61B 2018/00327* (2013.01); *A61M 31/00* (2013.01); *A61M 2210/0681* (2013.01); *A61N 2007/0043* (2013.01)

(58) Field of Classification Search
CPC ......... A61F 2/06; A61F 2/04; A61N 1/3601; A61N 1/28; A61B 18/02
USPC ........... 623/1.2, 1.42–1.43, 10, 23.64–23.71; 604/20–22; 606/191–204.45
See application file for complete search history.

(56) References Cited

U.S. PATENT DOCUMENTS

| | | | |
|---|---|---|---|
| 2,525,183 A | 10/1950 | Robison | 606/196 |
| 4,733,665 A | 3/1988 | Palmaz | 606/108 |
| 4,740,207 A | 4/1988 | Kreamer | 623/1.15 |
| 4,877,030 A | 10/1989 | Beck et al. | 606/195 |
| 4,954,126 A | 9/1990 | Wallsten | 600/36 |

(Continued)

FOREIGN PATENT DOCUMENTS

| | | | |
|---|---|---|---|
| AU | 2010256450 | 1/2015 | A61F 2/04 |

OTHER PUBLICATIONS

Office Communication issued in Australian Patent Application No. 2011305256, issued Sep. 20, 2013.

(Continued)

*Primary Examiner* — Yashita Sharma
(74) *Attorney, Agent, or Firm* — David Warmbold

(57) ABSTRACT

A system, device and method for dilating an anatomical structure. Systems, devices and methods may comprise a therapeutic component configured to treat a paranasal sinus. Specific embodiments may use high frequency pressure waves and/or cryogenic temperatures.

14 Claims, 64 Drawing Sheets

(56) References Cited

U.S. PATENT DOCUMENTS

| | | | |
|---|---|---|---|
| 5,007,926 A | 4/1991 | Derbyshire | 623/1.15 |
| 5,059,211 A | 10/1991 | Stack et al. | 623/1.15 |
| 5,192,307 A | 3/1993 | Wall | 623/1.2 |
| 5,421,955 A | 6/1995 | Lau et al. | 216/48 |
| 5,441,515 A | 8/1995 | Khosravi et al. | 606/194 |
| 5,443,500 A | 8/1995 | Sigwart | 623/1.17 |
| 5,540,240 A | 7/1996 | Bauer | 128/898 |
| 5,549,662 A | 8/1996 | Fordenbacher | 623/1.17 |
| 5,593,416 A | 1/1997 | Donahue | 606/170 |
| 5,601,583 A | 2/1997 | Donahue et al. | 606/170 |
| 5,618,299 A | 4/1997 | Khosravi et al. | 623/1.2 |
| 5,643,304 A | 7/1997 | Schechter et al. | 606/171 |
| 5,643,314 A | 7/1997 | Carpenter et al. | 623/1.2 |
| 5,649,977 A | 7/1997 | Campbell | 623/1.15 |
| 5,733,328 A | 3/1998 | Fordenbacher | 623/1.16 |
| 5,735,872 A | 4/1998 | Carpenter et al. | 623/1.16 |
| 5,833,692 A | 11/1998 | Cesarini et al. | 606/79 |
| 5,921,956 A | 7/1999 | Grinberg et al. | 604/95 |
| 5,938,101 A | 8/1999 | Izuchukwu et al. | 227/176.1 |
| 6,342,061 B1 | 1/2002 | Kauker et al. | 606/180 |
| 6,464,711 B1 | 10/2002 | Emans et al. | 606/167 |
| 7,462,175 B2 | 12/2008 | Chang et al. | 604/510 |
| 7,500,971 B2 | 3/2009 | Chang et al. | 604/510 |
| 7,553,275 B2 | 6/2009 | Padget et al. | 600/142 |
| 7,670,284 B2 | 3/2010 | Padget et al. | 600/142 |
| 7,674,263 B2 | 3/2010 | Ryan | 606/50 |
| 2001/0051784 A1* | 12/2001 | Brisken et al. | 604/22 |
| 2002/0022861 A1 | 2/2002 | Jacobs et al. | 606/216 |
| 2003/0045902 A1 | 3/2003 | Weadock | 606/219 |
| 2004/0064150 A1 | 4/2004 | Becker | 606/196 |
| 2004/0186468 A1 | 9/2004 | Edwards | 606/41 |
| 2006/0004323 A1 | 1/2006 | Chang et al. | 604/28 |
| 2006/0136041 A1 | 6/2006 | Schmid et al. | 623/1.16 |
| 2006/0149310 A1 | 7/2006 | Becker | 606/196 |
| 2007/0073269 A1 | 3/2007 | Becker | 604/509 |
| 2008/0021369 A1* | 1/2008 | Deem et al. | 604/20 |
| 2008/0097154 A1 | 4/2008 | Makower et al. | 600/114 |
| 2008/0097467 A1 | 4/2008 | Gruber et al. | 606/119 |
| 2008/0132938 A1 | 6/2008 | Chang et al. | 606/196 |
| 2008/0172033 A1 | 7/2008 | Keith et al. | 604/506 |
| 2008/0188879 A1 | 8/2008 | Vakharia et al. | 606/47 |
| 2008/0208242 A1 | 8/2008 | Becker | 606/196 |
| 2008/0208243 A1 | 8/2008 | Becker | 606/199 |
| 2008/0215082 A1 | 9/2008 | Becker | 606/196 |
| 2008/0215083 A1 | 9/2008 | Becker | 606/196 |
| 2009/0125046 A1 | 5/2009 | Becker | 606/167 |
| 2009/0163890 A1 | 6/2009 | Clifford et al. | 604/514 |
| 2009/0312745 A1 | 12/2009 | Goldfarb et al. | 604/514 |
| 2010/0030113 A1 | 2/2010 | Morriss et al. | 600/585 |
| 2010/0312101 A1 | 12/2010 | Drontle et al. | 600/424 |
| 2010/0312338 A1 | 12/2010 | Gonzales et al. | 623/10 |
| 2011/0022172 A1 | 1/2011 | Gonzales et al. | 623/10 |
| 2015/0157313 A1 | 6/2015 | Gonzales et al. | 606/151 |

OTHER PUBLICATIONS

Balcon et al., "Recommendations on Stent Manufacture, Implantation and Utilization," European Heart Journal (1997), vol. 18, pp. 1536-1547.

Göttmann, D., Strohm, M., Strecker, E. P., Karlsruhe, D. E., "Balloon dilatation of Recurrent Ostial Oclusion of the Frontal Sinus", Abstract No. B-0453, European Congress of Radiology (2001).

"The Stenter's Notebook," Physician's Press (1998), Birmingham, Mich.

Strohm, M., Göttmann, D., "Treatment of Stenoses of Upper Air Routes by Balloon Dilatation", Proceeding of the 83rd Annual Convention of the Association of West German ENT Physicians (1999).

PCT International Preliminary Report on Patentability for PCT/US2012/053420 7pgs, Mar. 20, 2014.

* cited by examiner

Coronal View

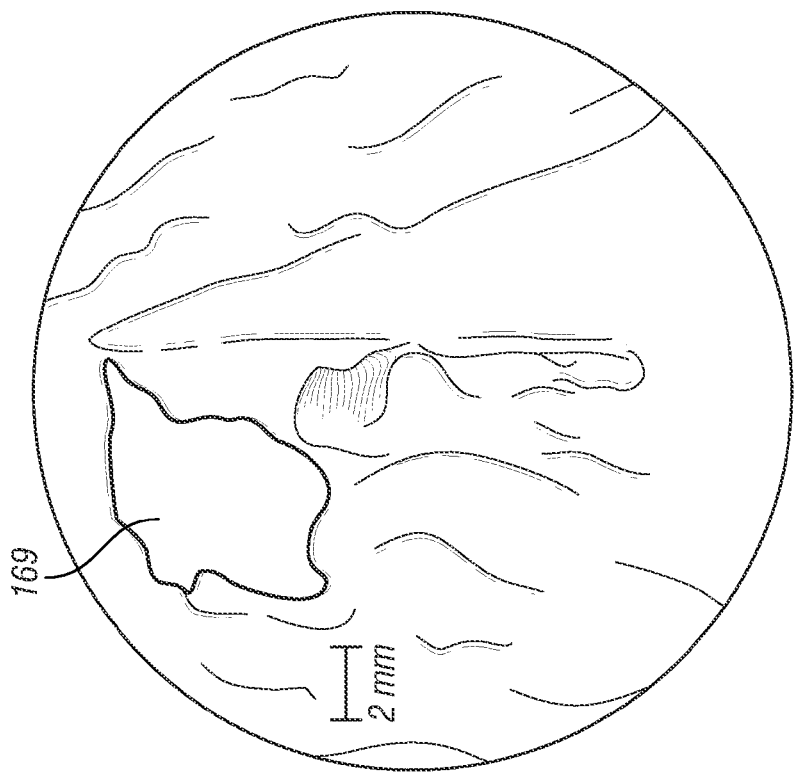
FIG. 2K  Sinus Ostia After Dilation
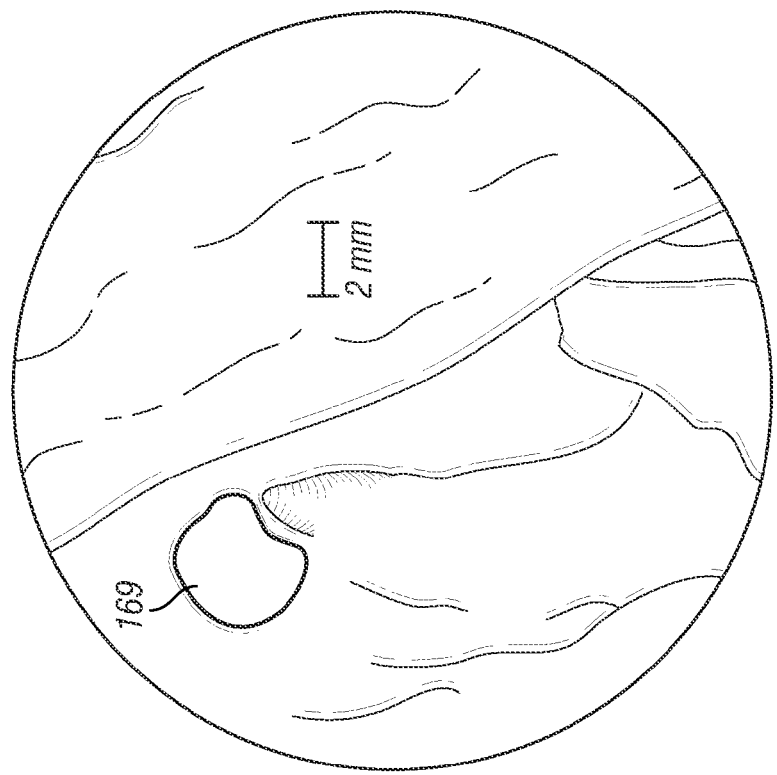
FIG. 2J  Sinus Ostia Before Dilation

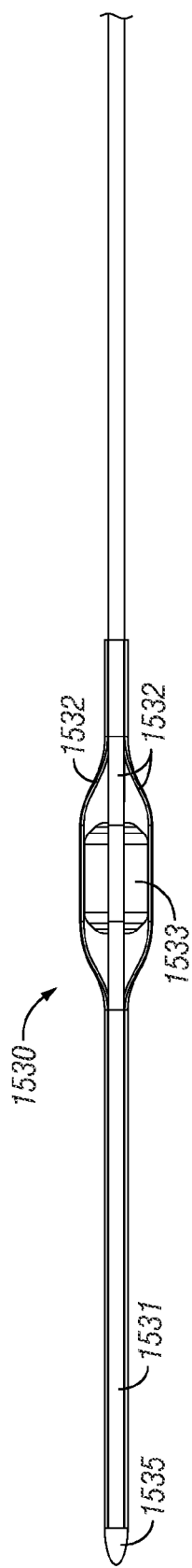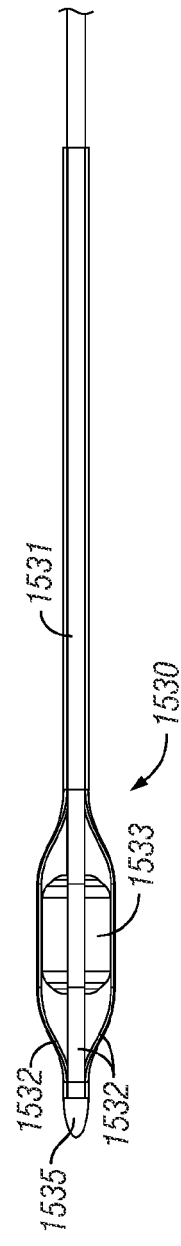
FIG. 4C
FIG. 4D

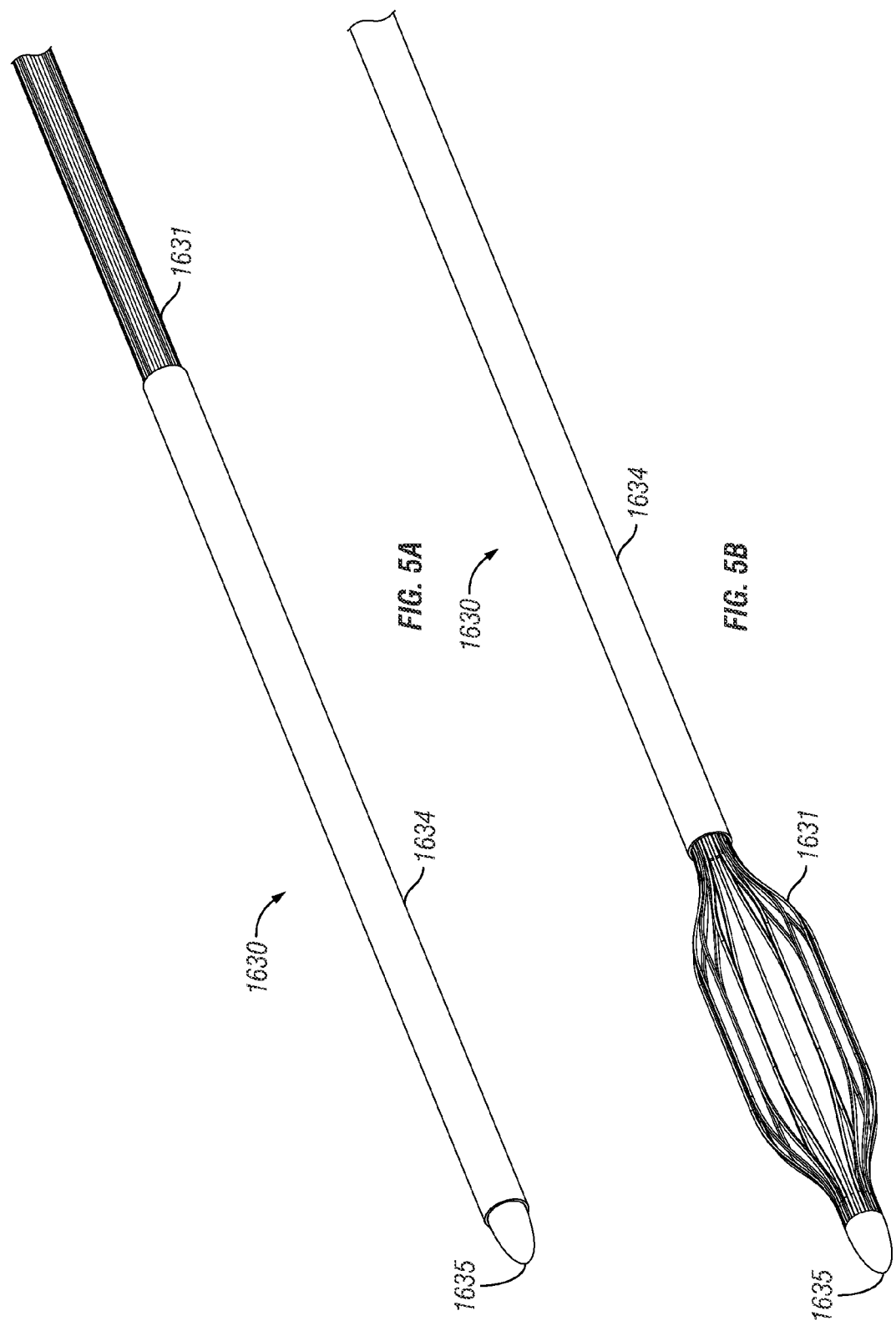

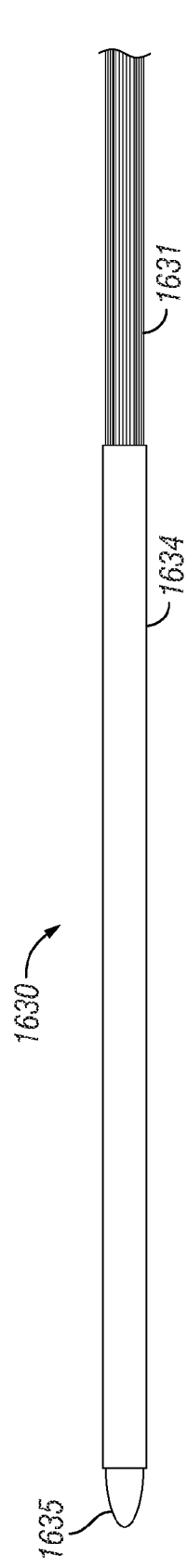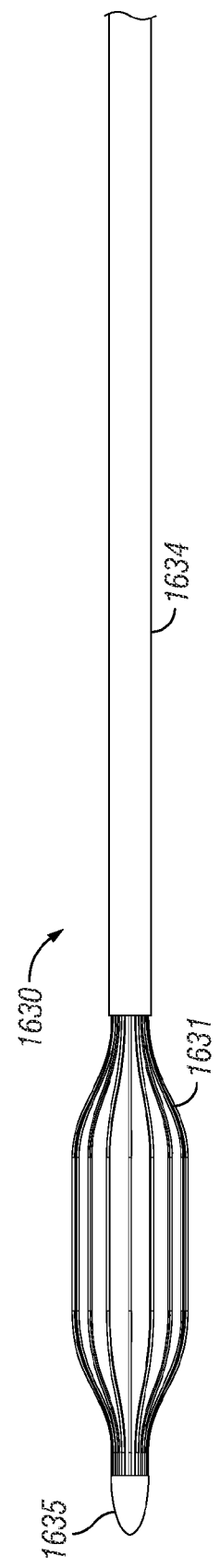

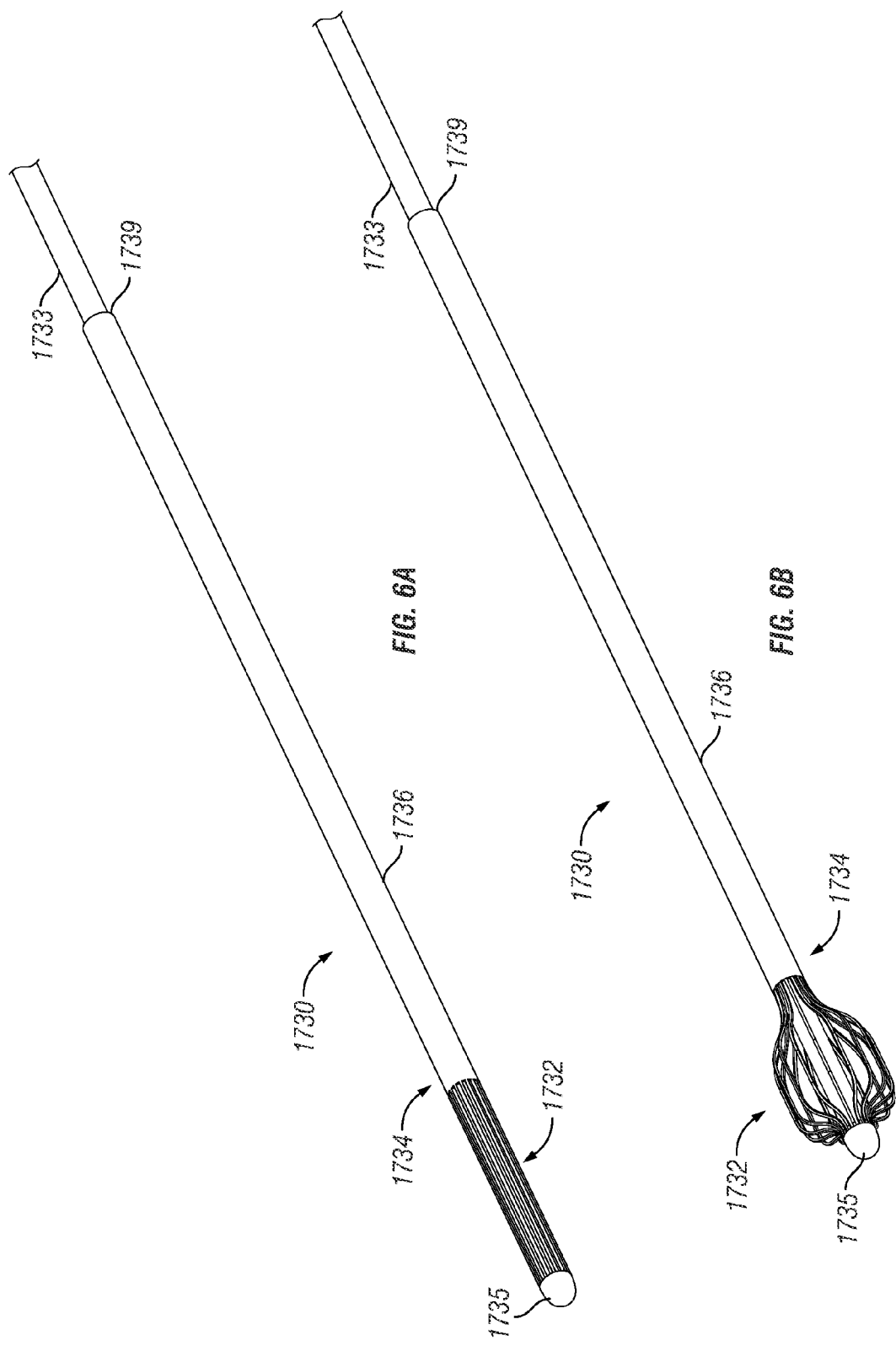

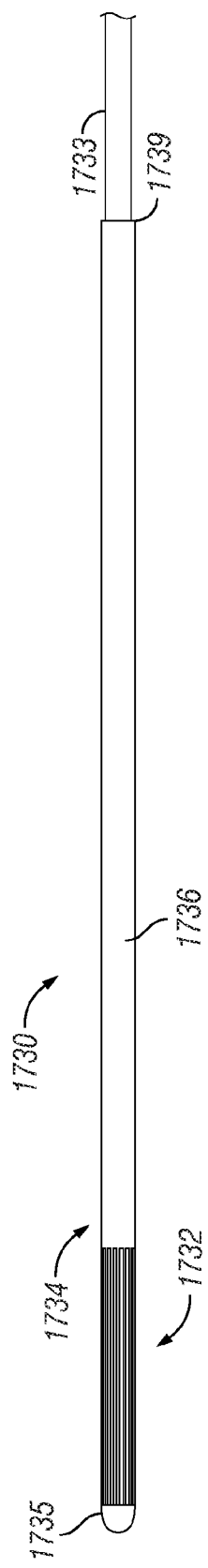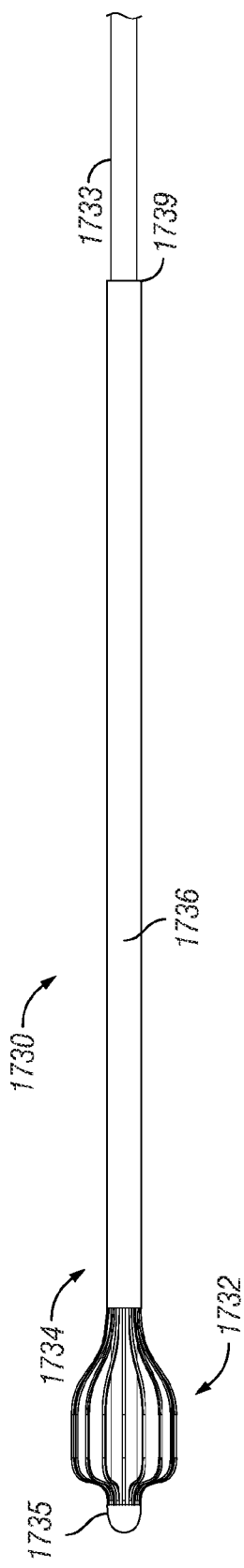
FIG. 6C
FIG. 6D

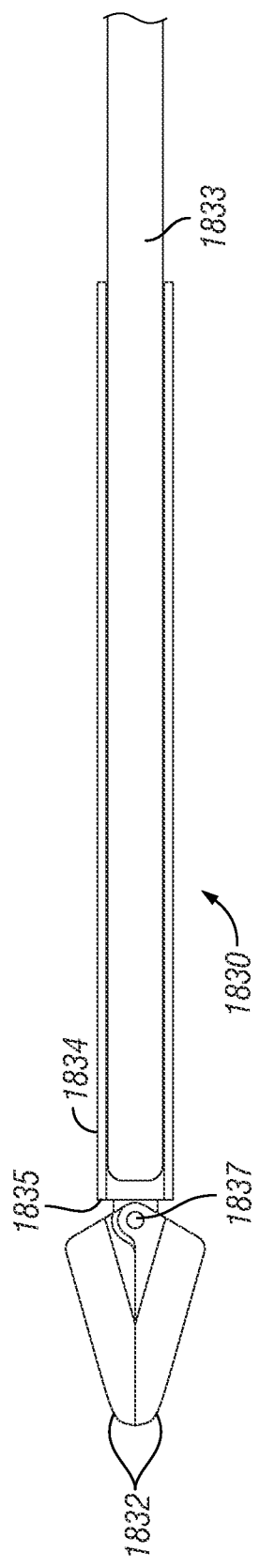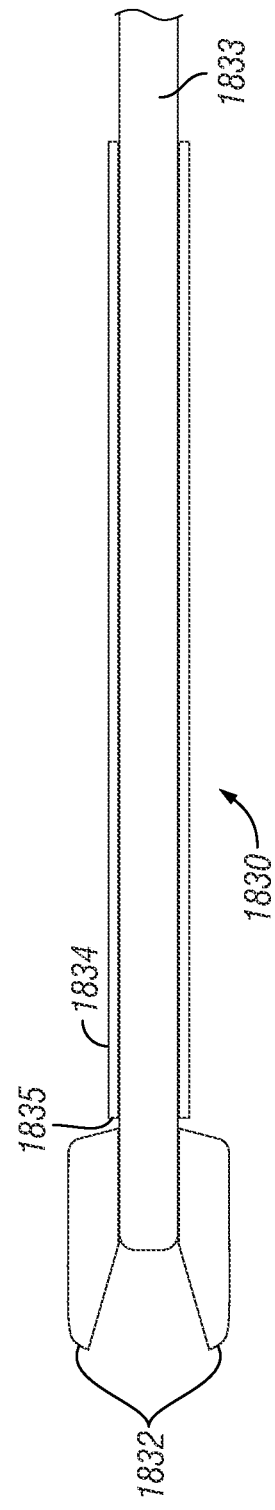

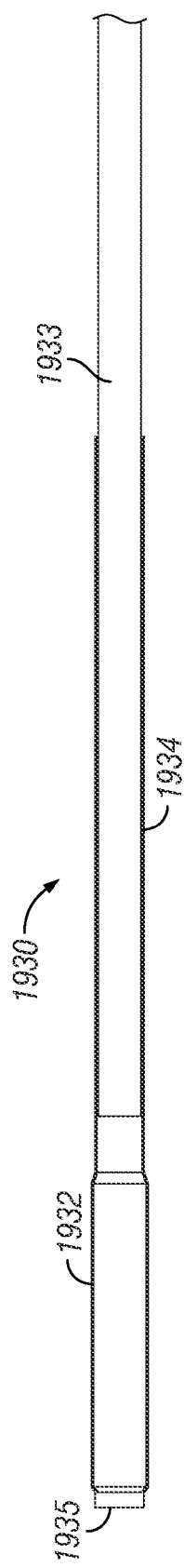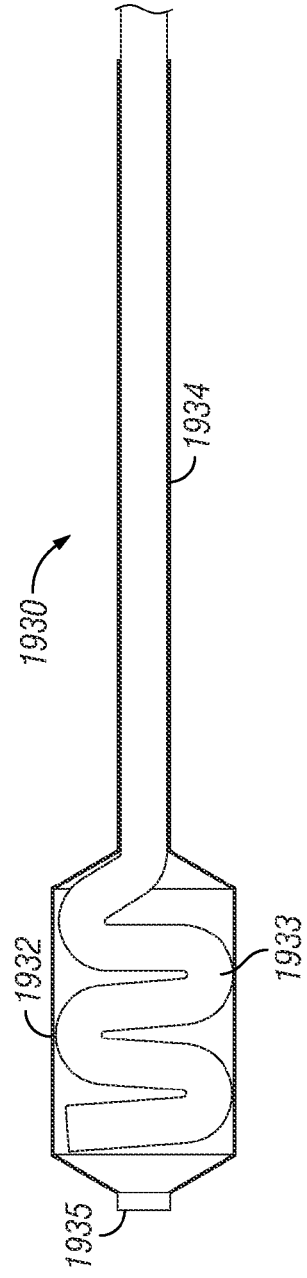
FIG. 8A
FIG. 8B

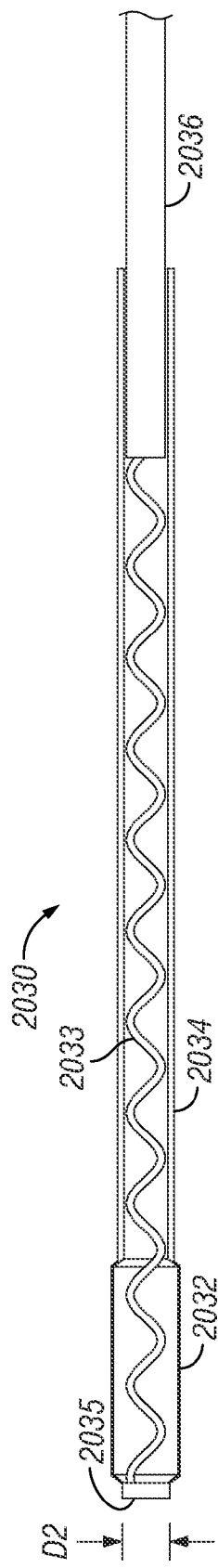
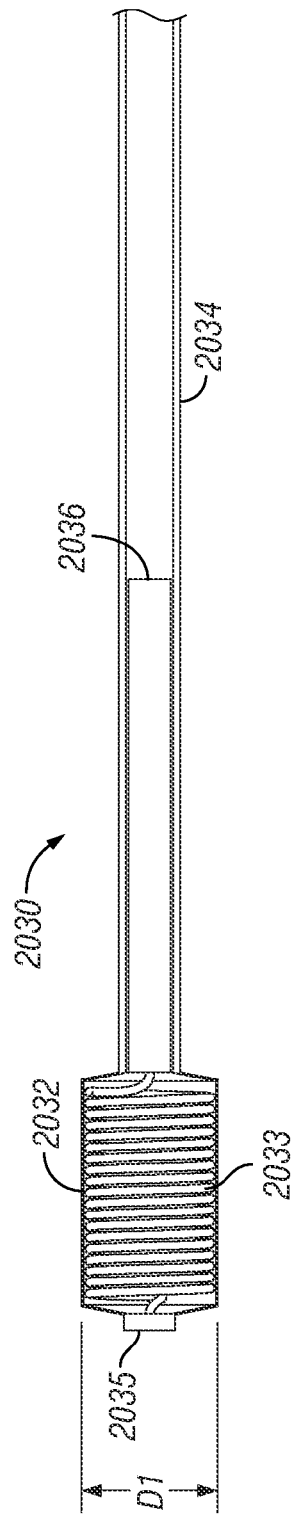
FIG. 9A
FIG. 9B

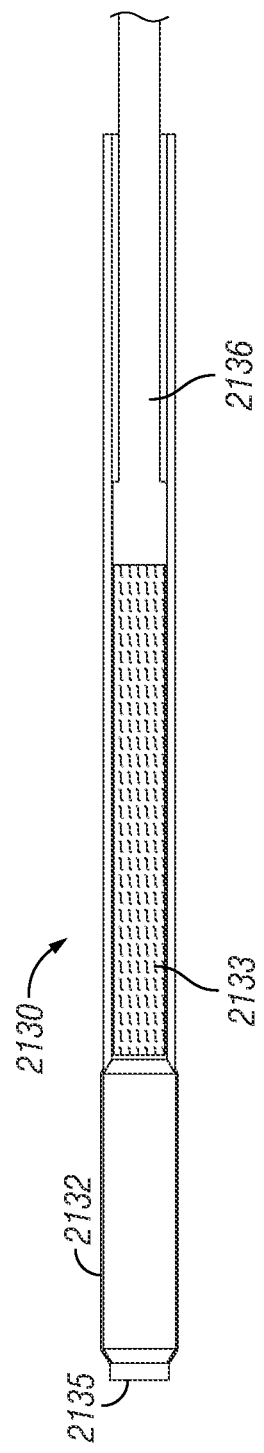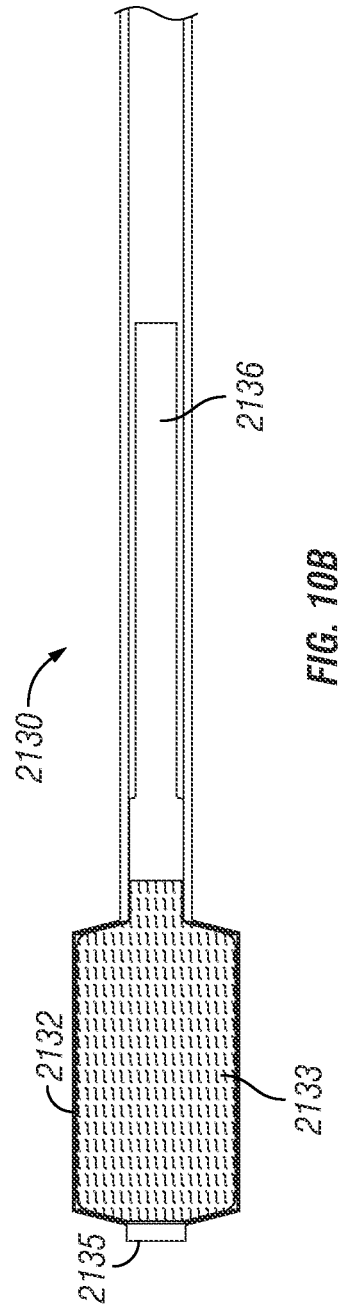

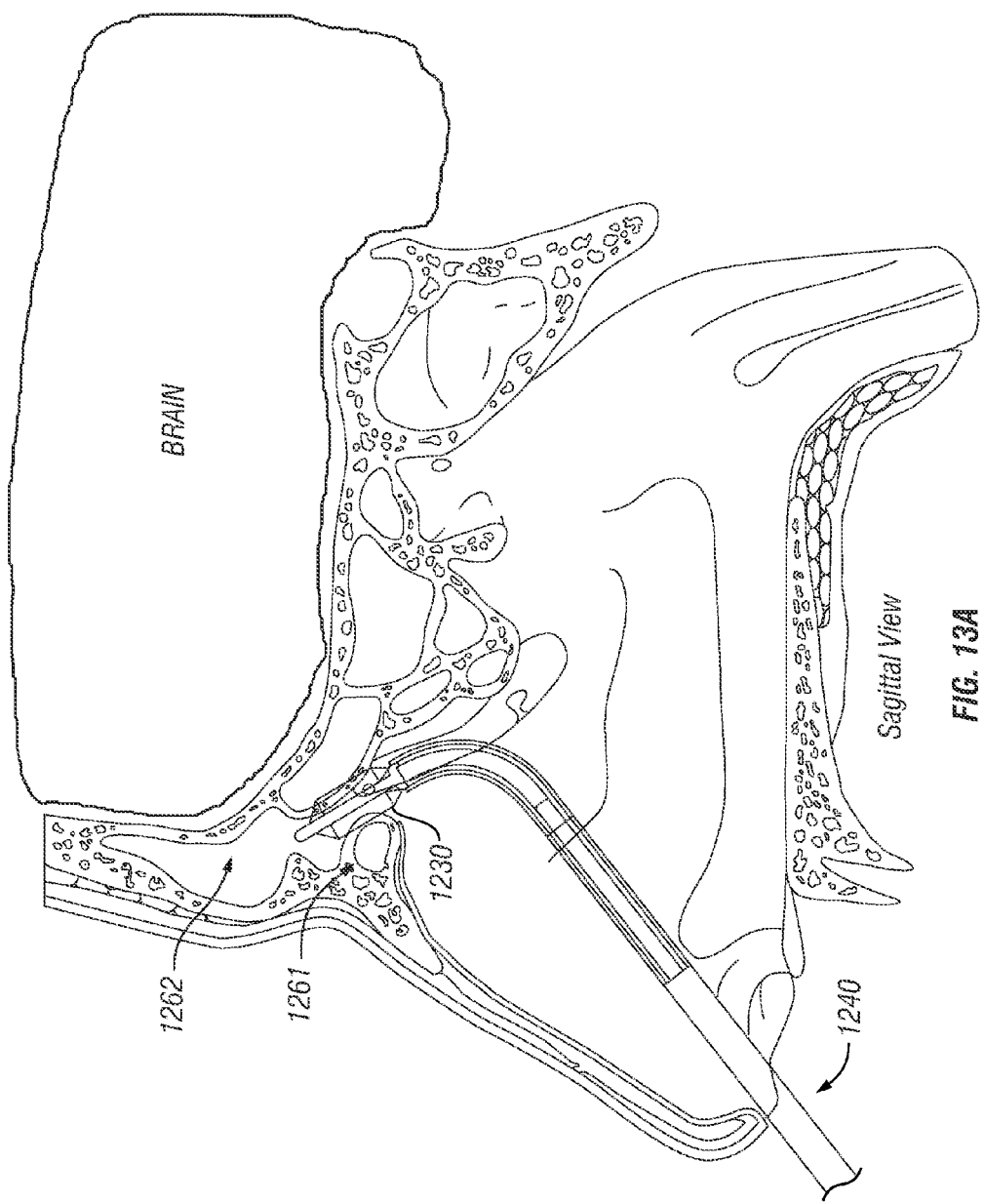

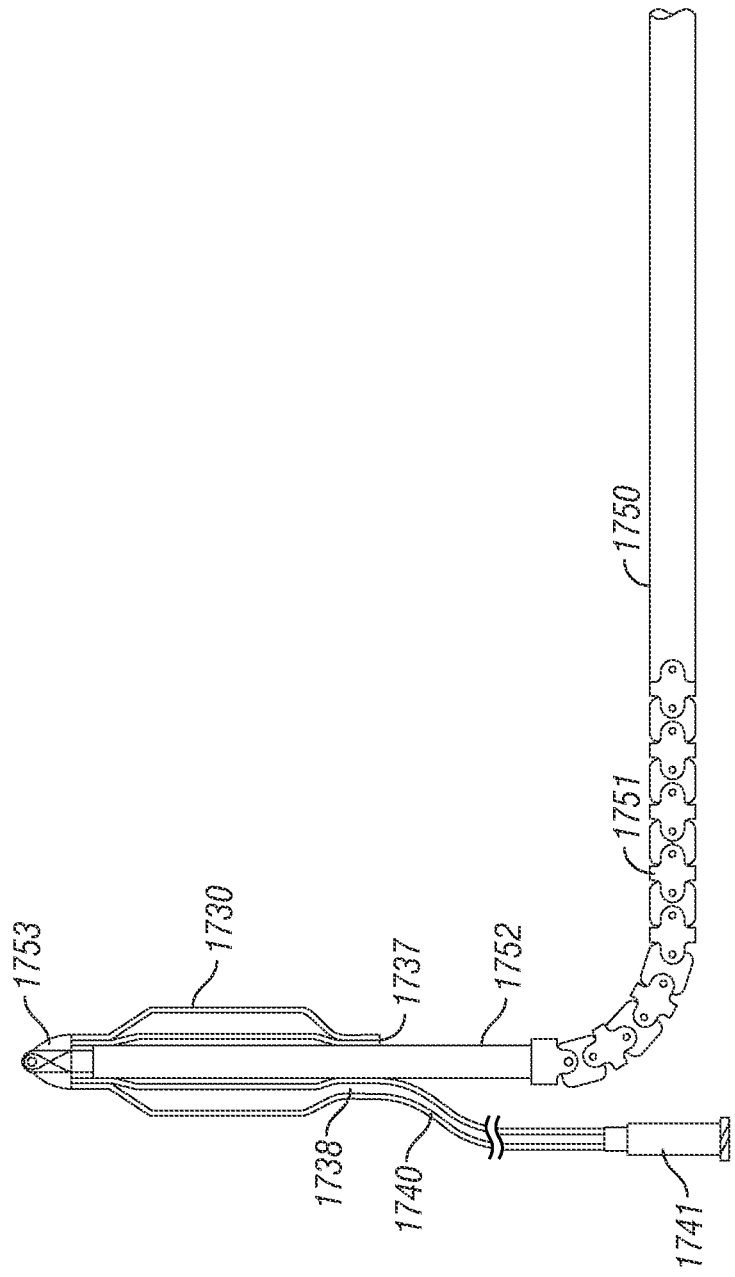

SYSTEMS, DEVICES AND METHODS FOR PROVIDING THERAPY TO AN ANATOMICAL STRUCTURE USING HIGH FREQUENCY PRESSURE WAVES AND/OR CRYOGENIC TEMPERATURES

CROSS-REFERENCE TO RELATED APPLICATIONS

This application claims priority to U.S. Provisional Patent Application Ser. Nos. 61/386,336 (filed Sep. 24, 2010) and 61/387,314 (filed Sep. 28, 2010), the contents of which are incorporated herein by reference.

This application incorporates by reference the following applications: U.S. Provisional Patent Application Ser. Nos. 61/184,614 (filed Jun. 5, 2009); 61/231,086 (filed Aug. 4, 2009); 61/289,480 (filed Dec. 23, 2009); and U.S. patent application Ser. No. 12/794,321 (filed Jun. 4, 2010).

BACKGROUND OF THE INVENTION

Surgical treatments for ear, nose and throat (ENT) disorders (e.g. sinusitus) have evolved slowly. In current clinical practice, functional endoscopic sinus surgery (FESS) is used to treat disorders where mucous drainage is impaired and/or chronic infections are present. In FESS, an endoscope is inserted into the nose and, under visualization through the endoscope, the surgeon may remove diseased or hypertrophic soft tissue or bone and may enlarge the ostia of the sinuses to restore normal drainage of the sinuses. FESS procedures can be effective in the treatment of sinusitis and for the removal of tumors, polyps and other aberrant growths from the nose. Other endoscopic intranasal procedures have been used to remove pituitary tumors, to treat Graves disease (i.e., a complication of hyperthyroidism which results in protrusion of the eyes) and to bring about surgical repair of rare conditions, such as cerebrospinal fluid rhinorrhea where cerebrospinal fluid leaks into the nose.

In certain instances, sinus and ENT surgery has been performed with the assistance of electronic navigation devices (i.e., "image-guided FESS"). In typical image guided surgical procedures, integrated anatomical information is supplied through CT-scan images or other anatomical mapping data taken before the operation. Data from a preoperative CT scan or other anatomical mapping procedure is downloaded into a computer and special sensors known as localizers or location sensors are attached to the surgical instruments. Thus, using the computer, the surgeon can ascertain, in three dimensions, the precise position of each location sensor-equipped surgical instrument at any given point in time. This information, coupled with the visual observations made through the standard endoscope, can help the surgeon to carefully position the surgical instruments to avoid creating CSF leaks and to avoid causing damage to nerves or other critical structures.

Although FESS is an accepted therapy for severe sinuses, it has several shortfalls. Often patients complain of the post-operative pain and bleeding associated with the procedure. A significant subset of patients remain symptomatic even after multiple surgeries. Since FESS is considered an option only for the most severe cases (those showing abnormalities under CT scan), a large population of patients exist that either cannot tolerate the prescribed medications or are not considered candidates for surgery. Further, because the methodologies to assess sinus disease are primarily static measurements (e.g., CT, MRI), patients whose symptoms are episodic are often simply offered drug therapy when in fact underlying mechanical factors may play a significant role in their condition. To date, there is no mechanical therapy offered for these patients, and even though they may fail pharmaceutical therapies, no other course of action is indicated. This leaves a large population of patients in need of relief, unwilling or afraid to take steroids, but not sick enough to qualify for surgery.

The need for more minimally invasive treatments of diseased paranasal sinuses has resulted in the proposal of balloon dilation methods and devices. For example, U.S. Pat. No. 2,525,183 (Robison) discloses an inflatable pressure device which can be inserted within the sinus and inflated to restore the sinus passage to normal conditions. Lanza and others have used a Fogarty balloon to dilate nasal sinus passages to enlarge the openings and restore normal mucous drainage, as described by Orlandi et al (2001) and referenced by Lanza (2006).

U.S. Patent Publication No. 2004/0064150 A1 (Becker) and related applications disclose balloon catheters formed of a stiff hypotube to be pushed into a sinus. The balloon catheters have a stiff hypotube with a fixed pre-set angle that enables them to be pushed into the sinus. In at least some procedures wherein it is desired to position the balloon catheter in the ostium of a paranasal sinus, it is necessary to advance the balloon catheter through complicated or tortuous anatomy in order to properly position the balloon catheter within the desired sinus ostium. Also, there is a degree of individual variation in the intranasal and paranasal anatomy of human beings, thus making it difficult to design a stiff-shaft balloon catheter that is optimally shaped for use in all individuals. Indeed, rigid catheters formed of hypotubes that have pre-set angles cannot be easily adjusted by the physician to different shapes to account for individual variations in the anatomy. In view of this, the Becker patent application describes the necessity of having available a set of balloon catheters, each having a particular fixed angle so that the physician can select the appropriate catheter for the patient's anatomy. The requirement to test multiple disposable catheters for fit is likely to be very expensive and impractical. Moreover, if such catheter are disposable items (e.g., not sterilizable and reusable) the need to test and discard a number of catheters before finding one that has the ideal bend angle could be rather expensive. Furthermore, the rigidity of the catheters described by Becker may make access to certain acutely angled ostia difficult in the confined space of the nasal cavity. A further disadvantage of Becker is the inability to verify that the balloon position is in the correct location. In some anatomy where direct visualization is difficult to impossible, for example in the frontal recess, there is a risk of entering and dilating the wrong opening, which at best does not resolve the clinical symptoms and in some cases may lead to severe clinical complications.

Further, balloon dilation of the paranasal sinuses has been proposed using traditionally vascular devices and techniques. For example, European physicians have reported the use of a hydrophilic guidewire and standard PTCA balloon catheter to treat restenosis of surgically created openings in diseased frontal sinuses and stenotic nasal conae. Göttmann, D., Strohm, M., Strecker, E. P., Karlsruhe, D. E., Balloon dilatation of Recurrent Ostial Oclusion of the Frontal Sinus, Abstract No. B-0453, European Congress of Radiology (2001); Strohm, M., Göttmann, D., Treatment of Stenoses of Upper Air Routes by Balloon Dilation, Proceeding of the 83$^{rd}$ Annual Convention of the Association of West German ENT Physicians (1999).

A system of devices utilizing this approach is described in U.S. Pat. Nos. 7,462,175 and 7,500,971. This system includes a guidewire, and a guide catheter to position a balloon catheter into the target paranasal sinus. The balloon is then inflated to dilate the nasal opening. This system provides some advantages over the rigid system described by Becker. The guide wire allows access to sinuses around tortuous anatomy, with the guide catheter providing support for the floppy guide wire and balloon catheter. This system also includes two possible methods of position verification: fluoroscopy, or a guidewire with illumination.

Clinical experience with this system has demonstrated successful access and balloon dilation of sinus passages. However, several disadvantages remain with this approach. The addition of devices such as guide wires and guide catheters to navigate and position the balloon adds significant complexity and cost to the surgical case. As described, this added cost and complexity often prohibits these prior systems to be used in conjunction with standard sinus surgery equipment and techniques, but instead be used as a stand-alone procedure for isolated disease. This factor limits the clinical utility of this prior system, for example it does not allow the concurrent removal of the uncinate process or removal of the ethmoid air cells. In addition, the techniques employed to use these prior systems are not standard to the average ENT surgeon and require extensive training. Use of the fluoroscopy system alone requires extensive and expensive additions to operating room equipment, user training, and in some cases user certification. In addition, as with the Becker system, the guide catheters are shaped with a set angle, so that access to multiple sinuses in one patient may involve the use of several devices, increasing the cost of the procedure still further. Another disadvantage with the method used to place the balloon catheter, requiring the manipulation of a guide catheter and guide wire, is that this method requires at least two hands, and sometimes a third via an assistant, thus the concurrent use of an endoscope for direct visualization, as is standard for current sinus surgical procedures, would require an assistant: further cost and personnel in the operating room.

The structure of these devices also presents disadvantages. Because of the lack of rigidity of the guidewire and guide catheter, it is impossible to precisely locate the tips of these devices in 3-D space. While this is not an issue for vascular procedures where the working space is essentially linear, this is not true for the sinus cavities. Further, the lack of rigidity of the devices also lessens the ability to push the balloon across the tight spaces often encountered in chronic sinusitis patients, which may be obstructed by scar or granulation tissue. Finally, the lack of rigidity precludes the use of image guidance navigation systems for positioning and verifying the location of the balloon.

Recent publications have shown that the uncinate process, which shields the openings of the maxillary and frontal sinus and contribute to their ostia and outflow tracts, must be removed in order to allow the maximal drainage of these sinuses. Without removing the uncinate process and diseased tissue of the ethmoid air cells, the potential for surgical failure and need for revision dramatically increases. Additionally, maintenance of patency of the maxillary, frontal and sphenoid sinus can not be assured by purely balloon dilating the opening, and may require stenting the dilated sinus with an expandable stent to assure patency. The stent should preferably be absorbable to eliminate the risk and cost of removing the stent after healing has occurred.

Prior systems, based on cardiovascular technology, utilize the natural cannula created by the veins to assist in guiding the device. Such systems may use guide catheters and guide wires for delivery and positioning. In addition, these systems can require fluoroscopy and/or illumination devices for navigation and placement verification.

Prior devices, systems and methods have not been optimized for minimally invasive treatment of sinusitis, mucocysts, tumors, infections, hearing disorders, fractures, choanal atresia or other conditions of the paranasal sinuses, Eustachian tubes, Lachrymal ducts and other ear, nose, throat or mouth structures in which the atraumatic dilation and maintance of these structures is desirable. Non-articulating instruments are not capable of navigating the tortuous pathway to some of these structures. Guidewire and guide catheter access to these structures may not be possible without risk of trauma to the anatomy, or in some cases may not be possible at all. Systems are needed which can provide balloon dilation devices utilizing hand-held, articulating insertion devices that enable accurate and rapid access to these anatomic structures, and allow balloon dilation as an adjunct to surgical procedures on these structures. For example, balloon dilation of sinus ostia will allow removal of diseased tissue such as tumors or cysts without additional surgical modification. Balloons can also be used to treat orbital floor fractures by providing stability to the orbital floor via the maxillary ostia without the need for rigid fixation. In addition to dilation of the sinus ostia, balloons can be used to dilate other stenotic regions such as the nasal choana to relieve nasal obstruction due to stenosis, in the Eustachian tube to relieve Eustachian tube obstruction and in the lacrimal duct to relieve epiphora.

There exists a need for a balloon dilation system which can be delivered and positioned using surgical instrumentation and techniques currently employed by ENT surgeons, and which may be articulated by the user to aid in access and positioning in confined spaces, and to account for the variety of anatomy encountered during treatment of a single patient, as well as the variety of anatomy from patient to patient. There furthermore exists a need for a balloon delivery system which does not require the use of guide catheters and/or guide wires, with associated procedure time and cost, as well as pre-requisite training and equipment. In addition, there exists a need for a balloon dilation system which can be used in conjunction with image-guidance navigation systems, and which do not require the use of position verification methods and equipment not standard to the average ENT surgeon such as fluoroscopy or illumination. Additionally, there exists a need for a system which can deliver a stent to a dilated sinus. Some or all of these needs are met with the invention provided herein.

SUMMARY

In general, embodiments of the present invention provide methods, devices and systems for diagnosing and/or treating conditions relating to anatomical structures. Specific embodiments provide methods, devices and systems for dilating an anatomical structure such as a body lumen. The present disclosure focuses on embodiments suitable for ear, nose and throat (ENT) applications. A skilled surgeon, however, will recognize that embodiments within the scope of the present disclosure may be used for other anatomical structures or body lumens.

Specific embodiments relate to diagnosing and/or treating conditions affecting ENT passageways. Non-limiting examples of such disorders or conditions include sinusitis, mucocysts, tumors, infections, hearing disorders, fractures, choanal atresia or other conditions of the paranasal sinuses, Eustachian tubes, llachrymal ducts, ducts of salivary glands and other ear, nose, throat or mouth structures.

In accordance with embodiments of the present invention, there are provided devices and methods wherein one or more therapeutic components as described herein are inserted into the nose, nasopharynx, paranasal sinus, Eustachian tubes, middle ear, lachrymal ducts, ducts of salvary glands or other anatomical passageways or sinuses of the ear, nose, throat or mouth to perform an interventional or surgical procedure. In specific embodiments, the therapeutic component comprises a dilator such as an inflatable balloon. In a further embodiment, the therapeutic component may also comprise a channel or passageway for the delivery of therapeutic agents to the anatomic passageways or sinuses.

In an exemplary embodiment, the therapeutic component will interface with a rigid or articulating insertion device. Once interfaced, the device can be easily guided into a desired location using standard surgical techniques, and without the need of other means to guide the device such as guidewires or rigid guide tubes. The handle of the insertion device can include an actuator for controlling the articulation, which will enable the therapeutic component to be positioned and articulated with one hand, leaving the second hand free for holding an endoscope as is standard for FESS surgery. The instrument can also have means for locking the articulation mechanism into certain positions, such that the instrument is effectively rigid at predetermined angles, giving it the feel of standard ENT surgical instrument and providing the ability to accurately position the tip of the device in three-dimensional space. The insertion device can also have provisions and features to enable the intra-operative tracking of the instrument tip using currently available navigation systems. Once the device is in place, the desired therapeutic effect (e.g., dilation, stent placement, etc.) can occur.

In an embodiment, the therapeutic component is disposable, and the insertion device is reusable. In another embodiment, both the therapeutic component and insertion device are disposable. In yet another embodiment, the therapeutic component and insertion device are integrally attached. In addition, the therapeutic component may include a flexible, elongate sleeve which protects the linkages when used with an articulating instrument, as well as shield the articulating links from tissue and blood penetration.

In certain embodiments, the therapeutic component and insertion device include coupling means which allows the therapeutic component to be removably attached to the insertion device, thereby making the therapeutic component interchangeable between different insertion devices during a single procedure. For example, the user may use a single therapeutic component coupled with a variety of articulating and/or rigid instruments to treat all of the sinuses for a single patient. This feature reduces the number of different devices needed for a single procedure, bringing down the cost of the procedure. In an embodiment, the coupling means is attached to an actuator for locking and unlocking the therapeutic component on to the shaft.

Additional embodiments include features on the insertion device which provide the ability to flush and or suction the ostia, or delivery therapeutic agents, using the same insertion device that delivers the therapeutic component. In addition, embodiments and methods are provided which allow use of a flexible scope to aid in placement of the therapeutic component.

Additional devices and methods provide for innovative stenting of the ostia of the paranasal sinuses. In certain embodiments, the therapeutic component comprises a stent mounted onto an inflatable balloon. The stent can be positioned with the insertion device and deployed via inflation of the balloon. In specific embodiments, the stent may comprise an expandable, biodegradable or non-biodegradable stent. In particular embodiments, the stent could have the ability to be formed to the shape of the opening such as an hour glass for the sphenoid and maxillary sinus, or an inverted tapered cylinder for the frontal sinus. The shaping may occur for example via inflation of a shaped balloon, or via other shaping methods. The stent may alternately be self-expandable and not require a balloon to be deployed. In this embodiment, the stent is positioned in a restrained configuration, for example covered by a restraining sleeve, and then deployed once properly position via removal of the restraining sleeve. In certain embodiments, the stent could be removed after the desired time for healing or could biodegrade once healing has taken place. Exemplary embodiments may deploy stents disclosed in U.S. Patent Publication No. 2006/0136041 (published Jun. 22, 2006), entitled "Slide-and-Lock Stent," and incorporated by reference herein.

A particular embodiment comprises an insertion device configured for inserting a therapeutic component into an anatomical structure, including for example, a paranasal sinus outflow tract. In specific embodiments, the sinus outflow tract may comprise the frontal recess, maxillary and sphenoid ostia and/or the infundibulum. The infundibulum is the space between the maxillary sinus ostium and the uncinate process that contributes to the outflow tract of maxillary, anterior ethmoid and frontal sinuses. In certain embodiments, therapy may be provided for a condition, e.g. sinusitis, by expanding or dilating the infundibulum with a therapeutic component. In certain embodiments, the outflow tract may be an artificial tract.

Specific embodiments comprise an insertion device configured or adapted to deliver a therapeutic component to a sinus outflow tract. In certain embodiments, the insertion device comprises: a shaft comprising a first end and a second end; an articulating portion proximal to the first end; a handle portion proximal to the second end; and a positioning member configured to move the articulating portion from a first position to a second position. In certain embodiments, the articulating portion comprises a plurality of articulating segments. In other embodiments, the articulating portion may comprise a cut tube (e.g. a spiral cut) or a coiled wire (e.g., a spring).

In particular embodiments, the articulating portion can be held in the second position when the first end of the shaft is inserted into a paranasal sinus comprising scar or granulation tissue. In specific embodiments, the articulating portion is held in the second position when the first end of the shaft is subjected to an external radial force and/or axial force of approximately 1.0, 0.9, 0.8, 0.7, 0.6, 0.5, 0.4, 0.3, 0.2, or 0.1 pounds or less. In particular embodiments, the insertion device comprises a tip that is rigid or semi-rigid that allows for insertion through scar or granulation tissue.

In certain embodiments, the shaft is approximately 1.0 mm to 5.0 mm in diameter and the tip is approximately 0.5 mm to 3.0 mm in diameter. In particular embodiments, the shaft is 1.0, 1.5, 2.0, 2.5, 3.0, 3.5, 4.0, 4.5 or 5.0 mm in diameter and the tip is 0.5, 1.0, 1.5, 2.0, 2.5, or 3.0 mm in diameter. In specific embodiments, the shaft is approximately 3.2 mm (0.125 inches) in diameter and the tip is 2.0 mm (0.080 inches) in diameter.

In particular embodiments, the articulating segments may be configured to articulate with a radius of curvature of approximately 5.0 mm to 25.0 mm. In particular embodiments, the articulating segments may be configured to articulate with a radius of curvature of approximately 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0 or 25.0 mm. In specific embodiments, the articulating segments may be configured to articulate with a radius of curvature of approximately 9.5 mm.

In specific embodiments, the shaft may be approximately 100 mm to 300 mm in length. In particular embodiments, the shaft may be approximately 100, 110, 120, 130, 140, 150, 160, 170, 180, 190, 200, 210, 220, 230, 240, 250, 260, 270, 280, 290 or 300 mm long.

In certain embodiments, the shaft may articulate so that the distal tip is oriented at an angle of approximately 60-110 degrees from the proximal end of the shaft. In particular embodiments, the shaft may articulate so that the distal tip is oriented at an angle of approximately 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 degrees from the proximal end of the shaft. In particular embodiments, the distal tip of the shaft may be pre-set at an angle of approximately 0-30 degrees prior to further articulation of up to 110 degrees.

In exemplary embodiments, the articulating segments may be configured similar to systems disclosed in U.S. Pat. Nos. 7,553,275 and 7,670,284, each titled "Medical Device with Articulating Shaft," which are incorporated by reference herein.

In certain embodiments, the articulating segments can include a plurality of independent pivot members and pins in an alternating configuration. In particular embodiments, each pivot member can define an opening while each pin can define a pin aperture. In specific embodiments, a first slat assembly and second slat assembly extend through the articulating segments. In certain embodiments, each of the first slat assembly and the second slat assembly is configured to push when the other of the first slat assembly and the second slat assembly pulls so as to cause the articulating segments to articulate.

In particular embodiments, the openings collectively define an outer passageway while the pin apertures collectively define an inner passageway. In certain embodiments, the first slat assembly can extend through the outer passageway alongside a first side of the pins while the second slat assembly can extend through the outer passageway alongside a second side of the pins opposite the first side of the pins. In exemplary embodiments, the inner passageway can provide a path for an actuator, a flexible tube, electrical wiring and/or light transmitting media, such as optical fibers, to extend through the articulating segments. The actuator may be formed with a variety of cross-sectional shapes, such as a rectangle, square, circle, etc.

In particular embodiments, the locking member comprises a pin extending from the positioning member. Certain embodiments may further comprise a location sensor configured to register the location of the first end of the shaft. Specific embodiments may comprise a therapeutic component coupled to the shaft proximal to the first end. The therapeutic component may be in fluid communication with a first coupling member configured to receive a pressurizing member, which can be a syringe in certain embodiments. The therapeutic component may be in fluid communication with a second coupling member configured to receive the shaft, and the second coupling member may comprise a pair of latching members configured to engage a flange on the shaft. The second coupling member may also comprise a pair of leverage members configured to open the latching members. Certain embodiments may comprise a sleeve extending between the therapeutic component and the coupling member, where the sleeve extends over the plurality of articulating portion.

In specific embodiments, the sleeve comprises a conduit in fluid communication with coupling member and the therapeutic component, which may be an inflatable balloon. In certain embodiments, the therapeutic component is configured to deliver fluid to the anatomical structure. In particular embodiments, a portion of the articulating portion extends into the therapeutic component.

Specific embodiments may comprise a locking member configured to lock the positioning member so that the articulating portion is held in the second position. In specific embodiments, the insertion device comprises a plurality of apertures configured for engagement with the locking member. Certain embodiments may further comprise a biasing member configured to bias the positioning member such that the locking member is engaged with one of the apertures.

Certain embodiments may include a method of providing therapy to a paranasal sinus outflow tract, where the method comprises: inserting a therapeutic component into the paranasal sinus outflow tract, where the therapeutic component is inserted into the paranasal sinus outflow tract without the use of a guide wire, cannula or guide sheath; and expanding the therapeutic component to enlarge the paranasal sinus outflow tract.

In specific embodiments, inserting the therapeutic component into the paranasal sinus outflow tract comprises providing a shaft with a distal end and an articulating portion; coupling the therapeutic component to the shaft; and inserting the distal end of the shaft into the paranasal sinus outflow tract. Particular embodiments may also comprise moving the articulating portion of the shaft from a first position to a second position; and engaging the distal end of the shaft with tissue proximal to the paranasal sinus outflow tract, where the articulating portion of the shaft remains in the second position when the distal end of the shaft engages the tissue proximal to the paranasal sinus outflow tract.

In specific embodiments, the tissue comprises scar or granulation tissue. Particular embodiments may further comprise dilating a therapeutic component proximal to the distal end of the shaft after the distal end has been inserted into a paranasal sinus. Specific embodiments may comprise tracking the location of the distal end of the shaft with a location sensor. In particular embodiments, the sinus is a frontal sinus. Certain embodiments may comprise delivering a therapeutic fluid to the paranasal sinus outflow tract.

Particular embodiments may comprise a method of dilating a paranasal sinus outflow tract, where the method comprises: inserting a therapeutic component into the paranasal sinus outflow tract, wherein the therapeutic component is coupled to a shaft with an articulating portion; expanding the therapeutic component from a first diameter to a second diameter, thereby dilating the paranasal sinus outflow tract; reducing the therapeutic component to the first diameter; and withdrawing the therapeutic component from the paranasal sinus outflow tract. In certain embodiments, the paranasal sinus outflow tract comprises granulation or scar tissue.

In certain embodiments, the shaft comprises a proximal end, a distal end, and the therapeutic component is located between the articulating portion and the distal end. In specific embodiments, inserting the therapeutic component into the paranasal sinus outflow tract comprises manipulating a positioning member configured to move the articulating portion of the shaft. In certain embodiments of the method, the articulating portion is configured to retain its shape when an external force is applied to the distal end. In particular embodiments, the external force is a radial force of approximately 0.5 pounds or less. In certain embodiments, the external force is an axial force of approximately 0.5 pounds or less. In particular embodiments of the method, the shaft is coupled to an insertion device comprising a positioning member configured to move the articulating portion of the shaft. In certain embodiments of the method, the insertion device comprises a locking member configured to lock the positioning member into a desired position. In specific embodiments of the method, inserting the therapeutic component into the paranasal sinus does not require the use of a guide wire or cannula. In particular embodiments, the paranasal sinus outflow tract comprises a maxillary, frontal or sphenoid sinus, and the therapeutic component is an inflatable balloon or a mechanical dilator. Specific embodiments comprise tracking the location of the therapeutic component with a location sensor.

Certain embodiments comprise: providing a stent disposed on the therapeutic component prior to inserting the therapeutic component into the paranasal sinus outflow tract; expanding the stent while expanding the therapeutic component; and withdrawing the therapeutic component from the stent so that the stent remains in the paranasal sinus outflow tract to maintain the dilated state for a period of time. In particular embodiments, the stent is bioabsorbable.

In certain embodiments, a bioabsorbable stent may be preferred to reduce the need for removal of the stent once the therapeutic effect has taken place, such as creating patency in the sinus opening throughout the healing period. In another embodiment, the stent may elude medications to create the therapeutic effect. These medications could include anti-inflammatory, antibiotic, steroid, etc. Since typical bioabsorbable stents are rigid, the stent could be composed of multiple leaflets that overlap in a slide and lock design to retain the shape of the ostium once inflated. Alternatively the stent could be composed of a magnesium based alloy that can retain its shape once expanded.

In exemplary embodiments, the stent device can be made of a biocompatible material. In particular embodiments, the stent device is made of a biodegradable material. In certain embodiments, the material is a biodegradable polymer. The material may be synthetic (e.g., polyesters, polyanhydrides) or natural (e.g., proteins, rubber, polysaccharides). In certain embodiments, the material is a homopolymer. In certain embodiments, the material is a co-polymer. In particular embodiments, the material is a block polymer. In other embodiments, the material is a branched polymer. In other embodiments, the material is a cross-linked polymer. In certain embodiments, the polymer is a polyester, polyurethane, polyvinyl chloride, polyalkylene (e.g., polyethylene), polyolefin, polyanhydride, polyamide, polycarbonate, polycarbamate, polyacrylate, polymethacrylate, polystyrene, polyurea, polyether, polyphosphazene, poly(ortho esters), polycarbonate, polyfumarate, polyarylate, polystyrene, or polyamine. In certain embodiments, the polymers is polylactide, polyglycolide, polycaprolactone, polydioxanone, polytrimethylene carbonate, and co-polymers thereof. Polymers that have been used in producing biodegradable implants and are useful in preparing the inventive devices include alpha-polyhydroxy acids; polyglycolide (PGA); copolymers of polyglycolide such as glycolide/L-lactide copolymers (PGA/PLLA), glycolide/D,L-lactide copolymers (PGA/PDLLA), and glycolide/trimethylene carbonate copolymers (PGA/TMC); polylactides (PLA); stereocopolymers of PLA such as poly-L-lactide (PLLA), poly-D,L-lactide (PDLLA), L-lactide/D,L-lactide copolymers; copolymers of PLA such as lactide/tetramethylglycolide copolymers, lactide/trimethylene carbonate copolymers, lactide/.delta.-valerolactone copolymers, lactide .epsilon.-caprolactone copolymers, polydepsipeptides, PLA/polyethylene oxide copolymers, unsymmetrically 3,6-substituted poly-1,4-dioxane-2,5-diones; polyhydroxyalkanate polymers including poly-beta-hydroxybutyrate (PHBA), PHBA/beta-hydroxyvalerate copolymers (PHBA/HVA), and poly-beta-hydroxypropionate (PHPA); poly-p-dioxanone (PDS); poly-.delta.-valerolatone; poly-r-caprolactone; methylmethacrylate-N-vinyl pyrrolidone copolymers; polyesteramides; polyesters of oxalic acid; polydihydropyrans; polyalkyl-2-cyanoacrylates; polyurethanes (PU); polyvinyl alcohol (PVA); polypeptides; poly-beta-maleic acid (PMLA); poly(trimethylene carbonate); poly(ethylene oxide) (PEO); poly(.beta.-hydroxyvalerate) (PHVA); poly(ortho esters); tyrosine-derived polycarbonates; and poly-beta-alkanoic acids. In certain embodiments, the polymer is a polyester such as poly(glycolide-co-lactide) (PLGA), poly(lactide), poly(glycolide), poly(D,L-lactide-co-glycolide), poly(L-lactide-co-glycolide), poly-.beta.-hydroxybutyrate, and polyacrylic acid ester. In certain embodiments, the stent device is made of PLGA.

In certain embodiments, the stent device is made of 85% D,L-lactide and 15% glycolide co-polymer. In certain embodiments, the device is made of 50% D,L-lactide and 50% glycolide co-polymer. In certain embodiments, the device is made of 65% D,L-lactide and 35% glycolide co-polymer. In certain embodiments, the device is made of 75% D,L-lactide and 25% glycolide co-polymer. In certain embodiments, the device is made of 85% L-lactide and 15% glycolide co-polymer. In certain embodiments, the device is made of 50% L-lactide and 50% glycolide co-polymer. In certain embodiments, the device is made of 65% L-lactide and 35% glycolide co-polymer. In certain embodiments, the device is made of 75% L-lactide and 25% glycolide co-polymer. In certain embodiments, the stent device is made of poly(caprolactone). In certain embodiments, the device is made of Pebax, Polyimide, Braided Polyimide, Nylon, PVC, Hytrel, HDPE, or PEEK. In certain embodiments, the device is made of a fluoropolymer such as PTFE, PFA, FEP, and EPTFE. In certain embodiments, the device is made of latex. In other embodiments, the device is made of silicone. In certain embodiments, the polymer typically has a molecular weight sufficient to be shaped by molding or extrusion.

In certain embodiments, the stent device may also be composed of natural materials derived from human or animal sources. In specific embodiments, the allogenic or human tissue grafts may be harvested from subjects other than the patient or from tissue banks For example, the xenogenic or animal tissue grafts can be derived from non-human species such as cows, pigs, etc.

In certain embodiments, allogenic or xenogenic tissues, such as dermis, fascia, pericardium, cartilage, tendon, ligament and similar materials, may be useful for stent constructs. In specific embodiments, the intercellular matrixes of these tissues are processed to preserve the biological structure and composition, but the cells which may cause an immune response are removed. These constructs may then be processed into sheets or tubes to serve in a stenting function and are known to resorb by cell phagocytosis.

In particular embodiments, the stent may also comprise autologous or culture grown tissue. In specific embodiments, the tissues may be processed and terminally sterilized to enhance their biocompatibility and foreign response.

In certain embodiments, the device is made of a material that is bioabsorbed after the device is no longer needed. For example, the device may degrade after 1 week, 2 weeks, 3 weeks, 1 month, 2 months, 3 months, 4 months, 5 months, 6 months, 9 months, 1 year, 1.5 years, 2 years, 3 years, etc. The polymer used to make the device may be selected based on its degradation profile. The polymer can be selected as is known to the art to have a desired degradation period. For an implant of this invention, the degradation period may be up to about 2 years, or between about 6 months and about 1 year. As would be appreciated by one of skill in this art, the composition of the device may be varied to achieve the desired lifetime in vivo of the device. The device may be manufactured using a heat molding, injection molding, extrusion, cutting or laser cutting to obtain the necessary features.

Certain embodiments may include fenestrations or cut outs which need to be rigid and stiff enough to be inserted, expand if needed and then hold the tissues apart or ostium open. Furthermore, these features may also be strong and somewhat elastic so that they do not easily fracture during the process of implantation. To achieve that property, the device may be composed of a crystalline or amorphous polymer combined with an elastomeric polymer. For example, a highly crystalline polylactide may be blended with a polyhydroxybutarate; specifically 80-97% PLLA and 20-3% PHA. Similarly, caprolactone or trimethyl carbonate may be added to the crystalline polymer to make it more elastic. Elasticity of the construct can be achieved through the addition of the caprolactone or trimethyl carbonate to a lactide or glycolide monomer since the caprolactone and trimethyl carbonate have relatively low melting temperatures, i.e. −60° C. for carpolactone.

In certain embodiments, the stent may have a coating or incorporate a drug in the implant itself to provide the release of a pharmaceutical agent, which may prevent the adhesion of the stent in place, may prevent cell growth or scar formation, may enhance tissue healing, etc. In exemplary embodiments, the coating or incorporated drug may be biocompatible. In certain embodiments, the coating is a polymeric coating. In certain embodiments, the coating is a polymeric coating that includes a therapeutic agent. Classes of therapeutic agents that may be delivered by the stent include DNA, RNA, nucleic acids, proteins, peptides, or small molecules. Exemplary therapeutic agents include antibiotics, anti-inflammatory agents, corticosteroids, vasoconstrictors, vasodilators, anti-allergy agents, anti-histamines, cromolyn sodium, decongestants, asthma treatments, etc. In certain embodiments, the coating or incorporated drug may include retinoic acid to enhance mucosal wound healing. In certain embodiments, the coating includes cytotoxic agents such as paclitaxel to prevent cell growth on the stent. In other embodiments, the coating is Teflon. The stent may be coated with a polysaccharide such as hyaluronate.

Synthetic bioactive agents include but are not limited to growth factors such as platelet derived growth factor (PDGF), fibroblast growth factor (FGF), insulin-like growth factor (IGF), transforming growth factor beta (TGF-.beta.), and other mitogenic or differentiation factors. Other synthetic bioactive agents could be small peptide analogues of the above-mentioned or other growth factors. Still other agents could be drugs or pharmacologically active substances which stimulate the growth or differentiation of tissue.

In certain embodiments, the stent may comprise anti-inflammatory and anti-infective agents, including for example, aminoglycosides, amphenicols, ansamycins, β-lactams, lincosamides, macrolides, nitrofurans, quinolones, sulfonamides, sulfones, tetracyclines, and any of their derivatives. In certain embodiments, β-lactams are the preferred antibacterial agents.

β-lactams that may be included in the stent implants include carbacephems, carbapenems, cephalosporins, cephamycins, monobactams, oxacephems, penicillins, and any of their derivatives. In certain embodiments, penicillins (and their corresponding salts) are the preferred β-lactams.

In particular embodiments, the penicillins that may be used in the biodegradable implants include amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin. In certain embodiments, amoxicillin may be included in the biodegradable implant. In particular embodiments, the biodegradable implant includes ampicllin. Penicillins combined with clavulanic acid such as Augmentin® (amoxicillin and clavulanic acid) may also be used.

Examples of antifungal agents that may be used in the biodegradable implants include allylamines, imidazoles, polyenes, thiocarbamates, triazoles, and any of their derivatives. In certain embodiments, imidazoles are the preferred antifungal agents.

In certain embodiments, if inclusion of an anti-inflammatory agent is desired, a steroidal anti-inflammatory agent, e.g., a corticosteroid, is employed. Examples of steroidal anti-inflammatory agents that may be used in the implants include 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives. In certain embodiments, budesonide is included in the implant as the steroidal anti-inflammatory agent. In particular embodiments, the steroidal anti-inflammatory agent may be mometasone furoate. In some embodiments, the steroidal anti-inflammatory agent may be beclomethasone.

Specific embodiments comprise an insertion device configured for inserting a therapeutic component into an anatomical structure, where the insertion device comprises: a shaft comprising a first end and a second end; a plurality of articulating segments proximal to the first end; a mating receptacle proximal to the first end; a handle portion proximal to the second end; a positioning member configured to move the articulating segments and the mating receptacle from a first position to a second position; and a locking member configured to lock the positioning member so that the articulating segments and the mating receptacle are held in the second position.

In specific embodiments, the locking member comprises a pin, which may extend from the positioning member or from the handle portion. In particular embodiments, the insertion device comprises a plurality of apertures configured for engagement with the pin. In certain embodiments, the plurality of apertures are located on the positioning member or on the handle portion. Particular embodiments may comprise a biasing member configured to bias the positioning member such that the pin is engaged with one of the apertures. In certain embodiments, the articulating segments are generally collinear with the shaft in the first position and the articulating segments are not collinear with the shaft in the second position. In specific embodiments, the mating receptacle is configured to engage a therapeutic component, which may be an inflatable balloon.

Particular embodiments may comprise an insertion device configured for inserting an elongate device into an anatomical structure, where the insertion device comprises:a shaft comprising a first end and a second end; a plurality of articulating segments proximal to the first end; a mating receptacle proximal to the first end; a handle portion proximal to the second end; and a positioning member configured to position the articulating segments and the mating receptacle.

Certain embodiments may comprise an elongate device configured for insertion into an anatomical structure, where elongate device comprises: an elongate shaft comprising a first end and a second end; a therapeutic component proximal to the first end of the elongate device; a conduit extending from the second end to the therapeutic component; and a coupling member coupled to the elongate shaft, wherein the coupling member is configured to be coupled to an insertion device. In particular embodiments, the coupling member is a protuberance extending from the elongate shaft. In certain embodiments, the therapeutic component comprises an inflatable balloon. In particular embodiments, the coupling member comprises a grasping member, which may comprise surgical tape wrapped around the elongate shaft. In certain embodiments, the coupling member comprises a molded tab (which may comprise a plastic material) configured to fit onto the elongate shaft.

Particular embodiments comprise a method of dilating an anatomical structure, where the method includes providing an elongate device comprising: an elongate shaft comprising a first end and a second end; a therapeutic component proximal to the first end of the elongate device; a conduit extending from the second end to the therapeutic component; and a coupling member coupled to the elongate shaft, wherein the coupling member is configured to be coupled to an insertion device; coupling an insertion device to the coupling member; inserting the elongate device into the anatomical structure; expanding the therapeutic component; and dilating the anatomical structure. In certain embodiments, coupling the insertion device to the coupling member comprises grasping the coupling member with a pair of forceps. In particular embodiments, expanding the therapeutic component comprises inflating an inflatable portion of the therapeutic component. In specific embodiments, the anatomical structure is a paranasal sinus. In certain embodiments, the insertion device is a pair of forceps, and in specific embodiments may be a pair of Blakesley type forceps or articulating forceps. In certain embodiments, the coupling member is a protuberance extending from the elongate shaft, and the therapeutic component comprises an inflatable balloon. In particular embodiments, providing a coupling member coupled to the elongate shaft comprises placing a grasping member on the elongate shaft, and the grasping member may comprise surgical tape.

Certain embodiments comprise a system for dilating an anatomical structure, where the system includes an insertion device and an elongate device. The elongate device may comprise: an elongate shaft comprising a first end and a second end; a therapeutic component proximal to the first end of the elongate shaft; a conduit extending from the second end to the therapeutic component; and a coupling member coupled to the elongate shaft, wherein the insertion device is configured to grasp the coupling member. In particular embodiments, expanding the therapeutic component comprises inflating an inflatable portion of the therapeutic component.

Particular embodiments may comprise an insertion device configured for inserting an elongate device into an anatomical structure, where the insertion device comprises: a shaft comprising a first end and a second end; a plurality of articulating segments proximal to the first end; a mating receptacle proximal to the first end, wherein the mating receptacle is configured to engage the elongate device; a handle portion proximal to the second end; and a positioning member configured to position the articulating segments and the mating receptacle. Particular embodiments may further comprise a location sensor configured to register the location of the mating receptacle. In certain embodiments, the mating receptacle comprises a slot with a first angled portion configured to engage a second angled portion of an elongate device. In particular embodiments, the mating receptacle comprises a retaining mechanism. Certain embodiments may further comprise a release actuator.

Specific embodiments may comprise a system for dilating an anatomical structure, where the system comprises an insertion device and an elongate device. In certain embodiments, the insertion device comprises: a shaft comprising a first end and a second end; a plurality of articulating segments proximal to the first end; a mating receptacle proximal to the first end, wherein the mating receptacle is configured to engage the elongate device; a handle portion proximal to the second end; and a positioning member configured to position the articulating segments and the mating receptacle. In specific embodiments, the elongate device comprises: an elongate shaft comprising a first end and a second end; a therapeutic component proximal to the first end of the elongate shaft; a conduit extending from the second end to the therapeutic component; and a coupling member coupled to the elongate shaft, where the mating receptacle is configured to engage the coupling member.

In particular embodiments, the mating receptacle comprises a slot configured to engage an extension of the coupling member. In certain embodiments, the mating receptacle comprises a retaining mechanism. In another embodiment, the mating receptacle comprises a geometric feature such as a flange, protuberance, or groove, and the coupling member on the elongate device comprises latching features which engage the geometric features to secure the elongate device to the shaft.

Specific embodiments may comprise an insertion device configured for inserting a therapeutic component into an anatomical structure, where the insertion device comprises: a shaft comprising a first end and a second end; a mating receptacle proximal to the first end, wherein the mating receptacle is configured to engage a therapeutic component; and a positioning member. In certain embodiments, the positioning member can be placed in a first position wherein the positioning member is generally straight, and the positioning member can be placed in a second position wherein a portion of the positioning member is curved. In certain embodiments, the positioning member comprises a spring or elastic material. In particular embodiments, the spring or elastic material is nitinol.

In particular embodiments, the positioning member does not extend past the first end of the shaft when the positioning member is in the first position, and the positioning member extends past the first end of the shaft when the positioning member is in the second position. Certain embodiments further comprise a control member proximal to the second end of the shaft, where the control member is configured to move the positioning member from the first position to the second position. In particular embodiments, the positioning member is configured to deflect a therapeutic component engaged to the mating receptacle when the positioning member is in the second position.

Certain embodiments comprise a system including a therapeutic component configured for insertion into an anatomical structure, the system comprising: a therapeutic component comprising a central lumen; a coupling member extending into the central lumen of the therapeutic component, where the coupling member is configured to engage an insertion device configured to insert the therapeutic component into an anatomical structure; and a conduit configured to expand the therapeutic component. In particular embodiments, the conduit is coaxial with the coupling member, while in other embodiments, the conduit is not coaxial with the coupling member. In certain embodiments, the coupling member comprises a rigid shaft.

Particular embodiments comprise a system configured for insertion into an anatomical structure, where the system comprises: an insertion device comprising an articulating portion; and a therapeutic component comprising a first lumen and a second lumen, where first lumen is configured to receive the articulating portion of the insertion device and the second lumen is in fluid communication with a conduit. In particular embodiments, the conduit is configured to inflate and deflate the therapeutic component.

Certain embodiments may comprise a system configured for insertion into an anatomical structure, where the system comprises: an insertion device comprising a first end, a second end, and an enlarged portion proximal to the second end; a therapeutic component comprising a first lumen having a receiving member configured to receive the enlarged portion of the insertion device. In certain embodiments, the therapeutic component comprises a second lumen in fluid communication with a conduit. In certain embodiments, the insertion device comprises an angled portion between the first end and the second end. In particular embodiments, the insertion device is an ostium seeker.

Certain embodiments may comprise a system for dilating paranasal ostium comprising: a therapeutic component comprising a first lumen and a second lumen; an insertion device comprising a handle portion and a shaft, wherein the shaft is configured for insertion into the first lumen; a conduit coupled to the second lumen; and a pressurizing member in fluid communication with the conduit and the second lumen, where the pressurizing member is configured to expand the therapeutic component.

In particular embodiments, the therapeutic component is removable from the insertion device. In certain embodiments, the therapeutic component is disposable and the insertion device is reusable. In specific embodiments, the therapeutic component and insertion device are disposable. In particular embodiments, the therapeutic component is integral with the shaft of the insertion device. In certain embodiments, the shaft comprises a preset rigid angle. In particular embodiments, the preset rigid angle is between 0 and 110 degrees. In certain embodiments, the preset rigid angle is 0, 5, 10, 15, 20, 25, 30, 35, 40, 45, 50, 55, 60, 65, 70, 75, 80, 85, 90, 95, 100, 105 or 110 degrees.

In specific embodiments, the shaft may be configured to articulate. In certain embodiments, shaft is configured to articulate from 0 to 110 degrees, and in particular embodiments, the shaft is configured to articulate from 30 to 90 degrees, or from 35 to 85 degrees, or from 40 to 80 degrees, or from 45 to 75 degrees, or from 50 to 70 degrees or from 55 to 65 degrees. In certain embodiments, the shaft is configured to lock at pre-set angles. In particular embodiments, the shaft comprises one or more pivot members. In specific embodiments, the shaft comprises multiple articulating links. In particular embodiments, the insertion device comprises a positioning member configured to be straight when in a retracted position and configured to be curved when in an extended position. In certain embodiments, the insertion device is configured to extend the therapeutic component away from the handle portion. In particular embodiments, the shaft is configured to extend and articulate. In certain embodiments, the therapeutic component comprises a coupling member configured to couple with the insertion instrument.

In specific embodiments, the coupling member comprises a lumen configured to accept a distal end of the shaft of the insertion device. Particular embodiments comprise a protuberance on a proximal end of the therapeutic component which fits into a slot on the shaft of the insertion device. In certain embodiments, the coupling member comprises an external thread mating with an internal thread on the shaft of the insertion device. In specific embodiments, the coupling member comprises an internal thread mating with an external thread on the shaft of the insertion device. In particular embodiments, the insertion device shaft comprises a retention mechanism configured to retain the therapeutic component to the shaft during use. In certain embodiments, the retention mechanism comprises retaining members configured to move from an expanded position to a compressed position as the therapeutic component is installed on the shaft. In specific embodiments, the retaining members are biased to the expanded position after the therapeutic component is installed on the shaft. In particular embodiments, the shaft comprises a retaining member and the therapeutic component is coupled to a collar comprising a receiving member, and the retaining member is configured to engage the receiving member when the therapeutic component is coupled to the shaft. In another embodiment, the collar is on the shaft of the insertion device, and the retaining members are on the coupling member of the elongate device.

In certain embodiments, the retaining member comprises a pin biased to an extended position and wherein the receiving member comprises an aperture. In specific embodiments, the retaining member comprises a pin biased to an extended position and the receiving member comprises a J-shaped slot. In particular embodiments, the retention mechanism can be manipulated via a release mechanism coupled to the handle portion. In certain embodiments, the handle portion comprises an actuator configured to articulate the shaft. In specific embodiments, the handle portion comprises an actuator configured to extend the shaft. In certain embodiments, the handle portion comprises an actuator configured to release the therapeutic component from the shaft. In particular embodiments, the handle portion comprises a location sensor. In particular embodiments, the handle portion comprises a location sensor configured to track movement of the distal end of the shaft.

Certain embodiments comprise a system for delivering a stent to paranasal sinus passage, the system comprising: a stent; means for deploying the stent; and an insertion system. In certain embodiments, the means for deploying the stent comprises an expansion member, which may be a balloon. In particular embodiments, the stent is configured to be expanded by a balloon. In certain embodiments, the stent is self expanding and the deployment means comprises a retracting sleeve. In certain embodiments, the insertion system is configured to articulate. In particular embodiments, the insertion system comprises multiple links. In specific embodiments, the insertion system pivots about a pivot member. In certain embodiments, the insertion system configured to extend and/or articulate. In specific embodiments, the insertion system comprises a location sensor.

Certain embodiments comprise a system for dilating a paranasal sinus, where the system comprises: a therapeutic component configured to expand from a reduced diameter to an increased diameter; and an insertion system, where the insertion system is configured to insert the therapeutic component in the paranasal sinus when the therapeutic component has a reduced diameter and where the insertion system is configured to expand the therapeutic component to the increased diameter when the therapeutic component is placed in a desired location within the paranasal sinus.

In certain embodiments, the insertion system is configured to insert the therapeutic component into the paranasal sinus via a guide wire. In particular embodiments, the guide wire comprises an anchor member, which may be inflatable and/or mechanically expandable in certain embodiments. The insertion system may be configured to insert the therapeutic component into the paranasal sinus over a guide cannula.

Particular embodiments may comprise a method of dilating paranasal sinus passage, where the method comprises: positioning a therapeutic component across a paranasal sinus using a hand-held surgical instrument; expanding the therapeutic component; and removing the therapeutic component from the paranasal sinus. In certain embodiments, the sinus has previously been surgically altered. In particular embodiments, the sinus is a frontal sinus, a maxillary sinus, or a sphenoid sinus. In certain embodiments, positioning the therapeutic component in the sinus comprises coupling the therapeutic component to an articulating shaft. In specific embodiments, positioning the therapeutic component in the sinus comprises coupling the therapeutic component to an extending shaft. In particular embodiments, positioning the therapeutic component in the sinus comprises coupling the therapeutic component to a shaft that can be articulated and extended.

In certain embodiments, positioning the therapeutic component in the sinus comprises the use of a location sensor in conjunction with an image guidance system. In certain embodiments, positioning the therapeutic component in the sinus comprises the use of an instrument guidance system calibrated to document the location of the therapeutic component at a plurality of preset positions. In particular embodiments, the therapeutic component is positioned and expanded with the hand-held surgical instrument. Certain embodiments comprise releasing the therapeutic component from the hand-held surgical instrument after the therapeutic component has been positioned; removing the hand-held surgical instrument from the paranasal sinus; and expanding the therapeutic component. In specific embodiments, the therapeutic component is a mechanically expandable dilator. In particular embodiments, the therapeutic component is an inflatable balloon, and the means for expanding comprise inflating the balloon with an inflation device.

Specific embodiments include a method of dilating a paranasal sinus, where the method comprises: inserting a first non-expandable therapeutic component into the paranasal sinus, wherein the first non-expandable therapeutic component comprises a first maximum diameter; removing the first non-expandable therapeutic component from the paranasal sinus; inserting a second non-expandable therapeutic component into the paranasal sinus, wherein the second non-expandable therapeutic component comprises a second maximum diameter; and removing the second non-expandable therapeutic component from the paranasal sinus, where the second maximum diameter is greater than the first maximum diameter.

Certain embodiments further comprise: inserting a third non-expandable therapeutic component into the paranasal sinus, where the third non-expandable therapeutic component comprises a third maximum diameter; and removing the third non-expandable therapeutic component from the paranasal sinus, where the third maximum diameter is greater than the first maximum diameter and the second maximum diameter. In particular embodiments, the first and second non-expandable therapeutic components comprise tapered surfaces and a rounded end portion configured to reduce trauma to tissue surrounding the paranasal sinus. In certain embodiments, the first and second non-expandable therapeutic components comprise a lumen configured to receive a guide wire. In specific embodiments, the guide wire comprises an anchor member, which may be inflatable.

Particular embodiments comprise a method of dilating a paranasal sinus, where the method comprising: providing a therapeutic component and a flexible endoscope; coupling the therapeutic component to the flexible endoscope; inserting the therapeutic component into a paranasal sinus; utilizing the flexible endoscope to visualize a location within the paranasal sinus; and utilizing the therapeutic component to dilate the paranasal sinus. Certain embodiments comprise providing a light on the flexible endoscope and utilizing the light to transilluminate the sinus. Specific embodiments further comprise using a light on the flexible endoscope to assist in placement of the therapeutic component within the nasal sinus. Certain embodiments further comprise providing an insertion device and coupling the therapeutic component and flexible endoscope to the insertion device to position the therapeutic component in the paranasal sinus. In specific embodiments, the insertion device is articulating, and the method further comprises articulating the delivery device during positioning of the therapeutic component is in the nasal sinus. Particular embodiments further comprise preparing the paranasal sinus to receive the therapeutic component prior to inserting the therapeutic component into the nasal passageway.

Certain embodiments further comprise: removing the therapeutic component from the paranasal sinus after dilating the paranasal sinus; visualizing the paranasal sinus with the endoscope; and re-inserting the therapeutic component or another therapeutic component into the paranasal sinus. Particular embodiments further comprise expanding the therapeutic component to expand the paranasal sinus. Certain embodiments further comprise inserting the therapeutic component further into the paranasal sinus to expand a more distal portion of the paranasal sinus.

Specific embodiments include a method of implanting a stent in a paranasal sinus, where the method comprises: providing a stent deployment component with a stent disposed on the stent deployment component; providing an insertion device; attaching the stent deployment component to the insertion device; inserting the stent deployment component into the paranasal sinus using the insertion device; and deploying the stent. In certain embodiments, the stent deployment component is an inflatable balloon, and deploying the stent comprises inflating the balloon. In specific embodiments, the insertion device is articulating, and inserting the stent deployment component further comprises articulating the insertion device. In particular embodiments, the insertion device further comprises a location sensor, and where inserting the stent deployment component further comprises locating the tip of the insertion device using image guidance technology.

In specific embodiments, the stent deployment component comprises an inner shaft and a retractable sleeve, and deploying the stent comprises retracting the sleeve. Particular embodiments further comprise providing a retention feature on the inner shaft, where the retention feature is configured to retain the stent on the inner shaft during stent positioning.

Certain embodiments comprise a method of providing therapy to a paranasal sinus outflow tract, the method comprising: inserting a therapeutic component into a paranasal sinus outflow tract, wherein the therapeutic component is inserted into the paranasal sinus outflow tract without the use of a guide wire, cannula or guide sheath; emitting a high frequency pressure wave from the therapeutic component; and enlarging the paranasal sinus outflow tract via the high frequency pressure wave. In particular embodiments, the high frequency pressure wave is between 21 kHz and 30 kHz, more specifically between 21 kHz and 29 kHz, more specifically between 23 kHz and 28 kHz and more specifically between 24 kHz to 27 kHz. In other embodiments, the high frequency pressure wave is between 50 kHz and 26.5 MHz. In certain embodiments, the high frequency pressure wave comprises a radio frequency pressure wave. In particular embodiments, the high frequency pressure wave comprises an ultrasonic frequency pressure wave.

In specific embodiments, inserting the therapeutic component into the paranasal sinus outflow tract comprises: providing a shaft with a distal end and an articulating portion; coupling the therapeutic component to the shaft; and inserting the distal end of the shaft into the paranasal sinus outflow tract. Particular embodiments may comprise moving the articulating portion of the shaft from a first position to a second position; and engaging the distal end of the shaft with tissue proximal to the paranasal sinus outflow tract, wherein the articulating portion of the shaft remains in the second position when the distal end of the shaft engages the tissue proximal to the paranasal sinus outflow tract. In certain embodiments, the tissue comprises scar or granulation tissue. Specific embodiments may also comprise tracking the location of the distal end of the shaft with a location sensor. Particular embodiments may further comprise delivering a therapeutic fluid to the paranasal sinus outflow tract. In certain embodiments, the paranasal sinus outflow tract comprises a frontal sinus.

Particular embodiments may also comprise a method of dilating a paranasal sinus outflow tract, where the method comprises: inserting a therapeutic component into the paranasal sinus outflow tract, wherein the therapeutic component is coupled to a shaft with an articulating portion; emitting a high frequency pressure wave from the therapeutic component and enlarging the paranasal sinus outflow tract; and withdrawing the therapeutic component from the paranasal sinus outflow tract. In specific embodiments, the paranasal sinus outflow tract is enlarged by destructing tissue and removing tissue in the paranasal sinus outflow tract. In certain embodiments, the high frequency pressure wave comprises a radio frequency pressure wave. In particular embodiments, the high frequency pressure wave comprises an ultrasonic frequency pressure wave. In certain embodiments, the paranasal sinus outflow tract comprises granulation or scar tissue. In specific embodiments, the shaft comprises a proximal end and a distal end, and wherein the therapeutic component is located between the articulating portion and the distal end.

In particular embodiments, inserting the therapeutic component into the paranasal sinus outflow tract comprises manipulating a positioning member configured to move the articulating portion of the shaft. In certain embodiments, the articulating portion is configured to retain its shape when an external force is applied to the distal end. In specific embodiments, the external force is a radial or axial force of approximately 0.5 pounds or less. In certain embodiments, the shaft is coupled to an insertion device comprising a positioning member configured to move the articulating portion of the shaft. In particular embodiments, the insertion device comprises a locking member configured to lock the positioning member into a desired position. In specific embodiments, inserting the therapeutic component into the paranasal sinus does not require the use of a guide wire or cannula. In particular embodiments, the paranasal sinus outflow tract comprises a maxillary, sphenoid, or a frontal sinus.

In certain embodiments, the therapeutic component is an inflatable balloon. In particular embodiments, the therapeutic component is a mechanical dilator. Specific embodiments may further comprise tracking the location of the therapeutic component with a location sensor.

Particular embodiments may also comprise providing a stent disposed on the therapeutic component prior to inserting the therapeutic component into the paranasal sinus outflow tract; expanding the stent while expanding the therapeutic component; and withdrawing the therapeutic component from the stent so that the stent remains in the paranasal sinus outflow tract to maintain the dilated state for a period of time.

In certain embodiments, the stent is bioabsorbable. In particular embodiments, the stent is configured to elude a therapeutic agent. In specific embodiments, the therapeutic agent is selected from the group consisting of: antibiotics, anti-inflammatory agents, corticosteroids, vasoconstrictors, vasodilators, anti-allergy agents, anti-histamines, cromolyn sodium, decongestants, and asthma treatments. In certain embodiments, the stent comprises a bioabsorbable material selected from the group consisting of: polymers, polyesters, polyanhydrides, proteins, rubber, polysaccharides, xenografts and allografts.

Particular embodiments comprise a method of providing therapy to a paranasal sinus outflow tract, where the method comprises: inserting a therapeutic component into a paranasal sinus outflow tract, wherein the therapeutic component is inserted into the paranasal sinus outflow tract without the use of a guide wire, cannula or guide sheath; emitting an ultrasonic frequency from the therapeutic component; and enlarging the paranasal sinus outflow tract via the ultrasonic frequency.

Specific embodiments may also comprise a method of providing therapy to a paranasal sinus outflow tract, where the method comprises: inserting a therapeutic component into the paranasal sinus outflow tract, wherein the therapeutic component is inserted into the paranasal sinus outflow tract without the use of a guide wire, cannula or guide sheath; and exposing tissue in the paranasal sinus outflow tract to a cryogenic temperature.

In certain embodiments, the tissue in the paranasal sinus outflow tract shrinks after exposure to the cryogenic temperature. In particular embodiments, the tissue in the paranasal sinus outflow tract is damaged after exposure to the cryogenic temperature.

Particular embodiments may comprise a method of dilating a paranasal sinus outflow tract, where the method comprises: inserting a therapeutic component into the paranasal sinus outflow tract, wherein the therapeutic component is coupled to a shaft with an articulating portion; emitting a cryogenic temperature from the therapeutic component; and withdrawing the therapeutic component from the paranasal sinus outflow tract. In certain embodiments, tissue in the paranasal sinus outflow tract shrinks after the therapeutic component emits a cryogenic temperature cryogenic temperature. In specific embodiments, the tissue in the paranasal sinus outflow tract is damaged after the therapeutic component emits a cryogenic temperature cryogenic temperature.

BRIEF DESCRIPTION OF THE DRAWINGS

FIGS. 2J and 2K illustrate perspective views of the paranasal sinus ostia of FIGS. 2B-2J before and after dilation.

FIGS. 4A-4D illustrate perspective views of an insertion device and a therapeutic component according to exemplary embodiments of the present disclosure.

FIGS. 5A-5D illustrate perspective and orthogonal views of a therapeutic component according to exemplary embodiments of the present disclosure.

FIGS. 6A-6D illustrate perspective and orthogonal views of a therapeutic component according to exemplary embodiments of the present disclosure.

FIGS. 7A-7B illustrate section views of a therapeutic component according to exemplary embodiments of the present disclosure.

FIGS. 8A-8B illustrate section views of a therapeutic component according to exemplary embodiments of the present disclosure.

FIGS. 9A-9B illustrate section views of a therapeutic component according to exemplary embodiments of the present disclosure.

FIGS. 10A-10B illustrate section views of a therapeutic component according to exemplary embodiments of the present disclosure.

FIG. 13A illustrates a side view of a paranasal sinus with a therapeutic component of inserted into the sinus according to exemplary embodiments of the present disclosure.

FIG. 22A-22B illustrate section views of a therapeutic component according to exemplary embodiments of the present disclosure.

DETAILED DESCRIPTION

Figure 1A:
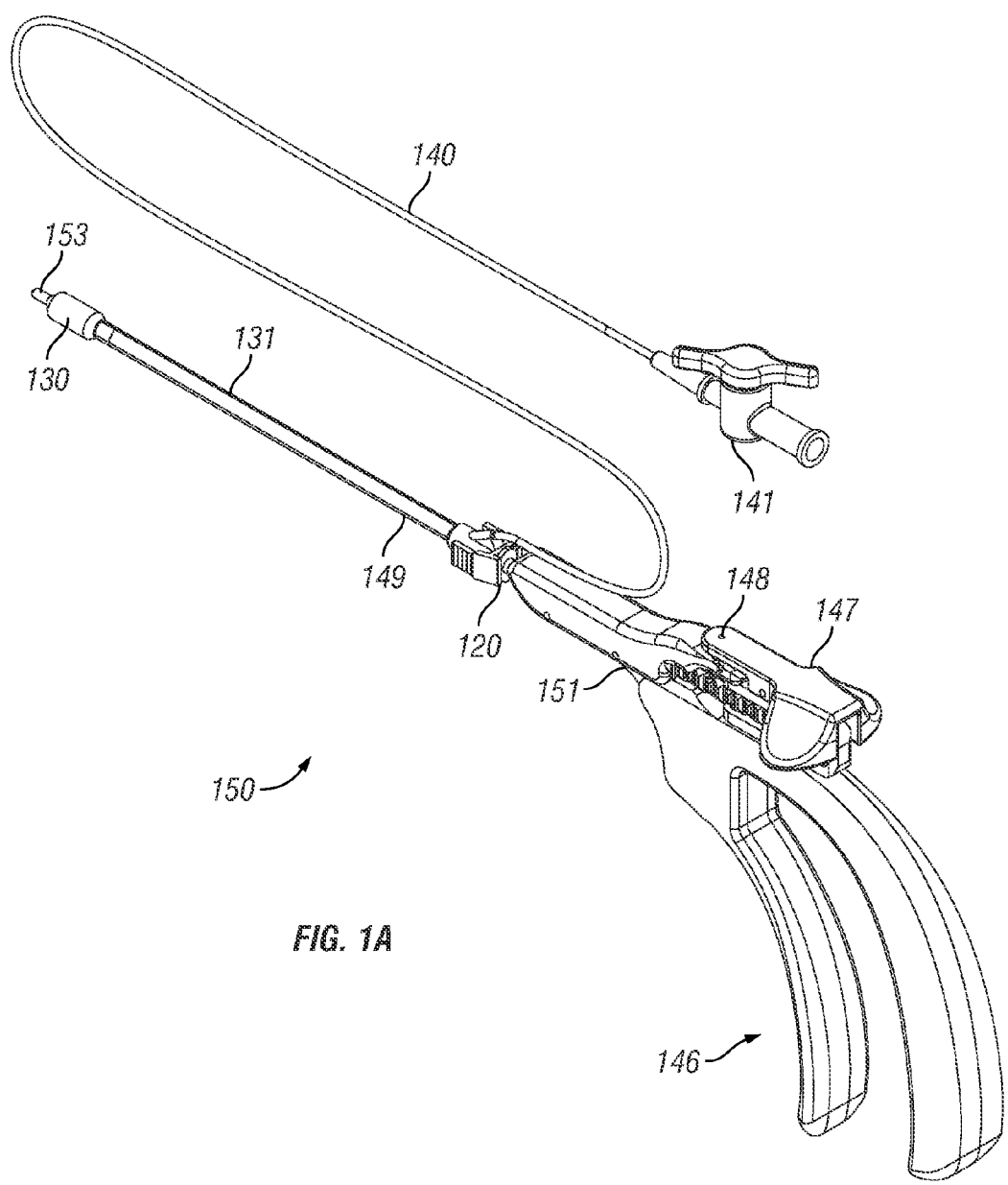
FIGS. 1A-1C illustrate perspective views of an insertion device and a therapeutic component according to exemplary embodiments of the present disclosure.
Figure 1B:
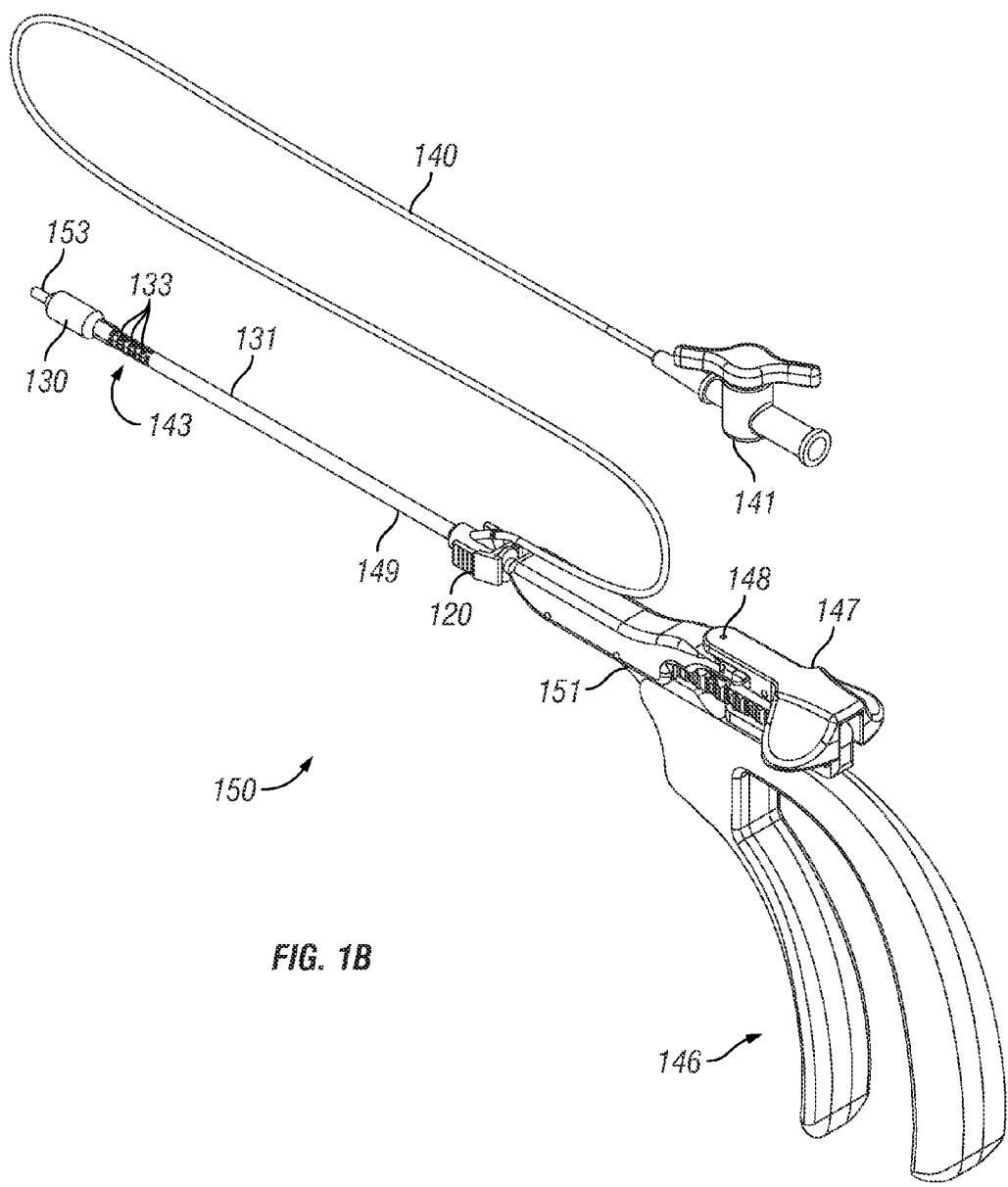
Figure 1C:
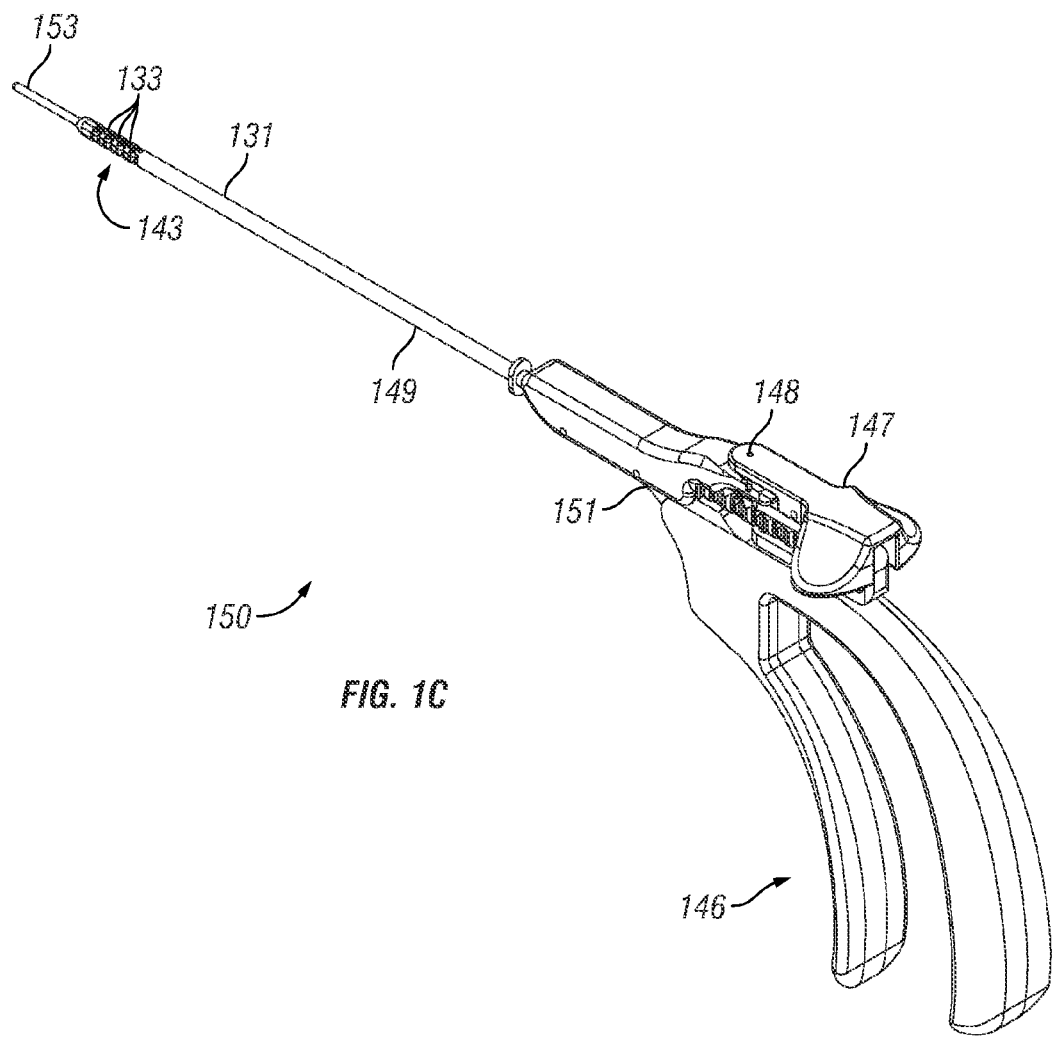

Exemplary embodiments of the present disclosure provide systems, devices and methods for providing therapy to anatomical structures. In particular embodiments, the therapy comprises dilation of a paranasal sinus. Exemplary embodiments provide the ability to articulate an instrument and maintain the instrument in the articulated position when it is subjected to external forces. This rigidity of the articulated instrument can allow a user to extend the instrument into a paranasal ostium that may include granulation or scar tissue.

Multiple exemplary embodiments are disclosed in the description that follows. It is understood that various components of the disclosed embodiments can be combined to form additional exemplary embodiments. For example, a handle portion from one disclosed embodiment may be combined with a shaft portion of another disclosed embodiment. Such combinations are within the scope of this disclosure, which is not limited to the specific combinations of features and components illustrated in the exemplary embodiments.

Exemplary Embodiment of Articulating Device

Referring initially to FIGS. 1A-1D, an exemplary embodiment comprises an insertion device 150 coupled to a therapeutic component 130. In this embodiment, insertion device 150 comprises a handle portion 146, a transition portion 151, and a shaft portion 149, which further comprises a distal end 153 and an articulating portion 143 (visible in FIGS. 1B and 1C). In the embodiment shown, therapeutic component 130 comprises an extended portion or sleeve 131 configured to cover shaft portion 149, including articulating portion 143. Sleeve 131 is not shown in FIG. 1B for purposes of clarity so that articulating portion 143 may be shown. In exemplary embodiments, articulating portion 143 may be configured similar to systems disclosed in U.S. Pat. Nos. 7,553,275 and 7,670,284, each titled "Medical Device with Articulating Shaft," which are incorporated by reference herein.

In this embodiment, insertion device 150 also comprises a positioning member 147 configured to articulate articulating portion 143 and a locking member 148 configured to lock positioning member 147 (and articulating portion 143) into a desired location. A biasing member (not visible in the figures) can bias positioning member 147 toward engagement with locking member 148. In certain embodiments, locking member 148 may comprise a pin that extends from positioning member 147 and into one of a plurality of apertures or recesses 144 (visible in FIG. 1D) in transition portion 151. As explained in more detail below, positioning member 147 can be manipulated to move articulating portion 143 and therapeutic component 130 into a desired position. In addition, the engagement of locking member 148 and a recess 144 can hold articulating portion 143 and therapeutic component 130 in the desired position.

Figure 1D:
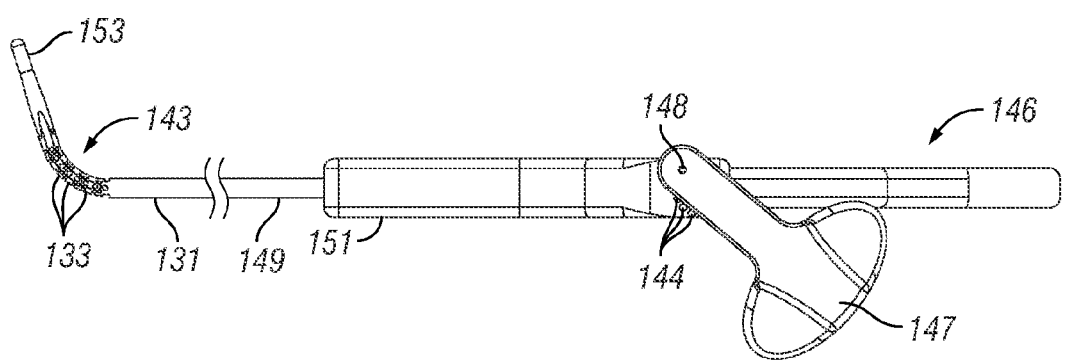
FIG. 1D illustrates a top view of the embodiment of FIGS. 1A-1C.

In the particular embodiment shown, the portion of positioning member 147 that is distal from locking member 148 can be pushed downward toward handle portion 146. This movement can withdraw locking member 148 from a recess 144 and allow positioning member 147 to be rotated or pivoted as shown in FIG. 1D. When the desired amount of articulation is achieved, the user can release positioning member 147 so that locking member 148 engages one of apertures 144 in positioning member 147. Locking member 148 can then retain positioning member 147, articulating portion 143, and therapeutic component 130 in the desired position. As explained in more detail below, articulating portion 143 is configured so that it is substantially rigid and maintains its shape when an external force is applied to distal end 153 or articulating portion 143.

Figure 1E:
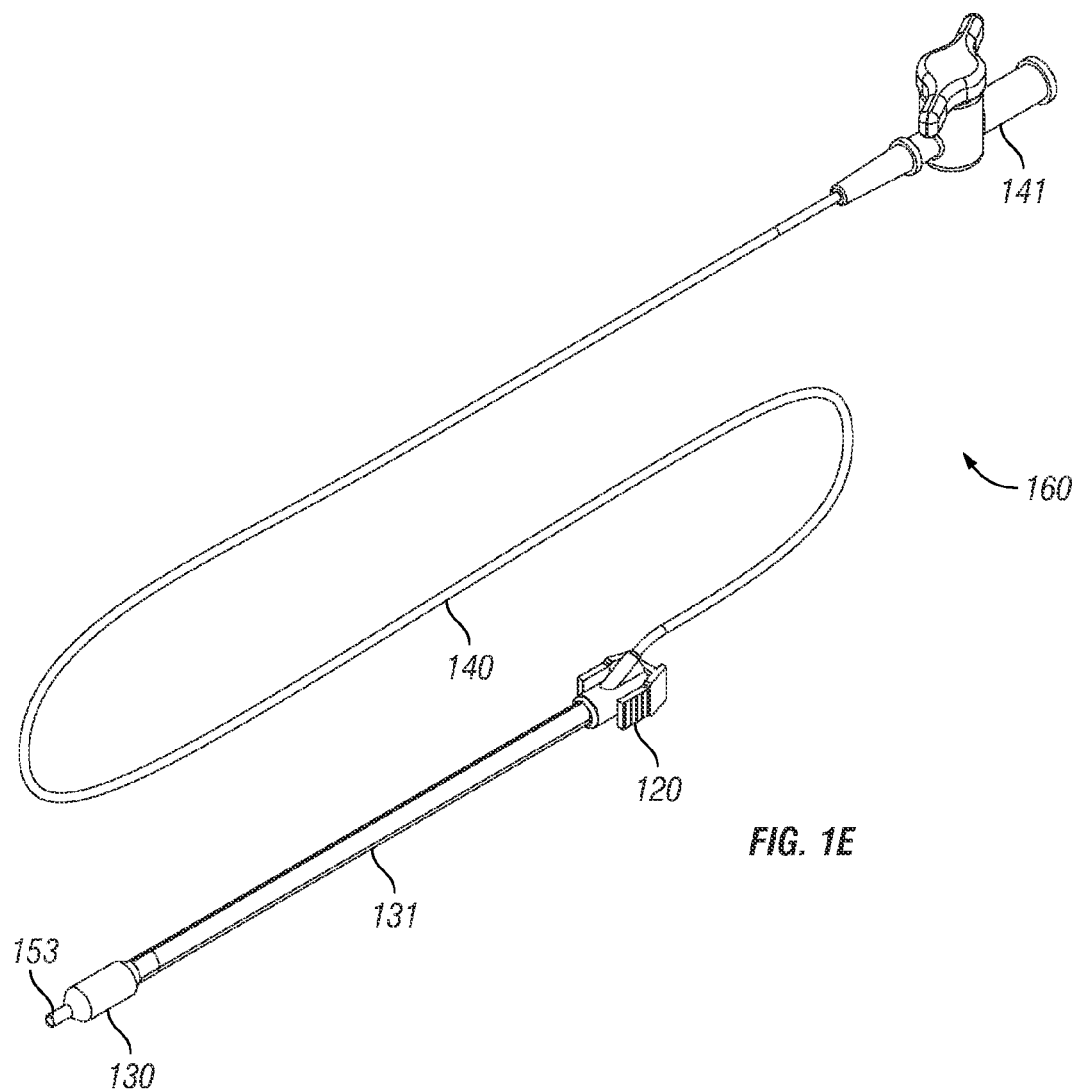
FIG. 1E illustrates a perspective view of a portion of the embodiment of FIGS. 1A-1C.
Figure 1F:
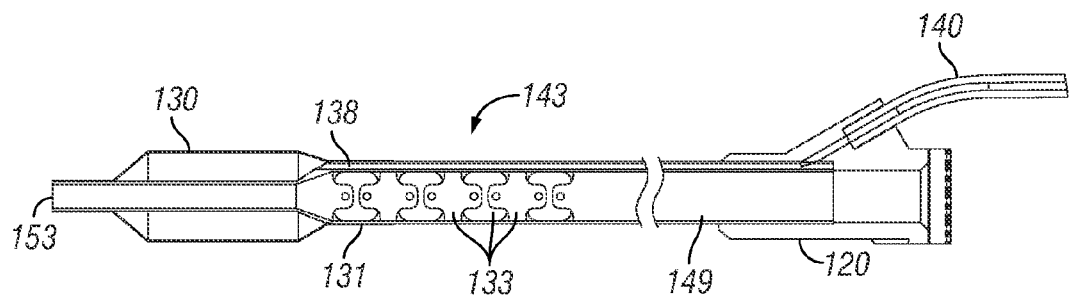
FIGS. 1F-1G illustrate section views of a portion of the embodiment of FIGS. 1A-1C.

Referring now to FIG. 1F, a detailed cross-section view of therapeutic component 130 and articulating section 143 is provided. In the particular embodiment shown in FIG. 1F, articulating section 143 comprises articulating segments 133 as disclosed in U.S. Pat. Nos. 7,553,275 and 7,670,284 and incorporated herein by reference. When positioning member 147 is held in a position (e.g., locking member 148 is engaged with an aperture 144), articulating segments 133 will also be held in position. During use, the ability to hold articulating segments 133 into position can provide a user with the ability to extend therapeutic component 130 into openings (e.g. paranasal sinus ostia) that may offer resistance to the advancement of therapeutic component 130.

Referring now to FIG. 1E, a therapeutic assembly 160 comprises a first coupling member 120, a second coupling member 141, and a conduit 140 in fluid communication with first and second coupling members 120, 141. As shown in FIG. 1A, coupling member 120 can be configured to couple to shaft portion 149 of insertion device 150 and sleeve 131. Coupling member 141 can be configured to couple to a pressurizing member (not shown) including, for example, a syringe. In certain embodiments, therapeutic assembly may be configured to expand therapeutic component 130, and/or deliver fluids to therapeutic component 130.

Figure 1G:
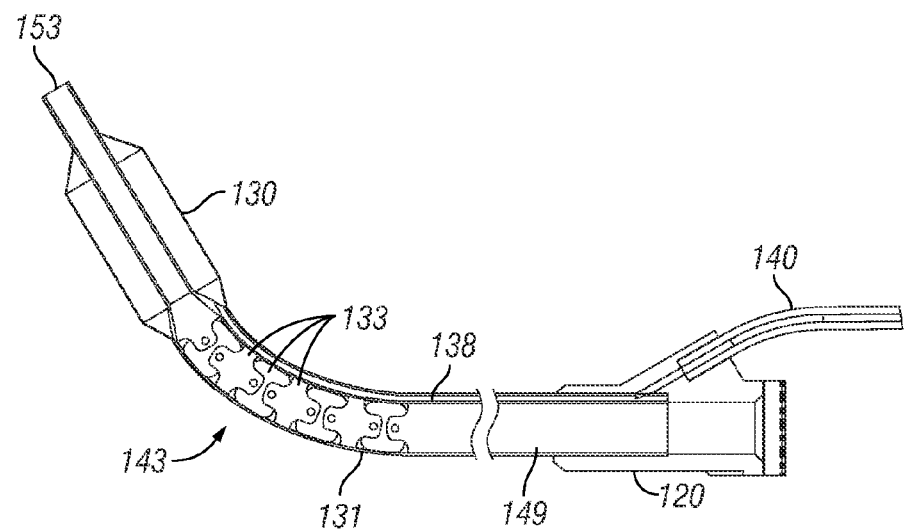

In certain embodiments, therapeutic component 130 may be configured as an inflatable balloon, which may be located between articulating portion 143 and distal end 153 or may be disposed partially or completely on articulating portion 143. In the embodiment shown, sleeve 131 comprises a conduit 138 in fluid communication with coupling member 120 and conduit 140, which can be coupled to a pressurizing member via coupling member 141. In certain embodiments, the pressurizing member may be a syringe filled with saline, or a balloon inflation device. When therapeutic component 130 is positioned in a target anatomy (e.g., a paranasal sinus such as a maxillary or frontal sinus), the pressurizing member can apply fluid pressure to therapeutic component 130 (via conduits 138 and 140) and expand therapeutic component 130. As shown in FIG. 1G, articulating portion 143 can be articulated with therapeutic component 130 coupled to shaft portion 149.

Figure 1H:
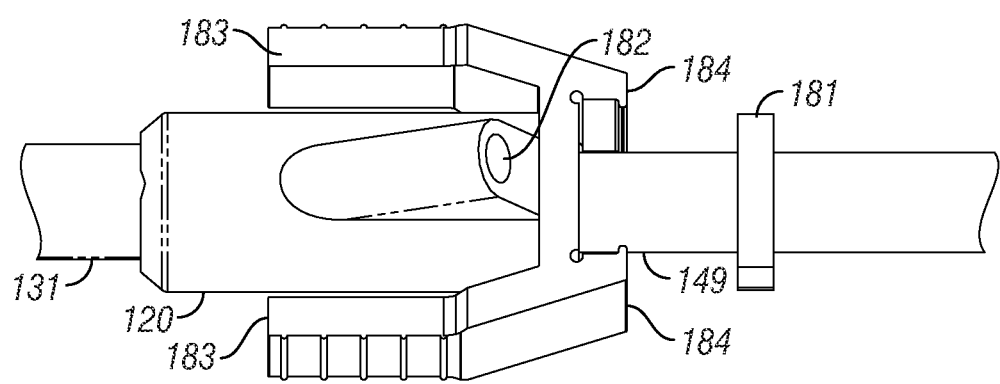
FIGS. 1H-1J illustrate perspective views of a portion of the embodiment of FIGS. 1A-1C.
Figure 1I:
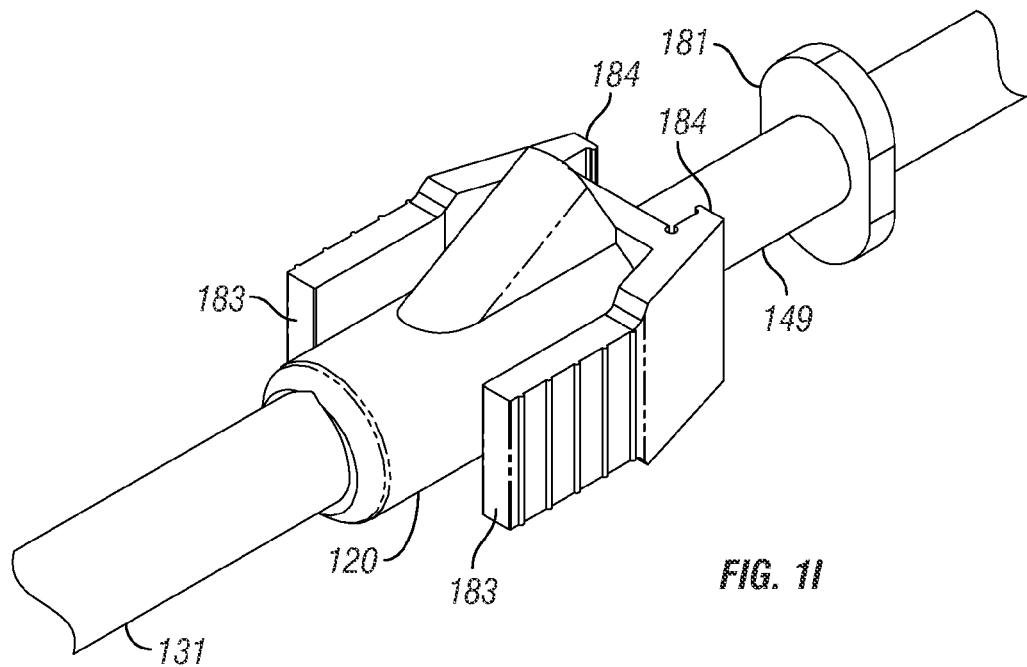
Figure 1J:
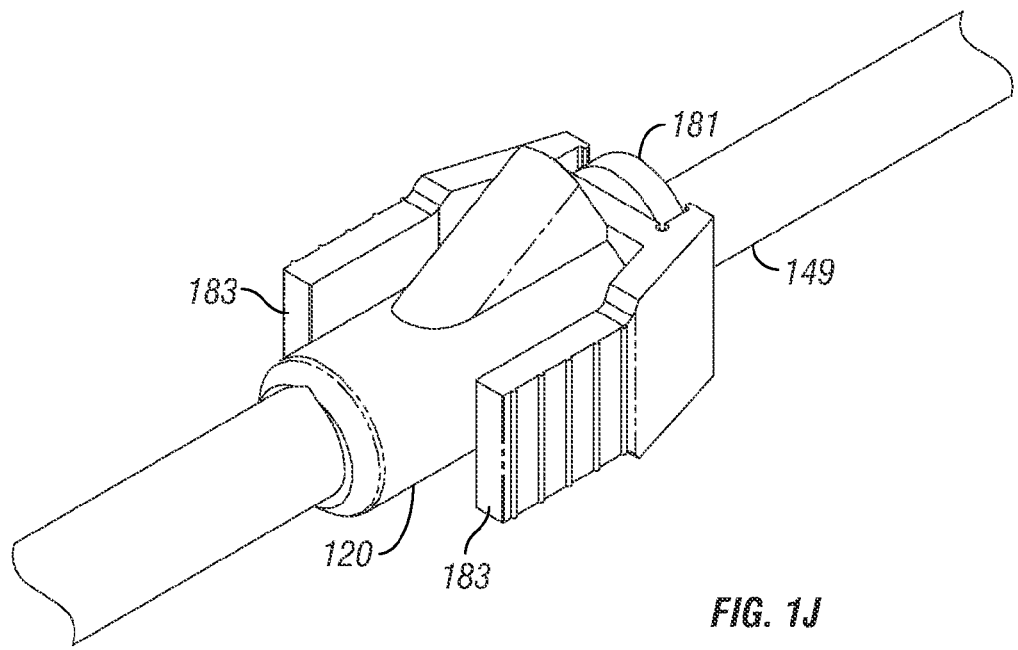

Referring now to FIGS. 1H-1J, detailed views of an exemplary embodiment of coupling member 120 and shaft portion 149 are provided. In this embodiment, coupling member 120 comprises an aperture 182 configured to receive conduit 140. Coupling member 120 also comprises a pair of latch members 184 that can engage and retain a flange member 181 on shaft portion 149. Latch members 184 may be opened by gripping leverage members 183 and deflecting leverage members 183 toward the central portion of coupling member 120 (e.g., squeezing leverage members 183 toward each other). FIGS. 1H and 1I show flange member 181 separated from latch members 184, while FIG. 1J shows flange member 181 engaged with latch members 184. Therapeutic assembly 160 (shown in FIG. 1E) can be removed from shaft portion 149 by squeezing leverage members 183 toward each other and pulling coupling member toward distal end 153.

Exemplary Methods of Use

Figure 2A:
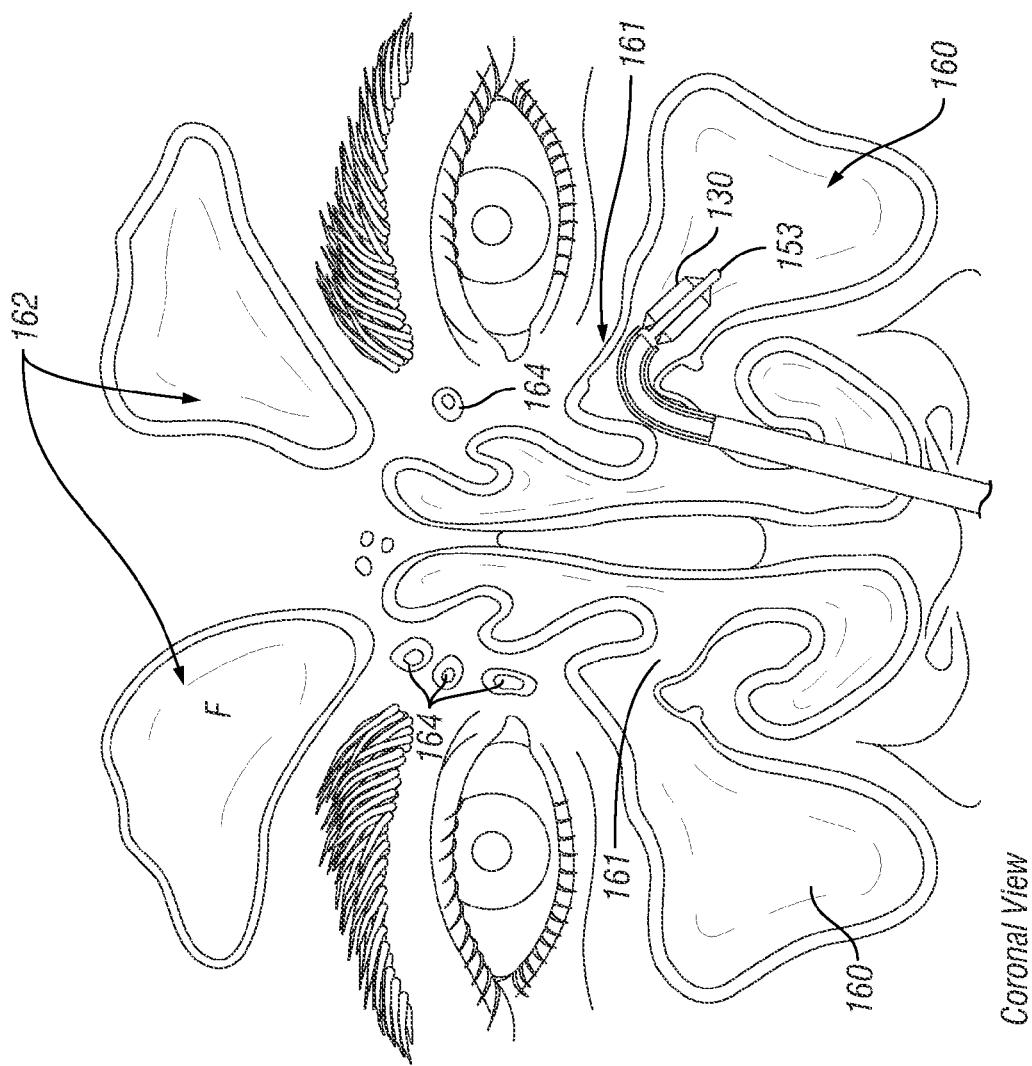
FIG. 2A illustrates a front view of paranasal sinuses with a therapeutic component inserted into one of the sinuses according to exemplary embodiments of the present disclosure.

Referring now to FIG. 2A-2K, views of therapeutic component 130 are shown during use. FIG. 2A illustrates a front view of paranasal sinuses and ostia including maxillary sinuses 160, maxillary ostia 161, frontal sinus 162 and ethmoid sinuses 164. In the embodiment shown in FIG. 2A, therapeutic component 130 has been inserted through a maxillary ostium 161 and disposed in a maxillary sinus 160 with articulated portion 143 shown in an articulated or curved position.

Figure 2B:
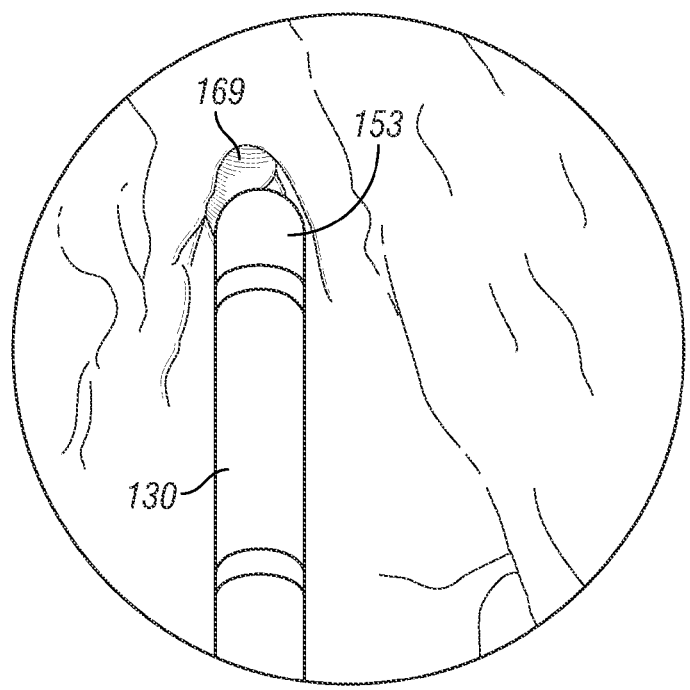
FIGS. 2B-2I illustrate perspective views of the therapeutic component of FIG. 2A being inserted into and removed from a paranasal sinus.
Figure 2C:
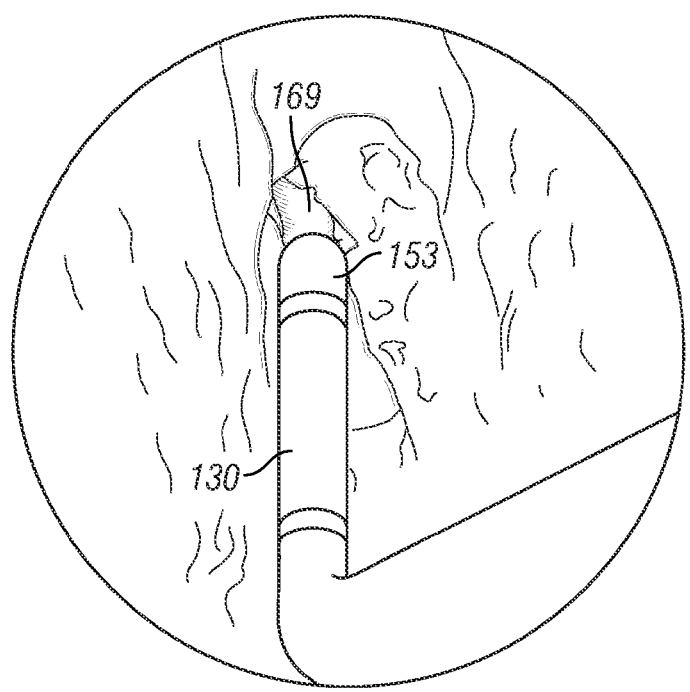
Figure 2D:
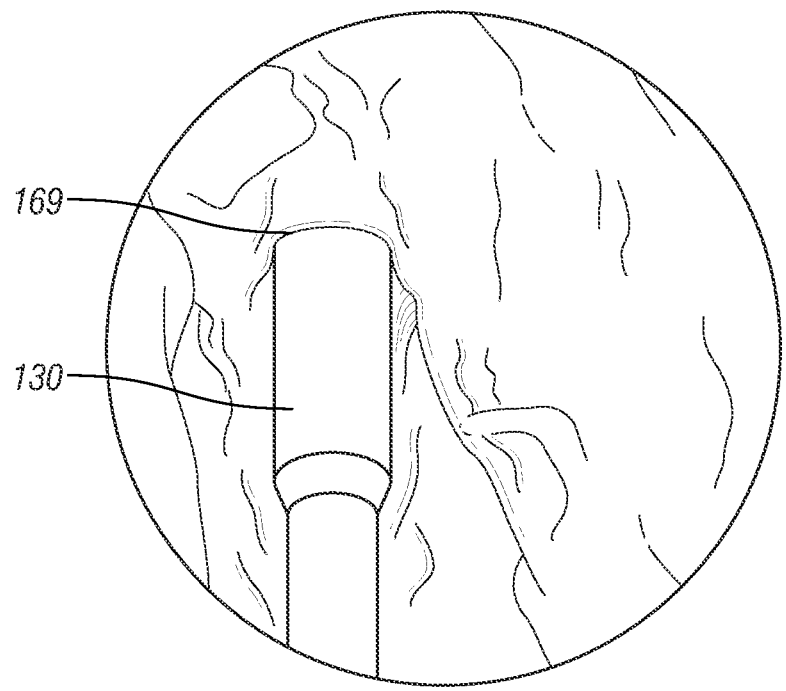
Figure 2E:
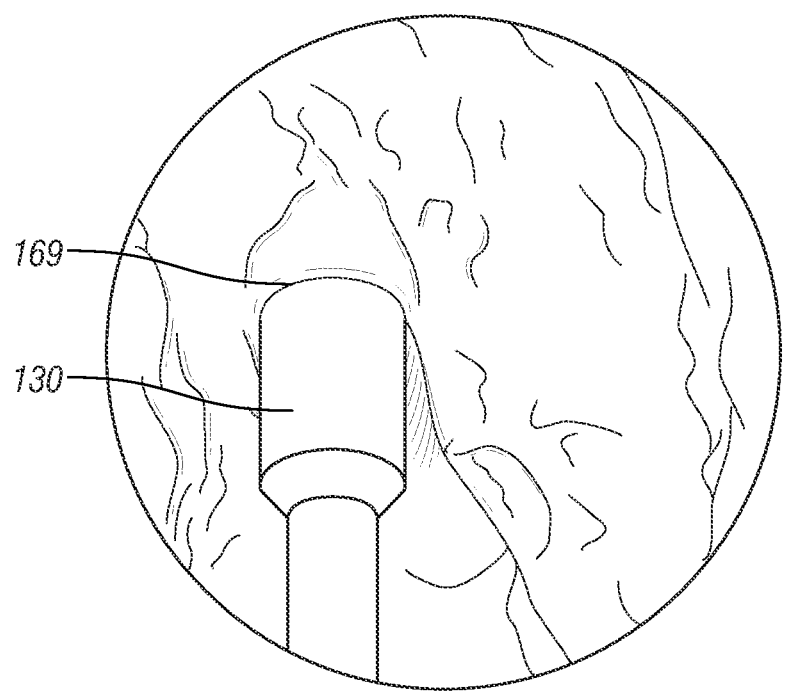
Figure 2F:
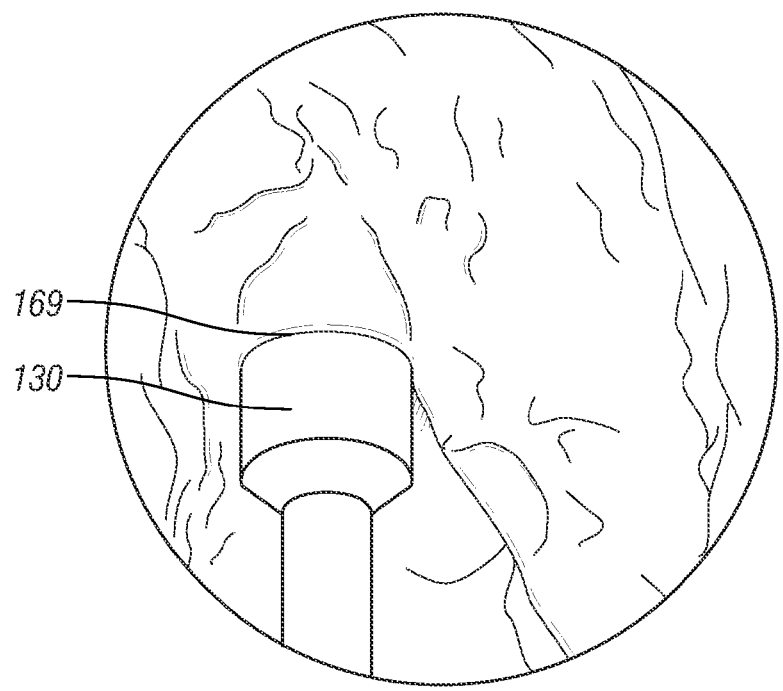
Figure 2G:
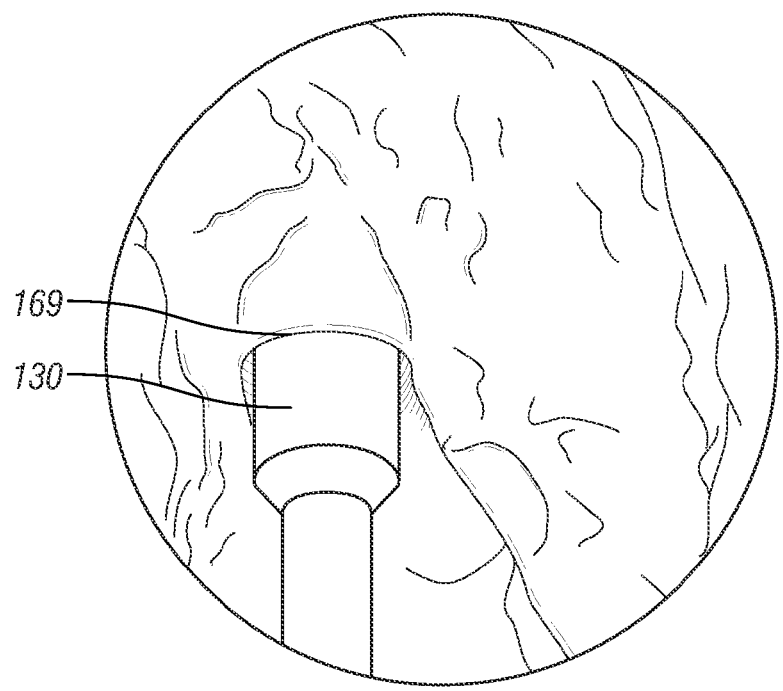
Figure 2H:
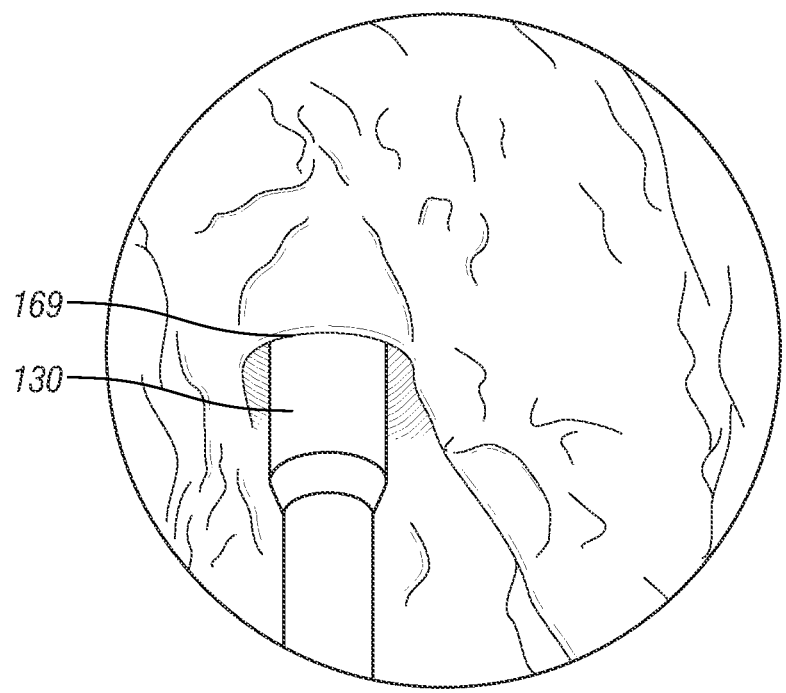
Figure 2I:
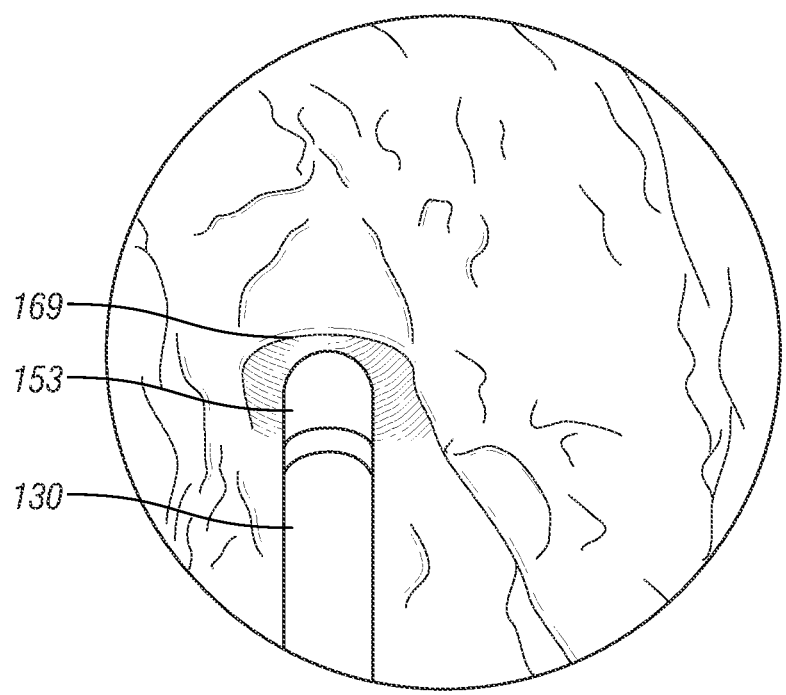

Referring now to FIGS. 2B-2G, detailed views are provided of therapeutic component 130 being inserted into a paranasal ostium 169 and expanded. In FIGS. 2B and 2C, therapeutic component 130 (in a non-expanded condition) and distal end 153 are approaching paranasal ostium 169. As shown in FIG. 2C, articulating portion 143 has been articulated to direct therapeutic component 130 towards paranasal ostium 169. In FIG. 2D, therapeutic component 130 has entered paranasal ostium 169 and has been partially expanded. In FIGS. 2E and 2F, therapeutic component 130 is further expanded, thereby enlarging paranasal ostium 169. In FIGS. 2H and 2I, therapeutic component 130 is reduced in size and withdrawn from paranasal ostium 169. In certain embodiments, therapeutic component can be reduced in size by opening a valve on coupling member 141 (shown in FIGS. 1A-1B) to release fluid pressure supplied to therapeutic component 130. FIG. 2J illustrates paranasal ostium 169 prior to the insertion and expansion of therapeutic component 130. FIG. 2K illustrates an enlarged paranasal ostium 169 after the insertion, expansion and withdrawal of therapeutic component 130.

In exemplary embodiments, articulating portion 143 is configured so that it retains its shape when a force is exerted on distal end 153 or therapeutic component 130 during use. For example, articulating portion 143 can be articulated or curved and therapeutic component 130 directed through the paranasal ostium 169, as shown in FIG. 2C. In certain instances, distal end 153 may be used to penetrate scar or granulation tissue in paranasal ostium 169 as distal end 153 enters the opening.

A surgeon implementing insertion device 150 to insert therapeutic component 130 into a paranasal ostium 169 may do so by using direct visualization. This can allow the surgeon to use positioning member 147 to manipulate articulating portion 143 as needed during the insertion procedure. The ability of articulating portion 143 to retain its shape when subjected to external forces allows distal end 153 to penetrate through openings that may offer resistance to the advancement of therapeutic component 130. This ability also allows therapeutic component 130 to be inserted into regions that may offer resistance without the use of a guide wire or cannula (e.g. a flexible wire or tube that does not lock into a rigid position and is used to guide a therapeutic component). In certain embodiments, articulating portion 143 can retain its shape when distal end 153 is subjected to external radial or axial forces of approximately 0.1, 0.2, 0.3, 0.4, 0.5, 0.6, 0.7, 0.8, 0.9 or 1.0 pounds.

In certain portions of the anatomy, e.g. the cardiovascular system, a therapeutic component may be guided by anatomical features such as blood vessels. In the case of paranasal sinuses and ostia, however, the anatomical features do not generally provide such guidance. It is therefore desirable to provide a rigid or firm structure that can be used to assist in guidance of a therapeutic component. The ability to use direct visualization, combined with the articulating and position-retaining features of insertion device 150, can allow a surgeon to successfully insert therapeutic component 130 into a paranasal ostium or sinus without an external guide apparatus. In addition, the ability to insert a therapeutic component without the use of an external guide apparatus, e.g. a guide wire or cannula, can reduce the number of components that must be disposed of or sterilized, and in turn, reduce costs associated with the procedure.

Stent Deployment Embodiments

Figure 3A:
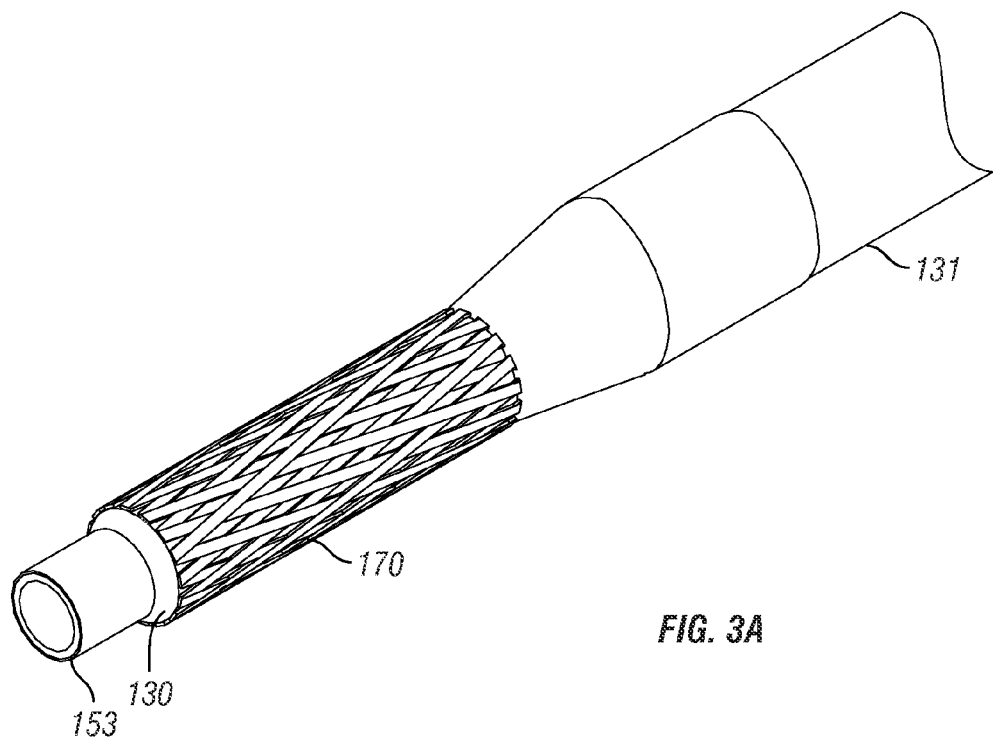
FIGS. 3A-3D illustrate perspective and side views of a stent disposed on the therapeutic component of FIGS. 1A-1C.
Figure 3B:
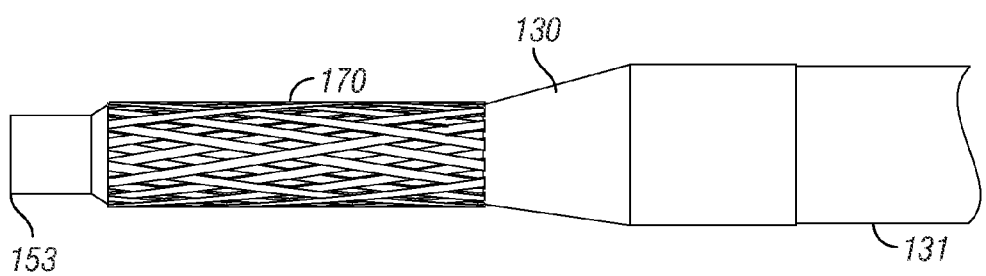
Figure 3C:
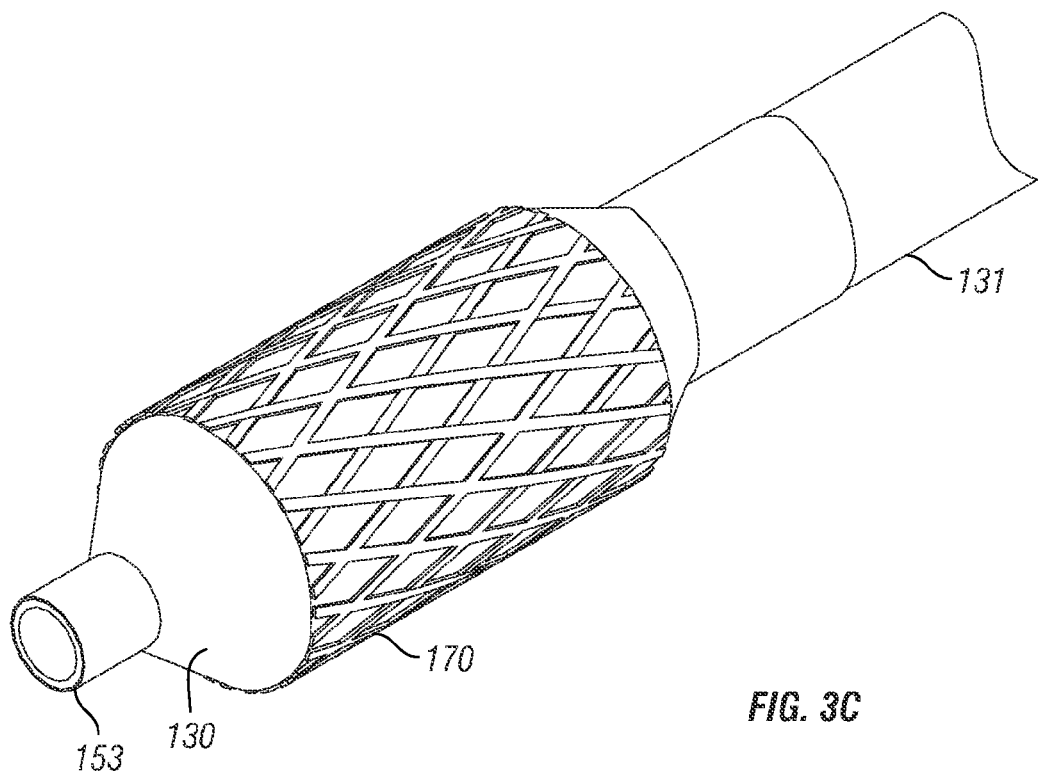
Figure 3D:
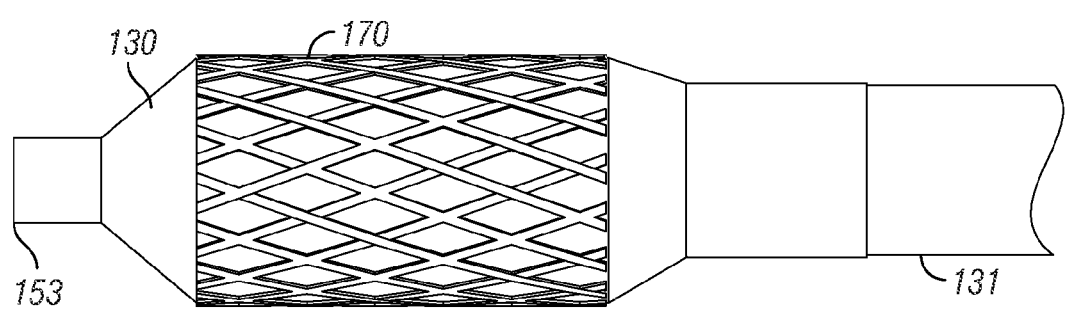

In certain embodiments, therapeutic component 130 may be used to deploy a stent or other device into a paranasal sinus ostium. Referring to FIGS. 3A-D, perspective and side views are shown of a stent 170 disposed on therapeutic component 130. In FIGS. 3A-B, stent 170 and therapeutic component 130 are not expanded, while in FIGS. 3C-D, stent 170 and therapeutic component 130 have been expanded. In certain embodiments, therapeutic component 130 and stent 170 can be inserted into a paranasal sinus ostium in the un-expanded configuration shown in FIGS. 3A-B and then expanded to the configuration shown in FIGS. 3C-D. Therapeutic component 130 can then be returned to the un-expanded configuration and removed from the paranasal sinus ostium, while stent 170 remains in the paranasal ostium.

Exemplary embodiments may deploy stents disclosed in U.S. Patent Publication No. 2006/0136041 (published Jun. 22, 2006), entitled "Slide-and-Lock Stent," and incorporated by reference herein. In certain embodiments, the stent may comprise a tubular member with longitudinal and circumferential axes. The tubular member can include at least two circumferentially adjacent modules, with each comprising at least two slide-and-lock radial elements that are separated from one another in the longitudinal axis by at least one passive radial element. In particular embodiments, each slide-and-lock radial element can include an engaging tab and a receiving slot which includes a lockout tooth and defines a travel path. In certain embodiments, the engaging tabs of each module are slidably engaged within receiving slots in the slide-and-lock radial elements from a circumferentially adjacent module. In particular embodiments, the lockout tooth can be configured to permit one-way sliding of the tabs along the travel path, so that the tubular member achieves expansion in the circumferential axis with reduced recoil as the circumferentially adjacent modules slide apart from one another.

Additional exemplary embodiments may deploy stents disclosed in U.S. Pat. Nos. 5,549,662; 5,733,328; 5,421,955; 5,441,515; 5,618,299; 5,443,500; 5,649,977; 5,643,314; 5,735,872; 4,733,665; 4,740,207; 4,877,030; 5,007,926; 5,059,211; 4,954,126; and 5,192,307, each of which are incorporated by reference herein.

Additional exemplary embodiments may include stents as disclosed in Balcon et al., "Recommendations on Stent Manufacture, Implantation and Utilization," European Heart Journal (1997), vol. 18, pages 1536-1547, and Phillips, et al., "The Stenter's Notebook," Physician's Press (1998), Birmingham, Mich., each of which are incorporated by reference herein.

Mechanical Dilator Embodiments

In certain embodiments, a therapeutic component delivered to a paranasal ostium may also comprise a mechanical dilator. In particular embodiments, an insertion device may comprise an actuation member configured to mechanically expand or dilate a distal portion of a therapeutic component. Referring now to FIGS. 4A-4D, a therapeutic component 1530 is coupled to an insertion device 1550. In this embodiment, therapeutic component 1530 comprises an outer sleeve 1531 that includes a distal end 1535 and a plurality of longitudinal segments 1532. In the embodiment shown, longitudinal segments 1532 are biased towards each other (e.g., toward the central longitudinal axis of therapeutic component 1530). In this embodiment, therapeutic component 1530 further comprises a piston 1533 disposed on an inner shaft 1534.

Figures 4A, 4B:
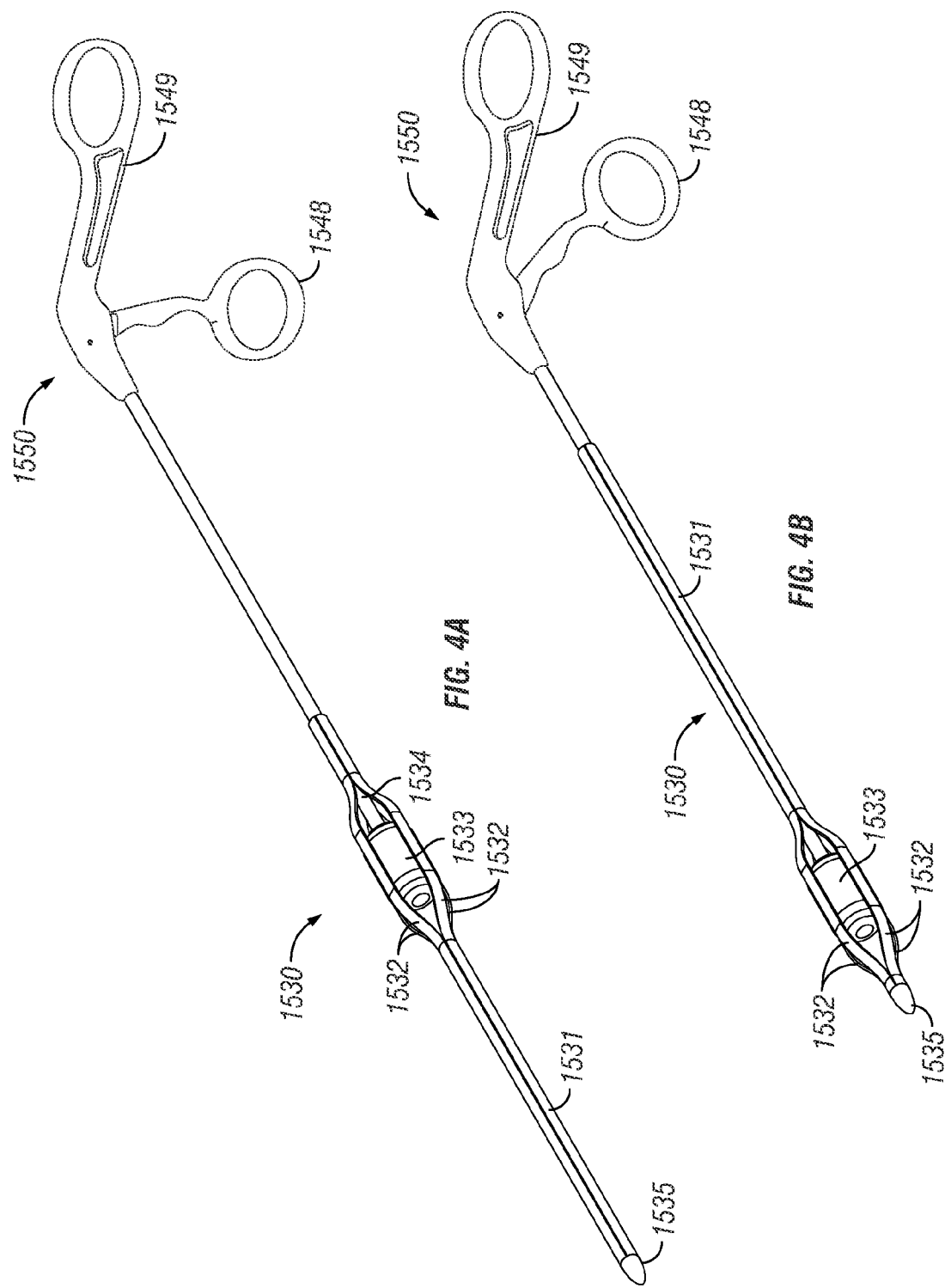

In the embodiment shown, insertion device 1550 comprises a handle portion 1549 and an actuation member 1548, e.g., a trigger, lever, or other member configured to advance piston 1533 and inner shaft 1534 towards distal end 1535. As piston 1533 is advanced, longitudinal segments 1532 are spread apart or dilated (e.g., moved away from each other and from the central longitudinal axis of therapeutic component 1530) by piston 1533. As shown in FIGS. 4B and 4D, piston 1533 can be advanced to an area near distal end 1535, and longitudinal segments 1532 dilated. During use, distal end 1535 can be inserted into a paranasal ostium with piston 1533 retracted into the position shown in FIGS. 4A and 4C. Piston 1533 can then be advanced to the position shown in FIGS. 4B and 4D so that the paranasal ostium is dilated. In certain embodiments, longitudinal segments 1532 are substantially rigid and can be configured to cut tissue as they expand outwardly. Actuation member 1548 (and piston 1533) can then be returned to the position shown in FIGS. 4A and 4C so that therapeutic component 1530 can be withdrawn from the paranasal sinus ostium.

In other embodiments, a therapeutic component may comprise other configurations. Referring now to FIGS. 5A-D, a therapeutic component 1630 comprises an outer sleeve 1634 surrounding a plurality of wires or longitudinal segments 1631 that are biased outwardly (e.g. away from the longitudinal axis of therapeutic component 1630) near a distal end 1635. Therapeutic component 1630 may be coupled to an insertion device (not shown) similar to insertion device 1550 in the previously-described embodiment. The actuating member of the insertion device may be actuated to move outer sleeve 1634 towards and away from distal end 1635. Therapeutic component 1630 may be inserted into a paranasal ostium with outer sleeve 1634 in the position shown in FIGS. 5A and 5C. The actuating member of the insertion device can then be actuated so that outer sleeve 1634 is moved to the position shown in FIGS. 5B and 5D. Longitudinal segments 1631 may then expand outwardly and dilate the paranasal sinus ostium. In certain embodiments, longitudinal segments 1631 are substantially rigid and can be configured to cut tissue as they expand outwardly. The actuating member can then be returned to its original position and outer sleeve 1634 returned to the position shown in FIGS. 5A and 5C so that therapeutic component 1530 can be withdrawn from the paranasal sinus ostium.

Referring now to FIGS. 6A-6D, a therapeutic component 1730 comprises an outer sleeve 1734 disposed around an inner shaft 1733 having a distal end 1735. Therapeutic component 1730 may also be coupled to an insertion device (not shown) similar to insertion device 1550 in a previously-described embodiment. In the embodiment shown, outer sleeve comprises a proximal end 1739 and a plurality of longitudinal segments 1732 proximal to distal end 1735. As shown in FIGS. 6B and 6D, longitudinal segments 1732 are configured to expand outwardly (e.g. away from the longitudinal axis of therapeutic component 1730) when proximal end 1739 is moved towards distal end 1735. In the embodiment shown, outer sleeve 1734 also comprises a portion 1736 that does not expand outwardly when proximal end 1739 is moved towards distal end 1735.

The actuating member of the insertion device may be actuated to move proximal end 1739 towards and away from distal end 1735. Therapeutic component 1730 may be inserted into a paranasal ostium with outer sleeve 1734 in the position shown in FIGS. 6A and 6C. The actuating member of the insertion device can then be actuated so that outer sleeve 1734 is moved to the position shown in FIGS. 6B and 6D. Longitudinal segments 1732 may then expand outwardly and dilate the paranasal sinus ostium. In certain embodiments, longitudinal segments 1732 are substantially rigid and can be configured to cut tissue as they expand outwardly. The actuating member can then be returned to its original position and outer sleeve 1734 returned to the position shown in FIGS. 6A and 6C so that therapeutic component 1730 can be withdrawn from the paranasal sinus ostium.

Referring now to FIGS. 7A-7B, a therapeutic component 1830 comprises an outer sleeve 1834 (with a distal end 1835) disposed around an inner shaft 1833. Therapeutic component 1830 may also comprise a pair of pivot members 1832 configured to pivot around a pivot point 1837 proximal to distal end 1835. Therapeutic component 1830 may also be coupled to an insertion device (not shown) similar to insertion device 1550 in a previously-described embodiment. The actuation member of the insertion device may be actuated to move inner shaft 1833 from the position shown in FIG. 7A to the position shown in FIG. 7B. In the embodiment shown, inner shaft 1833 engages pivot members 1832 and pivots them from the closed position shown in FIG. 7A to the open position shown in FIG. 7B.

Therapeutic component 1830 may be inserted into a paranasal ostium with pivot members 1832 in the position shown in FIG. 7A. The actuating member of the insertion device can then be actuated so that inner shaft 1833 is moved to the position shown in FIG. 7D. Pivot members 1832 may then pivot outwardly and dilate the paranasal sinus ostium. The actuating member can then be returned to its original position and inner shaft 1833 returned to the position shown in FIG. 7A so that therapeutic component 1830 can be withdrawn from the paranasal sinus ostium.

Referring now to FIGS. 8A-8B, a therapeutic component 1930 comprises an outer sleeve 1934 with an expandable portion 1932 near a distal end 1935. In this embodiment, a flexible inner member 1933 is disposed within outer sleeve 1934. Therapeutic component 1930 may be coupled to an insertion device (not shown) similar to insertion device 1550 in the previously-described embodiment. The actuating member of the insertion device may be actuated to move flexible inner member 1933 towards and away from distal end 1935. Therapeutic component 1930 may be inserted into a paranasal ostium with flexible inner member 1933 in the position shown in FIG. 8A. The actuating member of the insertion device can then be actuated so that flexible inner member 1933 is moved to the position shown in FIG. 8B and expandable portion 1932 dilates the paranasal sinus ostium. The actuating member can then be returned to its original position and flexible inner member 1933 expandable portion 1932 returned to the position shown in FIG. 8A so that therapeutic component 1930 can be withdrawn from the paranasal sinus ostium.

Referring now to FIGS. 9A-9B, a therapeutic component 2030 comprises an outer sleeve 2034 with an expandable portion 2032 near a distal end 2035. A spring member 2033 is disposed within expandable portion 2032. In this embodiment, spring member 2033 is coupled to distal end 2035 and a sliding rod 2036 disposed within outer sleeve 2034. Therapeutic component 2030 may be coupled to an insertion device (not shown) similar to insertion device 1550 in the previously-described embodiment. The actuating member of the insertion device may be actuated to move sliding rod 2036 towards and away from distal end 2035. As sliding rod 2036 is moved away from distal end 2035, spring member 2033 is withdrawn from expandable portion 2032 and stretched so that the overall diameter of spring member 2033 is reduced from D1 to D2. When spring member 2033 is reduced to diameter D2, the diameter of expandable portion 2032 is also reduced.

The actuating member of the insertion device can then be actuated so that rod 2036 and spring member 2033 are in the position shown in FIG. 9A. Therapeutic component 2030 may then be inserted into a paranasal ostium. The actuating member of the insertion device can then be released or actuated so that spring member 2033 is moved to the position shown in FIG. 9B and expandable portion 2032 dilates the paranasal sinus ostium. The actuating member can then be actuated so that rod 2036 and spring member 2033 are returned to the position shown in FIG. 9A. Therapeutic component 2030 can then be withdrawn from the paranasal sinus ostium.

Referring now to FIGS. 10A-10B, a therapeutic component 2130 comprises an outer sleeve 2134 with an expandable portion 2132 near a distal end 2135. In this embodiment, a plunger or piston 2136 and a compliant material 2133 are disposed within outer sleeve 2134. In certain embodiments, compliant material 2133 comprises a sponge-type foam. Therapeutic component 2130 may be coupled to an insertion device (not shown) similar to insertion device 1550 in a previously-described embodiment. The actuating member of the insertion device may be actuated to move piston 2136 towards and away from distal end 2135. Therapeutic component 2130 may be inserted into a paranasal ostium with piston 2136 and compliant material 2133 in the position shown in FIG. 10A. The actuating member of the insertion device can then be actuated so that piston 2136 and compliant material 2133 are moved to the position shown in FIG. 10B and expandable portion 2132 dilates the paranasal sinus ostium. The actuating member can then be returned to its original position and piston 2136 and compliant material 2133 returned to the position shown in FIG. 10A so that therapeutic component 2130 can be withdrawn from the paranasal sinus ostium.

Other exemplary embodiments of the present disclosure may comprise different configurations of components. For example, the insertion device, therapeutic component, or therapeutic assembly may comprise a different configuration or provide different functionality.

External Conduit Embodiments

Referring now to FIGS. 11A-11F, an exemplary embodiment comprises an insertion device 1150 coupled to a therapeutic component 1130. In this embodiment, insertion device 1150 comprises a conduit 1140 that is externally coupled to a shaft portion 1149 of insertion device 1150. In this embodiment, insertion device 1150 also comprises a handle portion 1146, and shaft portion 1149 further comprises an articulating portion 1143. Insertion device also comprises a positioning member 1147 configured to articulate articulating portion 1143 and a locking member 1148 configured to lock positioning member 1147 (and articulating portion 1143) into a desired location. A biasing member (not visible in the figures) can bias positioning member 1147 toward engagement with locking member 1148. In certain embodiments, locking member 1148 may comprise a pin that extends from handle portion 1146 and into one of a plurality of apertures or recesses 1144 (visible in FIG. 1B) in positioning member 1147. As explained in more detail below, positioning member 1147 can be manipulated to move articulating portion 1143 and therapeutic member 1130 into a desired position. In addition, the engagement of locking member 1148 and a recess 1144 can hold articulating portion 1143 and therapeutic member 1130 in the desired position.

In the particular embodiment shown, positioning member 1147 can be lifted away from locking member 1148 and pivoted about pivot member 1142. As positioning member 1147 is manipulated by the user, articulating portion 1143 is also articulated. When the desired amount of articulation is achieved, the user can release positioning member 1147 so that locking member 1148 engages one of apertures 1144 in positioning member 1147. Locking member 1148 can retain positioning member 1147 and articulating portion 1143 in the desired position. Further details of the actuation of an exemplary positioning member is provided in the discussion of FIGS. 6-9.

Figure 11A:
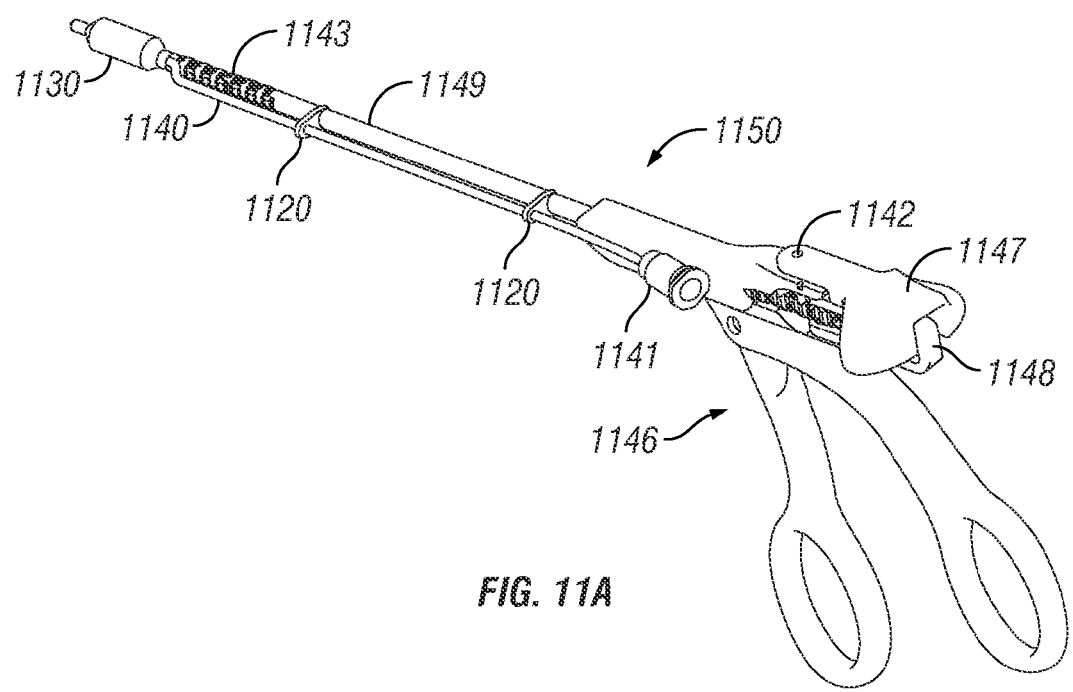
FIG. 11A illustrates a perspective view of an insertion device and a therapeutic component according to exemplary embodiments of the present disclosure.
Figure 11B:
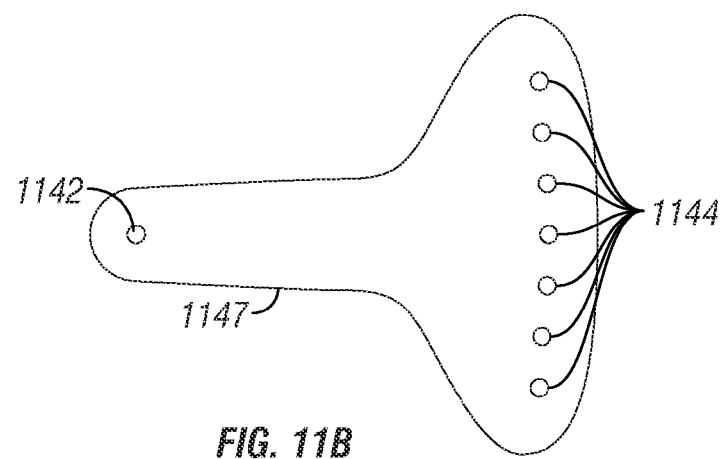
FIG. 11B illustrates an orthogonal view of a positioning member of the insertion device of FIG. 11A.
Figure 11C:
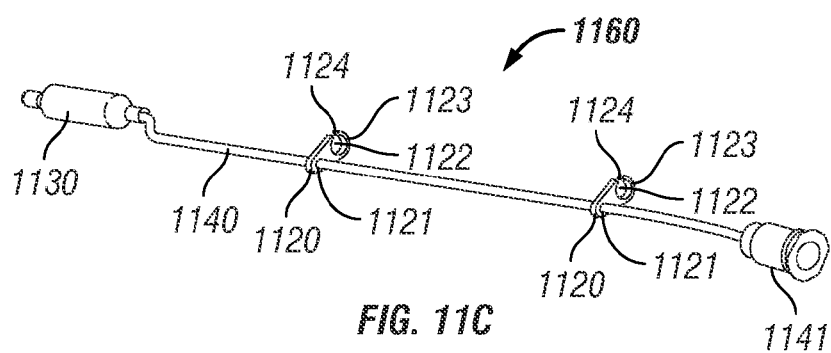
FIG. 11C illustrates a perspective view of the therapeutic component of FIG. 11A.
Figure 11D:
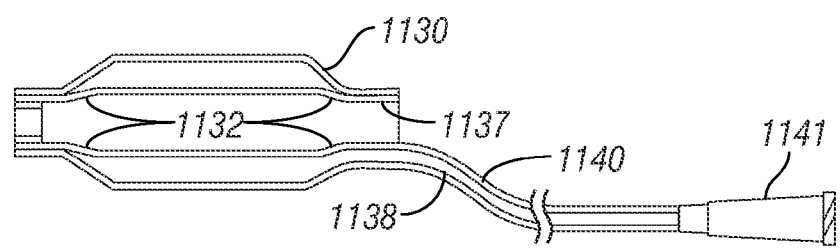
FIGS. 11D-11F illustrate section view of the therapeutic component of FIG. 11A.
Figure 11E:
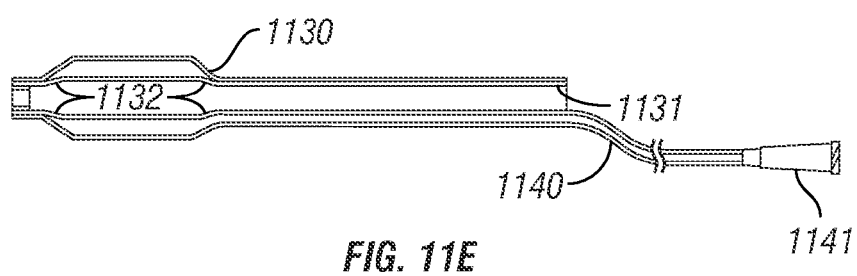
Figure 11F:
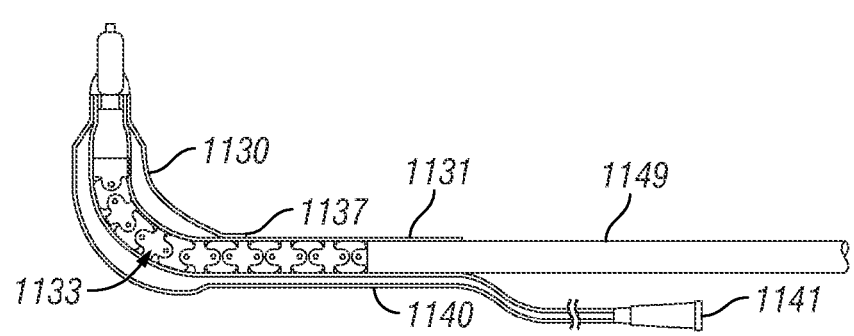

Referring now to FIGS. 11D-11F, in this embodiment, the therapeutic component 1130 is an inflatable balloon, with a first lumen 1137 configured to receive a shaft portion 1149 of insertion device 1150. Therapeutic component 1130 may also comprise a second lumen 1138 in fluid communication with conduit 1140 and a coupling member 1141 configured to couple to a pressurizing member (not shown). In certain embodiments, the pressurizing member may be a syringe filled with saline. When therapeutic component 1130 is positioned in a target anatomy (e.g., a paranasal sinus such as a maxillary or frontal sinus), the pressurizing member can apply fluid pressure to the balloon 1130 via conduit 1140 and lumen 1138.

A more detailed view of therapeutic component 1130 is provided in FIGS. 11D and 11E. In certain embodiments, therapeutic component 1130 may be bonded to form first lumen 1137 at one end of therapeutic component 1130. In particular embodiments, therapeutic component 1130 may comprise nylon, polyethylene, polyurethane, Pebax, polyethylene terephthalate, or a blend of one or more of these polymers. In certain embodiments, first lumen 1137 may comprise one or more tapered portions 1132 configured to engage an insertion device and help retain therapeutic component 1130 on shaft portion 1149 of insertion device 1150. In certain embodiments therapeutic component 1130 may be coupled to an insertion device comprising a rigid shaft, while in other embodiments therapeutic component 1130 may be coupled to an articulating shaft. The embodiment shown in FIG. 11E is configured similar to the embodiment shown in FIG. 11D, but also comprises a sleeve or extended portion 1131 configured to cover a portion of an insertion device.

As shown in FIG. 11F, in particular embodiments, extended portion 1131 may extend over articulating segments 1133 of articulating portion 1143 of insertion device 1150. Insertion device 1150 may also be bent or formed in one of several pre-set configurations. In specific embodiments, insertion device 1150 may comprise one or more channels for suction, irrigation or flushing of a sinus. In particular embodiments, insertion device 1150 may comprise one or more channels configured to receive a scope. In such embodiments, the minimum radius of the articulating portion should be compatible with the bending requirements of the scope.

In certain embodiments, therapeutic component 1130 may be a separate component from the insertion device, while in other embodiments, therapeutic component 1130 may be integral an insertion device. Certain embodiments may also comprise a tether (e.g., a wire, thread, or cable) between the insertion device and therapeutic component 1130 to allow for retrieval of the therapeutic component in the event the therapeutic component becomes separated from the insertion device. In addition, conduit 1140 is shown in this embodiment to be external to first lumen 1137, but in other embodiments, conduit 1140 may be located internally within first lumen 1137.

During operation, a pressurizing member fluidly connected to conduit 1140 via coupling member 1141 can be manipulated to pressurize therapeutic component 1130, thereby causing therapeutic component 1130 to expand radially outward. In certain embodiments, the pressurizing member may comprise a syringe or balloon inflation device, and may pressurize conduit 1140 and therapeutic component 1130 via a fluid such as saline solution. Particular embodiments of the balloon inflation device may also comprise a pressure measurement device to indicate balloon inflation pressure.

Referring back now to FIGS. 11A and 11C, an exemplary embodiment of a therapeutic assembly 1160 is shown comprising coupling members 1120 (e.g., clips) coupled to conduit 1140. In this embodiment, coupling members 1120 are configured to couple to shaft portion 1149 of insertion device 1150. Each coupling member 1120 comprises a first aperture 1121 through which conduit 1140 extends, and a second aperture 1122 through which shaft portion 1149 can extend. It is understood that first and second apertures 1121, 1122 may not be completely surrounded or circumscribed by material of coupling member 1120. For example, coupling member 1120 may comprise an end portion 1123 that partially surrounds second aperture 1122 and is separated from the body portion of coupling member 1120 by a break or gap 1124 in the material. This can allow end portion 1123 to be flexed away from the body portion of coupling member 1120 in order to receive shaft portion 1149.

Release Actuation Embodiments

Referring now to FIGS. 12A-12G, another exemplary embodiment comprises an insertion device 240 having a mating receptacle 241 proximal to a first end 242 of insertion device 240. In the embodiment shown, mating receptacle 241 comprises one or more slots 243 with an angled end portion 244 configured to engage a similarly angled portion 222 of coupling member 220. Mating receptacle 241 may also comprise a retaining mechanism 245 (e.g., a spring-loaded detent or other suitable device) to firmly grasp and release coupling member 220 as needed, e.g. during an installation or removal procedure.

Referring specifically now to FIGS. 12A-12E, side and top views are shown of insertion device 240 in various positions. As shown in the side view of FIG. 12A, insertion device 240 comprises a handle portion 246 and a shaft portion 249 extending from handle portion 246. In the embodiment shown, shaft portion 249 comprises one or more articulating segments 250 proximal to first end 242 of shaft portion 249. In certain embodiments, articulating segments 250 can enable first end 242 of shaft portion 249 to be positioned and locked in a specific angular position as desired by the user.

Insertion device 240 may also comprise a positioning member 247 (e.g., a lever) that can be manipulated to position articulating segments 250 and mating receptacle 241. As shown in the top view of FIG. 12C, when positioning member 247 is aligned with shaft portion 249, articulating segments 250 remain collinear (e.g., in a straight position) with shaft portion 249. As shown in FIG. 12D, when positioning member 247 is moved in the direction of arrow 252, articulating segments 250 and mating receptacle 241 are moved in the direction of arrow 251. Similarly, as shown in FIG. 12E, when positioning member 247 is moved in the direction of arrow 254, articulating segments 250 and mating receptacle 241 are moved in the direction of arrow 253. Also visible in FIGS. 12F-12G are a plurality of recesses or apertures 257 configured to engage a locking member 277 (visible in FIG. 12B) to hold positioning member 247 in a desired position. Insertion device 240 may also comprise a biasing member (not visible in the figures) configured to bias positioning member 247 so that locking member 277 is normally engaged with an aperture 257. A user may overcome the biasing member force by pushing up on positioning member 247 (e.g., pushing the end of positioning member that is distal to mating receptacle 241 in a direction away from handle portion 246). It is understood that FIGS. 12C-12E illustrate only a few of the many positions in which positioning member 247, articulating segments 250 and mating receptacle 241 may be placed.

Figure 12A:
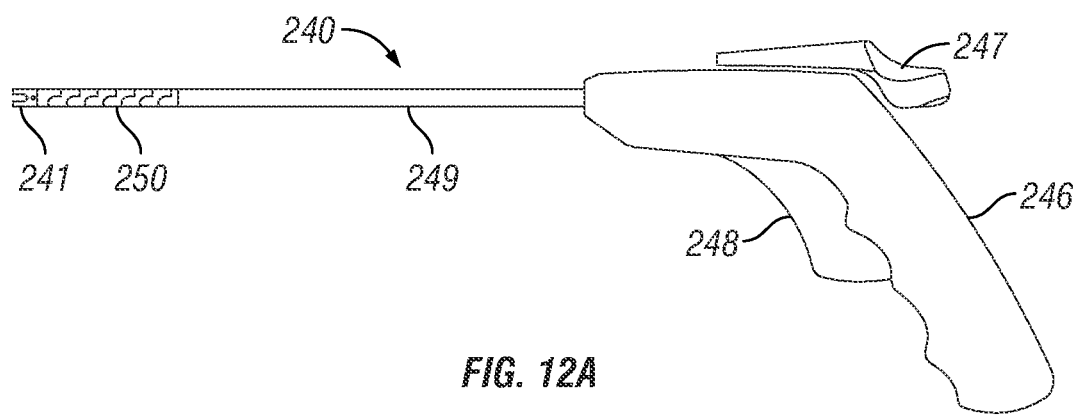
FIG. 12A illustrates a side view of an insertion device according to exemplary embodiments of the present disclosure.
Figure 12B:
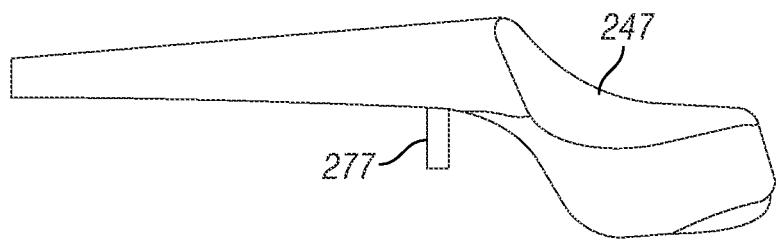
FIG. 12B illustrates a side view of the positioning member of the insertion device of FIG. 12A.
Figure 12C:
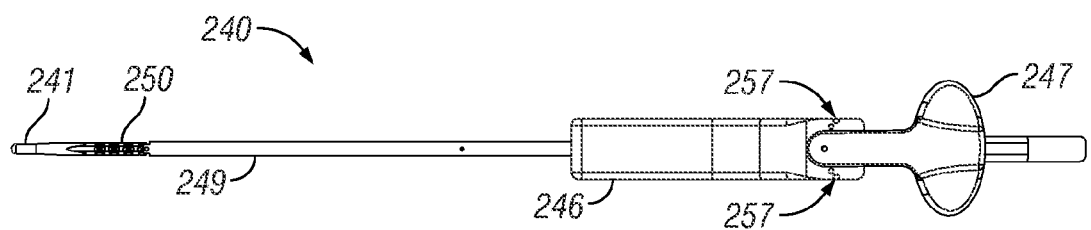
FIGS. 12C-12E illustrate orthogonal views of the insertion device of FIG. 12A according to exemplary embodiments of the present disclosure.
Figure 12D:
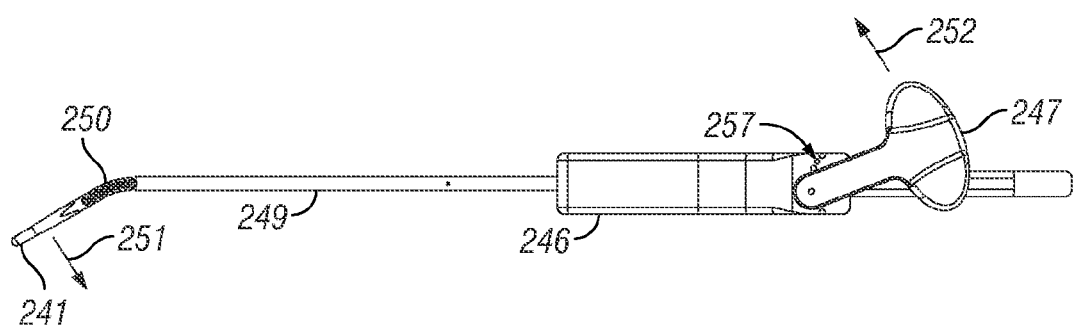
Figure 12E:
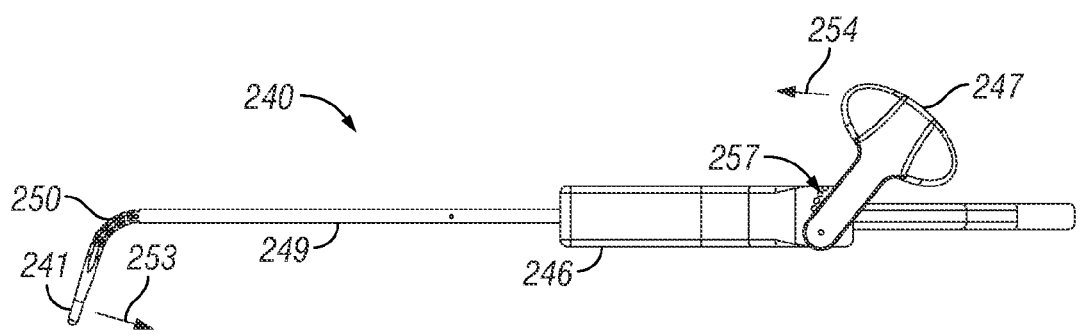
Figure 12F:
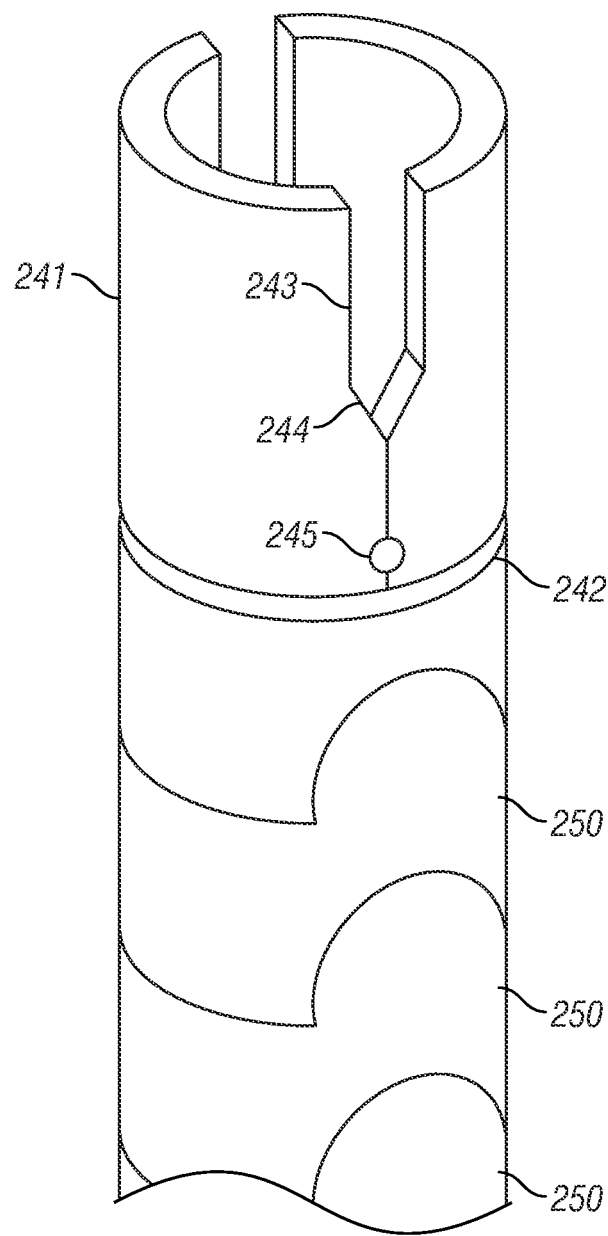
FIG. 12F illustrates a detailed perspective view of the insertion device of FIG. 12A.
Figure 12G:
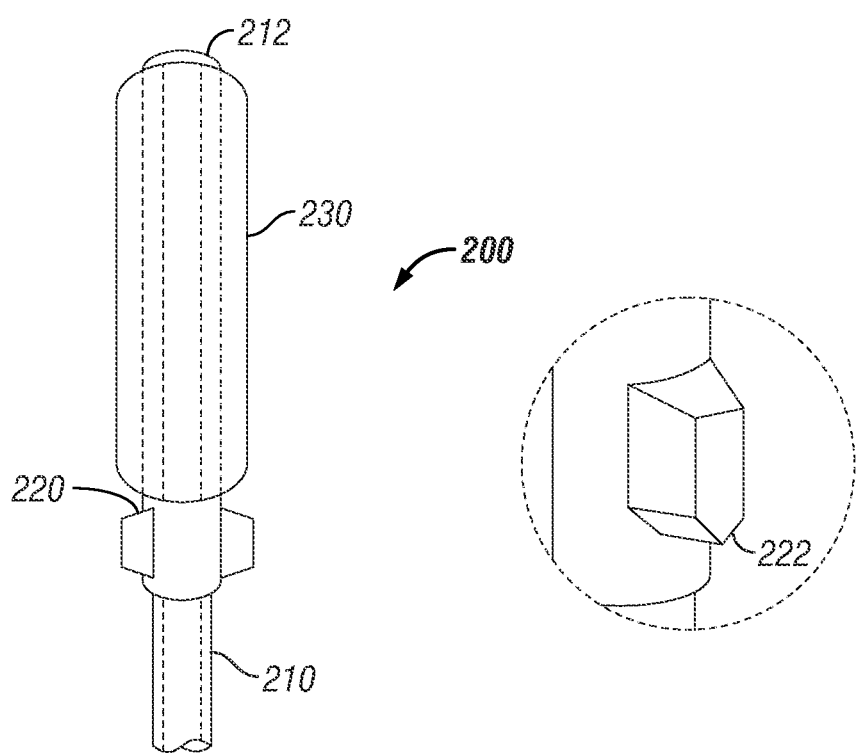
FIG. 12G illustrates a perspective view of a therapeutic component configured for use with the insertion device of FIG. 12A.

As shown in the side view of FIG. 12A, insertion device 240 may also comprise a release actuator 248. In this embodiment, release actuator 248 is configured to allow retaining member 245 to release coupling member 220 when release actuator 248 is actuated.

In certain embodiments, shaft portion 249 may have a finite number of intermediate positions/angles where insertion device 240 can be rendered rigid within tolerances acceptable to current surgical navigation protocols (e.g., +/−2.00 mm).

Referring now to FIG. 12G, an exemplary embodiment of the present disclosure comprises an elongate device 200 configured to couple to mating receptacle 241. Elongate device 200 comprises an elongate shaft 210, a coupling member 220, and a therapeutic component 230 that is proximal to a first end 212 of elongate shaft 210. In certain embodiments, coupling member 220 comprises one or more tabs, protuberances or extensions from elongate shaft 210, and therapeutic component 230 comprises an inflatable balloon. In certain embodiments, coupling member 220 may be integral to elongate shaft 210, including for example, molded into elongate shaft 210. In other embodiments, coupling member 220 may be a separate component, e.g. a collar or ring that fits around elongate shaft 210.

In specific embodiments, coupling member 220 may be molded from a plastic or other polymer material. In certain exemplary embodiments, coupling member 220 comprises rigid tabs that are positioned at a constant distance and orientation relative to first end 212 and therapeutic component 230. In specific embodiments, coupling member 220 comprises tabs with a specific geometry that enables a rigid and consistent interface or engagement with a receiving member, e.g. a mating receptacle 241 on a delivery instrument or insertion device 240 (shown in FIG. 12A). Via this mating interface, the elongate device 200 and insertion device 240 can be enabled to function as a unitary rigid instrument.

Instrument Guidance Embodiments

In certain embodiments of the present disclosure, direct visualization of the sinus ostium may not be possible. Such embodiments may utilize instrument guidance systems (IGS) with a location sensor to track the location of the therapeutic component. In specific examples, the insertion device can be calibrated prior to insertion of the therapeutic component so that the spatial relationship between the therapeutic component and a tracking component is established. In embodiments with an articulating insertion device, the spatial relationship between the therapeutic component and the tracking component can be established at one or more pre-set articulated positions of the insertion device. This can allow a user to insert the therapeutic component when the insertion device is in a first position (e.g., straight) and then be able to accurately follow the movement of the therapeutic component as the insertion device is articulated after being inserted into the sinus. Certain embodiments may also comprise "smart" IGS on articulating insertion devices, in which a tracking component on the handle portion of the device is coupled to the articulation mechanism such that it automatically adjusts according to the articulation angle. Such embodiments can allow a user to track the therapeutic component during all angles of articulation. In specific embodiments, a user may still lock the insertion device into a preset angle or multiple angles for obtaining rigidity of the instrument during positioning of the therapeutic component.

Figure 13B:
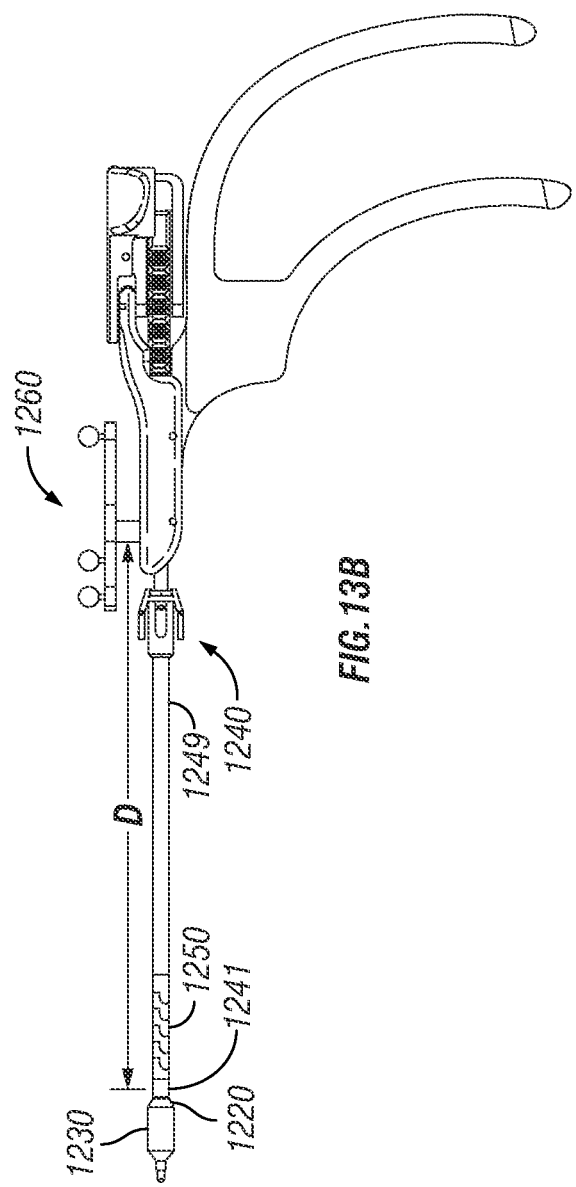
FIG. 13B illustrates a side view of an insertion device configured to insert the therapeutic component of FIG. 13A.

Referring now to FIG. 13A, a frontal ostium 1261 and frontal sinus 1262 may not be directly visualized for the insertion of a distal end of an insertion device 1240 and a therapeutic component 1230. It may therefore be beneficial to utilize a device or system configured to assist in determining the location of the distal end of the insertion device. Referring now to FIG. 13B, a side view illustrates therapeutic component 1230 coupled to insertion device 1240 via coupling member 1220, which is engaged with mating receptacle 1241. In this embodiment, a location sensor 1260 (e.g., a tracking array) may be coupled to insertion device 1240 to assist a user in determining the location of mating receptacle 1241 and therapeutic component 1230, using surgical navigation or instrument guidance system technology. In this embodiment, location sensor 1260 is located a fixed distance D from mating receptacle 1241 when articulating segments 1250 are collinear with shaft portion 1249. A user may register or calibrate the location of mating receptacle 1241 and/or therapeutic component 1230 by using conventional instrument registration protocols (e.g. surgical navigation or image guidance systems). In certain embodiments, typical, rigid universal instrument registration protocols may be employed to enable balloon tip navigation during each procedure. In other embodiments, a system of three dimensional spatial coordinates corresponding to the navigated tip can be provided to facilitate instrument specific registration protocols employed by some systems.

In specific embodiments, location of the therapeutic component 1230 with respect to the location sensor 1260 at various pre-set angles can be preset into the navigation system, and is calibrated if needed prior to insertion of the distal tip into the patient. During use, the location of therapeutic component 1230 can be displayed on pre-procedurally obtained CT scans of the patient's anatomy. In specific embodiments, the instrument can be inserted in a straight or unarticulated configuration, but closer to anatomic target structure, the instrument can be locked to one of the pre-set angles enabling the navigation system to accurately locate the therapeutic component 1230.

Figure 14A:
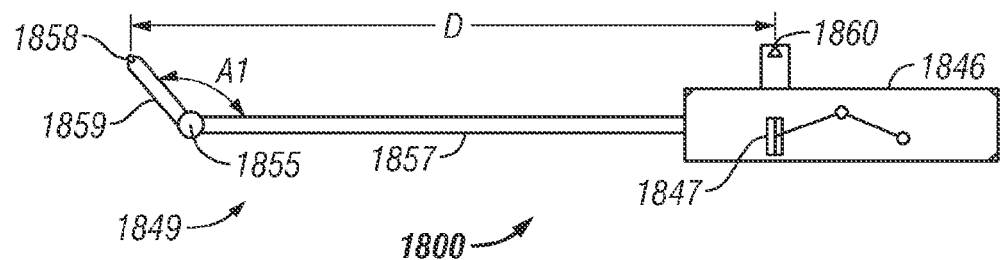
FIGS. 14A-14C illustrate side views of an insertion device according to exemplary embodiments of the present disclosure.
Figure 14B:
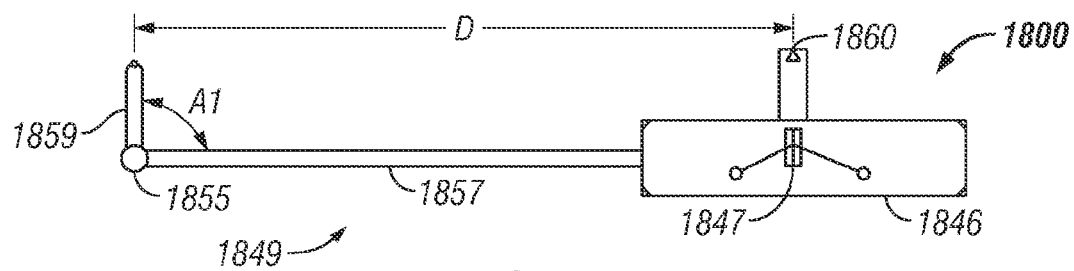
Figure 14C:
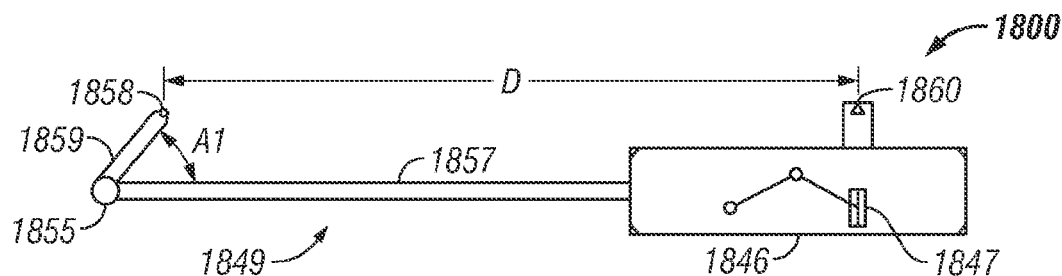

Referring now to FIGS. 14A-14C, in another exemplary embodiment an insertion device 1800 comprises a handle portion 1846 and a shaft portion 1849 and a location sensor 1860 configured to track or mimic the movement of a distal end 1858. Shaft portion 1849 further comprises a fixed portion 1857 and a rotating or pivoting portion 1859 (with distal end 1858) configured to pivot or rotate around pivot member 1855. Insertion device 1800 also comprises an actuator 1847 configured to move pivoting portion 1859. In specific embodiments, insertion device 1800 comprises an internal linkage (e.g., an actuator rod and gearing mechanism) configured to control the movement of pivoting portion 1859 by actuator 1847.

In specific embodiments, actuator 1847, location sensor 1860, and pivoting portion 1859 are coupled so that the distance D between distal end 1858 and location sensor 1860 remains constant. As shown in FIGS. 14A-14C, the distance D between distal end 1858 and location sensor 1860 remains constant regardless of the position of actuator 1847 or the angle A1 between pivoting portion 1859 and fixed portion 1857. This relationship between location sensor 1860 and distal end 1858 allows a navigation system to sense the movement of location sensor 1860 and thereby correlate an equivalent movement to distal end 1858. The position of the distal end 1858 may then be located with respect to anatomical imaging information using surgical navigation or image guidance system technology, irrespective of angle A1. This can assist a user in placing distal end 1858 (and a therapeutic component coupled to distal end 1858) when the user is not able to see distal end 1858 because it is located within an anatomical structure. This embodiment may also be applied to a multi-linked articulation version or other articulated versions of insertion device 1800. In exemplary embodiments, the location sensor 1860 can be coupled to the articulation actuator 1847 such that the distance D between the distal end 1858 and the location sensor 1860 remains constant at all positions of articulation.

Figure 14D:
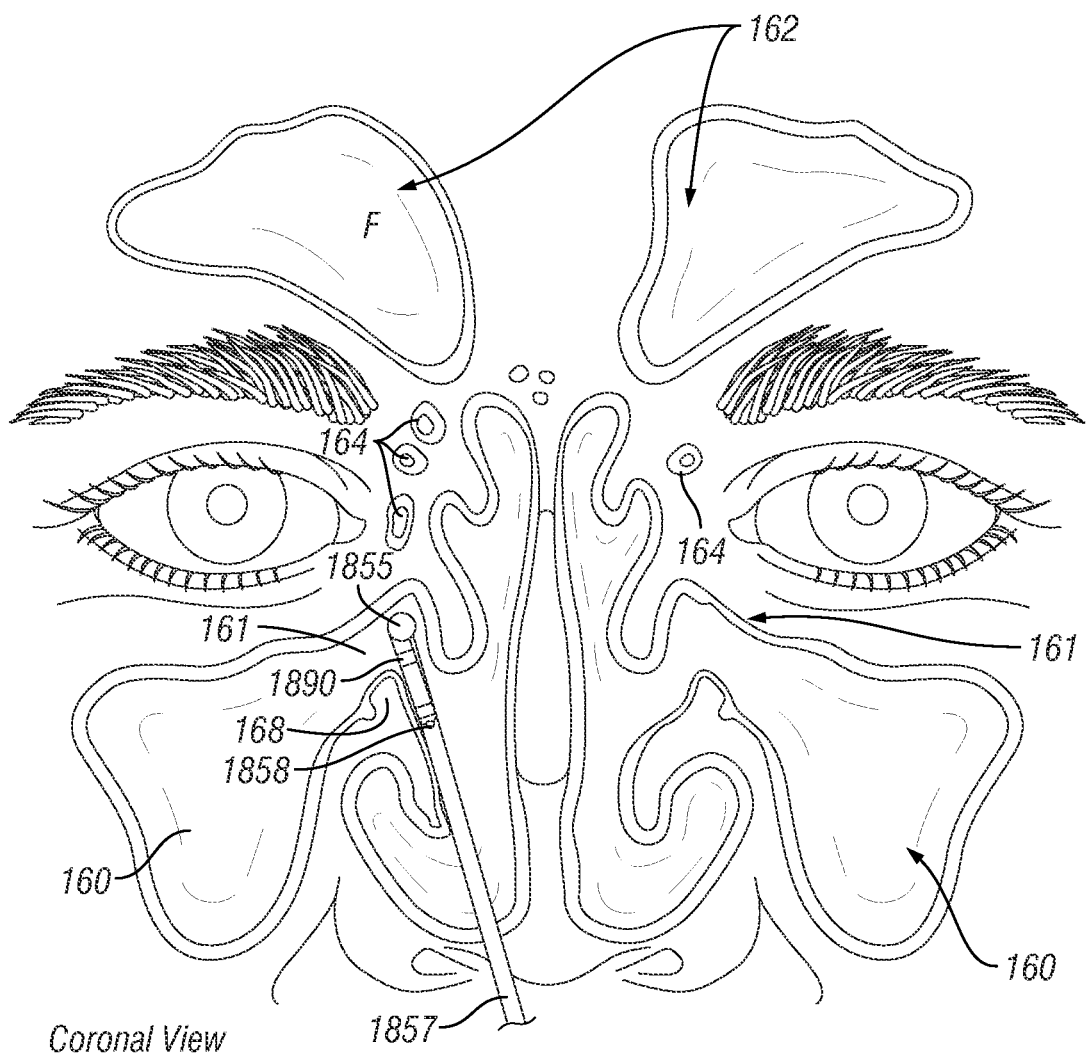
FIGS. 14D-14E illustrate a front view of paranasal sinuses with a therapeutic component inserted into one of the sinuses according to exemplary embodiments of the present disclosure.
Figure 14E:
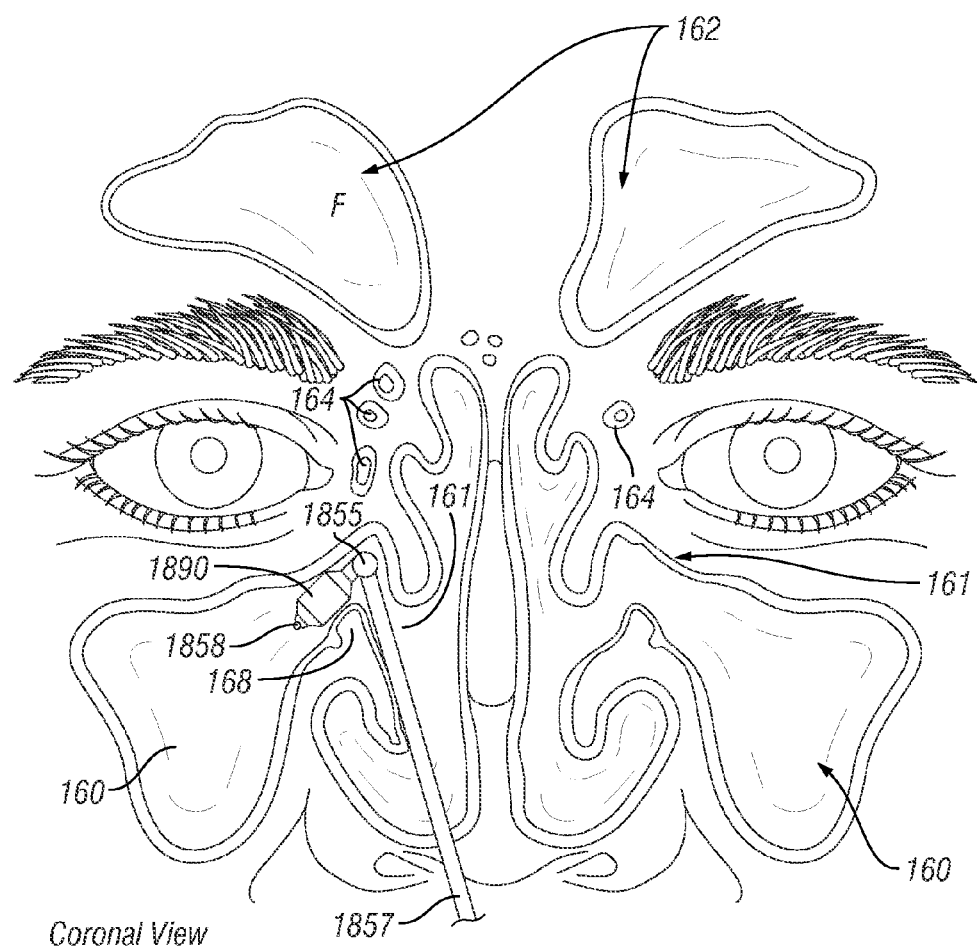
Figure 14F:
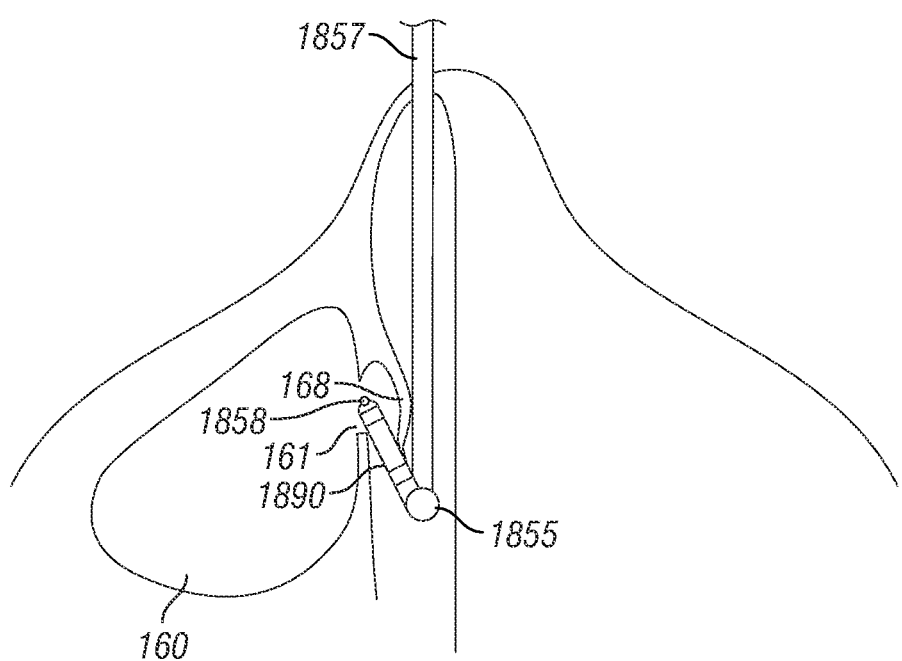
FIG. 14F illustrates an axial view of paranasal sinuses with a therapeutic component inserted into one of the sinuses according to exemplary embodiments of the present disclosure.

Referring now to FIGS. 14D-14F, views of the distal end of insertion device 1800 are shown during use. FIGS. 14D-14E illustrate a front view of paranasal sinuses and ostia including maxillary sinuses 160, maxillary ostia 161, frontal sinus 162, ethmoid sinuses 164, and an uncinate process 168. FIG. 14F illustrates an axial view of a maxillary sinus 160, maxillary ostium 161 and uncinate process 168. In this embodiment, a therapeutic component 1890 has been coupled to pivoting portion 1859. In FIG. 14D, pivoting portion 1859 is pivoted so that angle A1 is reduced and distal end 1858 is near fixed portion 1857. In this embodiments, pivot member 1855 can be inserted past uncinate process 168 as shown in FIG. 14D. Fixed portion 1857 can then be withdrawn slightly (via handle portion 1846 shown in FIGS. 14A-14C) and pivoting portion 1859 can be pivoted (e.g., via articulation actuator 1847) so that therapeutic component 1890 is directed into maxillary ostium 161, as shown in FIGS. 14E and 14F. Therapeutic component 1890 can also be expanded (e.g., via any of the methods or devices described herein) to dilate maxillary ostium 161. It is understood that in certain embodiments, insertion device 1800 may be used without a location sensor 1860. It is also understood that the rotating or pivoting features of insertion device 1800 may be combined with features of other embodiments disclosed herein.

Retention Mechanism Embodiments

Figure 15A:
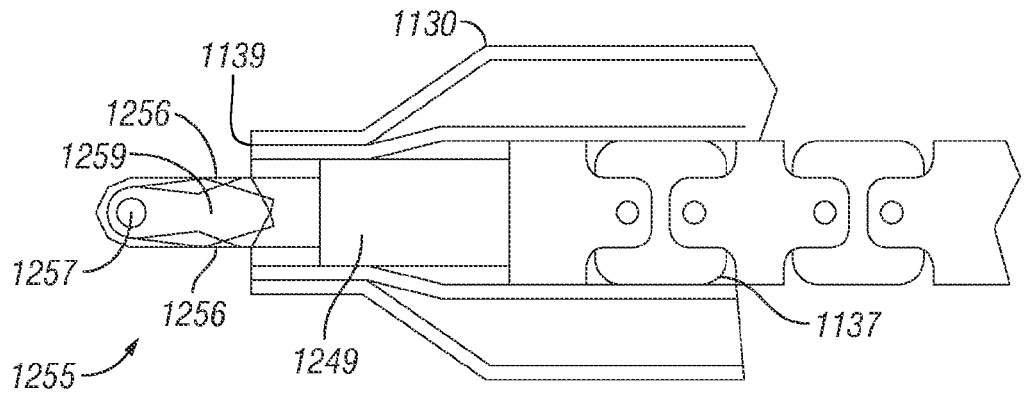
FIGS. 15A-15B illustrate section views of a therapeutic component according to exemplary embodiments of the present disclosure.
Figure 15B:
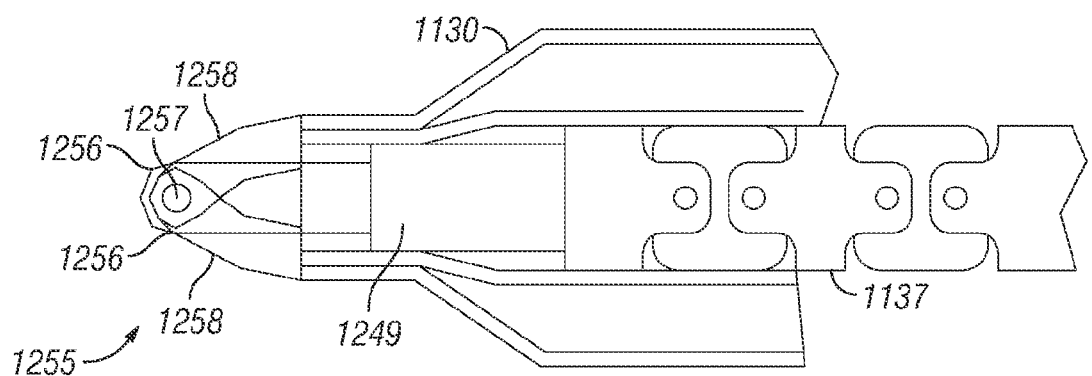

In certain embodiments, a shaft portion of an insertion device may comprise a retention mechanism specifically configured to retain a therapeutic component on the shaft portion of the insertion device. Referring to FIGS. 15A and 15B, a detailed view of one end of shaft portion 1249 of an insertion device illustrates an exemplary embodiment of a retention mechanism 1255. In this embodiment, retention mechanism 1255 is shown in a compressed or unlocked state in FIG. 15A and in an expanded or locked position in FIG. 15B.

In this particular embodiment, retention mechanism 1255 comprises retaining members 1256 (e.g., clips or wires) that are biased toward the expanded, locked position shown in FIG. 15B via a biasing member 1259. During installation of therapeutic component 1130, a user may compress retaining members 1256 by pushing the retaining members 1256 towards the center portion of shaft portion 1249 and rotating retaining members 1256 about a pivot point 1257. In certain embodiments, therapeutic component 1130 may compress retaining members 1256 during installation as it slides over retaining members 1256. In this embodiment, retaining members 1256 comprise a tapered portion 1258 to facilitate the compression or rotation of retaining members 1256 as therapeutic component 1130 initially engages and then slides over retaining members 1256. As therapeutic component 1130 slides over retention mechanism 1255, first lumen 1137 of therapeutic component 1130 remains engaged with retaining members 1256 and keeps retaining members 1256 in a compressed condition.

Retaining members 1256 can remain in the compressed condition shown in FIG. 15A until therapeutic component 1130 is moved sufficiently far down shaft portion 1249 so that first lumen 1137 is no longer engaged with retaining members 1256. When therapeutic component 1130 is moved to the position shown in FIG. 15B, retaining members are no longer constrained by first lumen 1137. At this point, retaining members 1256 are moved to the locked position by biasing member 1259. In this position, retaining members 1256 are engaged with an end surface 1139 of therapeutic component 1130. The engagement of retaining members 1256 and end surface 1139 prevent therapeutic component 1130 from moving axially back over retaining mechanism 1255 and keeps therapeutic component 1130 retained to shaft portion 1249 of the insertion device. To remove therapeutic component 1130, a user may manually compress retaining member 1256 and then slide off therapeutic component 1130 from shaft 1249.

Figure 16A:
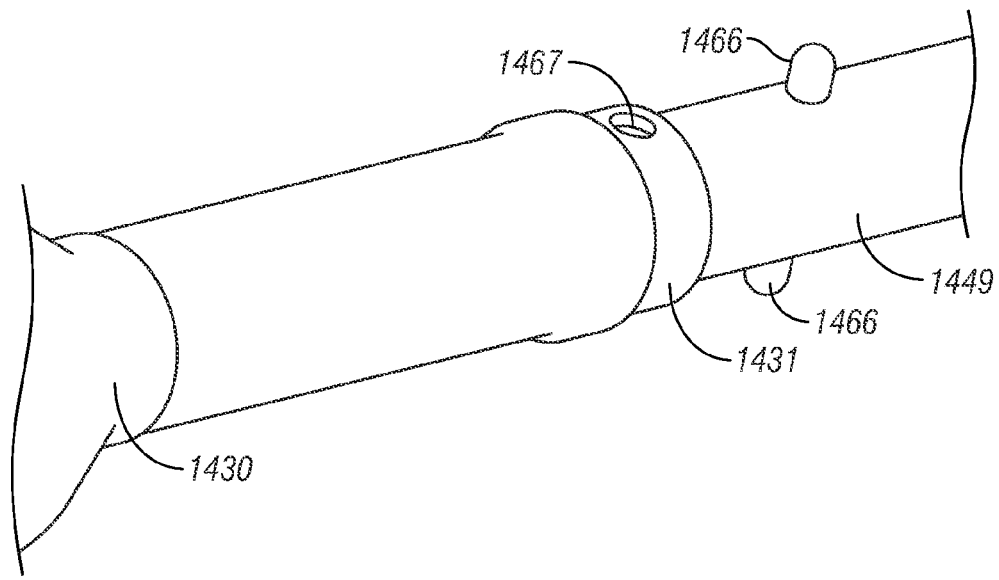
FIGS. 16A-16E illustrate perspective views of a retention mechanism according to exemplary embodiments of the present disclosure.
Figure 16B:
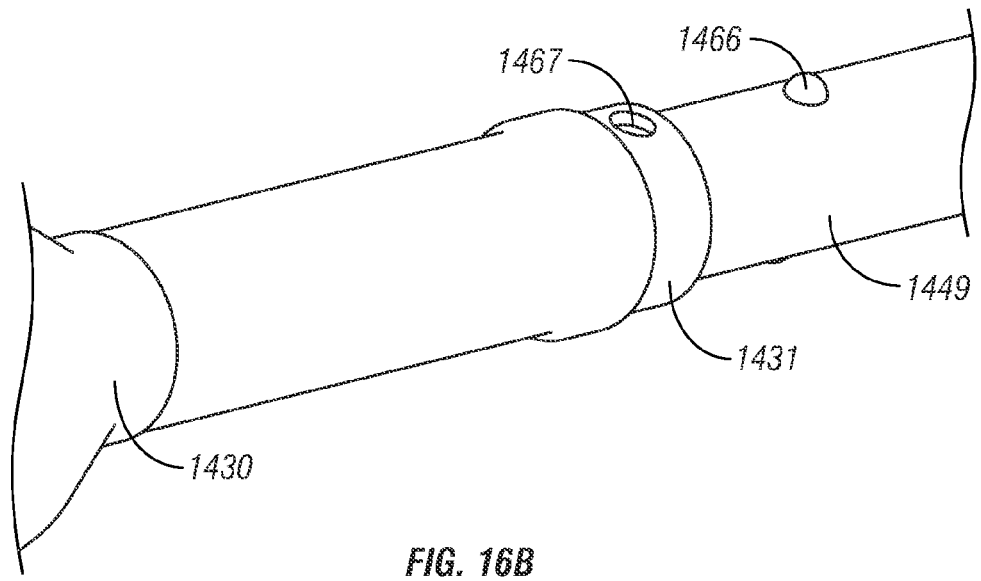
Figure 16C:
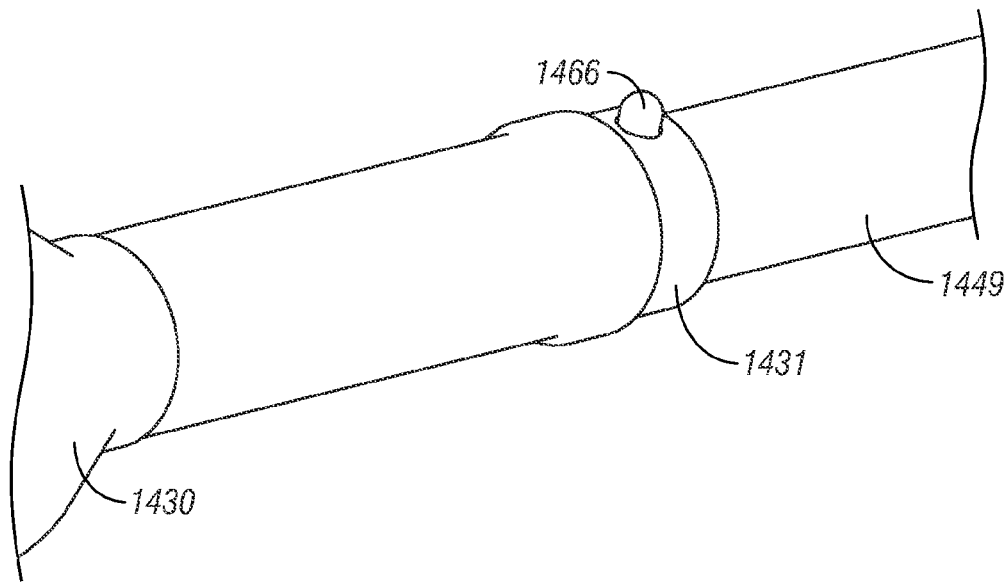

Referring now to FIGS. 16A-16C, another embodiment comprises a shaft portion 1449 including a retention mechanism having one or more retaining members 1466 (e.g., pins, rods, or tabs) that may engage receiving members 1467 on a collar 1431 coupled to therapeutic component 1430. In this embodiment, receiving members 1466 may be in an extended position shown in FIG. 21 or a retracted position shown in FIG. 16B. In exemplary embodiments, retaining members are biased by a biasing member to the extended position shown in FIGS. 21 and 23. In specific embodiments, retaining members 1466 may be moved from the extended position to the retracted position by an actuation member (e.g., a trigger, lever, or sliding member) located on the proximal handle of an insertion device configured to insert therapeutic component 1430.

During operation, a user may couple therapeutic component 1430 to shaft portion 1449 by retracting engagement members 1466 (as shown in FIG. 16B), aligning receiving members 1467 with retaining members 1466, and then allowing engagement members 1466 to return to their extended position (as shown in FIG. 16C). After therapeutic component 1430 is coupled to shaft portion 1449, a user may insert therapeutic component into a sinus or other opening and place it in the desired location. If desired, the user may actuate the actuation member to retract retaining members 1466 and remove shaft portion 1449 from coupling member 1430 prior to expanding therapeutic component 1430.

After therapeutic component 1430 has been expanded (e.g., in a manner previously described), therapeutic component 1430 may then be contracted (e.g., deflated) and re-coupled to shaft portion 1449. For example, the actuation member on the insertion device can be actuated to retract retaining members 1466 prior to shaft portion 1449 being inserted into collar 1431. The actuation member may then be released so that retaining members 1466 return to their expanded position and engage receiving members 1467. In specific embodiments, collar 1431 and shaft portion 1449 may comprise alignment members (e.g., slots, grooves, etc.) to assist in aligning retaining members 1466 and receiving members 1467. Once retaining members 1466 and engagement members 1467 are engaged, shaft portion 1449 can be withdrawn from the sinus or other opening and therapeutic component 1430 can be removed. If desired, therapeutic component 1430 may be re-inserted and used to dilate the same opening or another opening. This embodiment provides the user with the ability to couple or de-couple therapeutic component 1430 and shaft portion 1449 remotely (e.g., via the actuation member located on the insertion device) without having to manually manipulate retention members at the interface between the therapeutic component and the shaft portion.

Figure 16D:
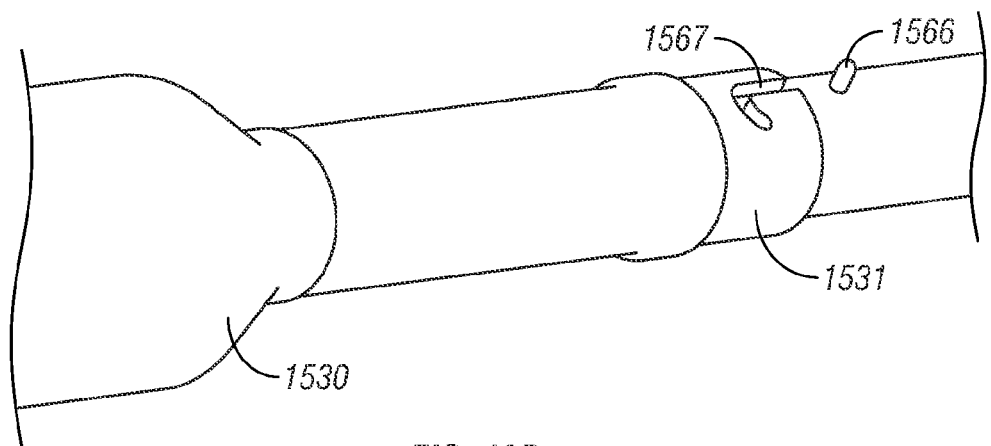
Figure 16E:
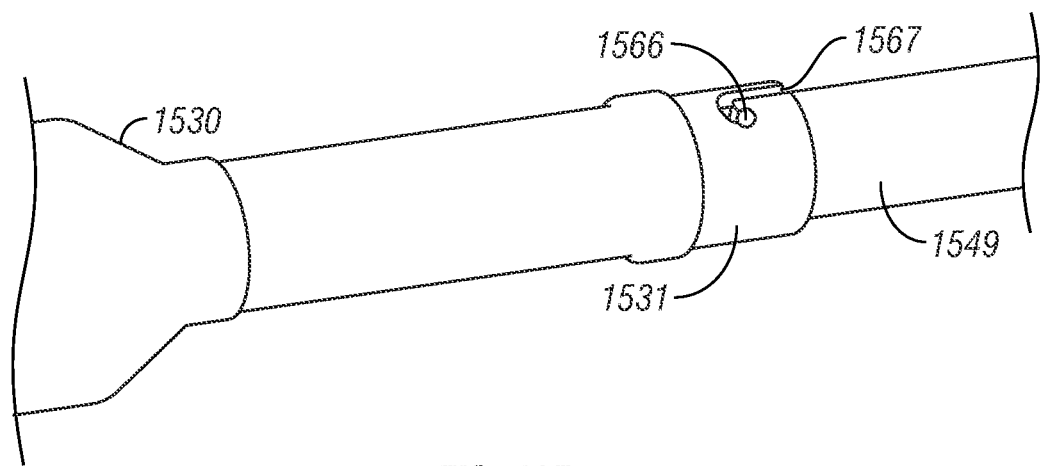

Referring now to FIGS. 16D-16E, another embodiment comprises one or more retaining members 1566 (e.g., pins, rods, or tabs) that may engage receiving members 1567 on a collar 1531 coupled to therapeutic component 1530. In this embodiment, receiving members 1567 do not retract and extend to engage receiving members 1567, but instead slide axially into receiving members 1567. After retaining members 1566 have engaged receiving members 1567, shaft portion 1549 may be rotated radially (e.g., twisted) with respect to collar 1431 to place retaining members 1566 into the position shown in FIG. 16E. In this embodiment, receiving members 1567 are configured as "J-shaped" slots that retain retaining members 1566. In specific embodiments, receiving members 1567 may comprise biasing members configured to bias retaining members 1566 into the position shown in FIG. 16E. When it is desired to remove therapeutic component 1530 from shaft portion 1549, a user may move shaft portion 1549 radially and axially in order to disengage retaining members 1566 from receiving members 1567.

In certain embodiments, a retention mechanism may comprise an enlarged portion of an insertion device. For example, referring now to FIG. 17A, an insertion device 750 comprises a first end 753, a second end 754, a curved or angled portion 752, and an enlarged portion 751 near second end 754. In certain embodiments, insertion device 750 is a device commonly known as an ostium seeker. In the embodiment shown in FIG. 17A, insertion device 750 is configured for insertion in a frontal sinus (e.g., angled portion 752 is angled to permit a user to insert enlarged portion 751 into a frontal sinus). Insertion device 750 may also be inserted into a lumen 732 of a therapeutic component 730. As shown in FIG. 17B, enlarged portion 751 can engage a receiving member 731 within therapeutic component 730. In certain embodiments, enlarged portion 751 and receiving member 731 can be similarly shaped (with receiving member 731 being a concave shape and enlarged portion 751 being a convex shape) so that therapeutic component 730 is positively engaged during use. Therapeutic component 730 may be coupled to insertion member 750 and inserted to the desired location before therapeutic component is inflated via conduit 740.

Figure 17A:
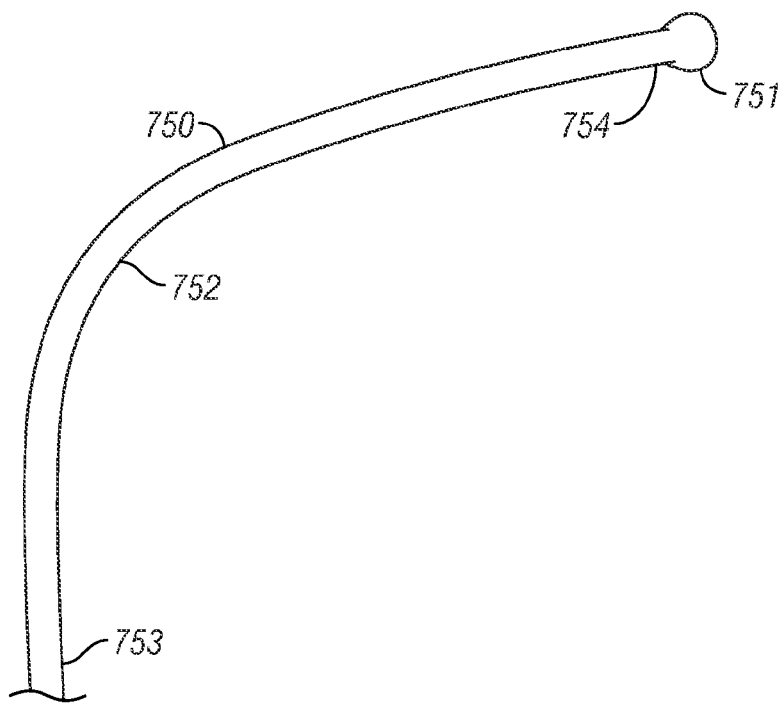
FIGS. 17A-17D illustrate a side views of an insertion device and a therapeutic component according to exemplary embodiments of the present disclosure.
Figure 17B:
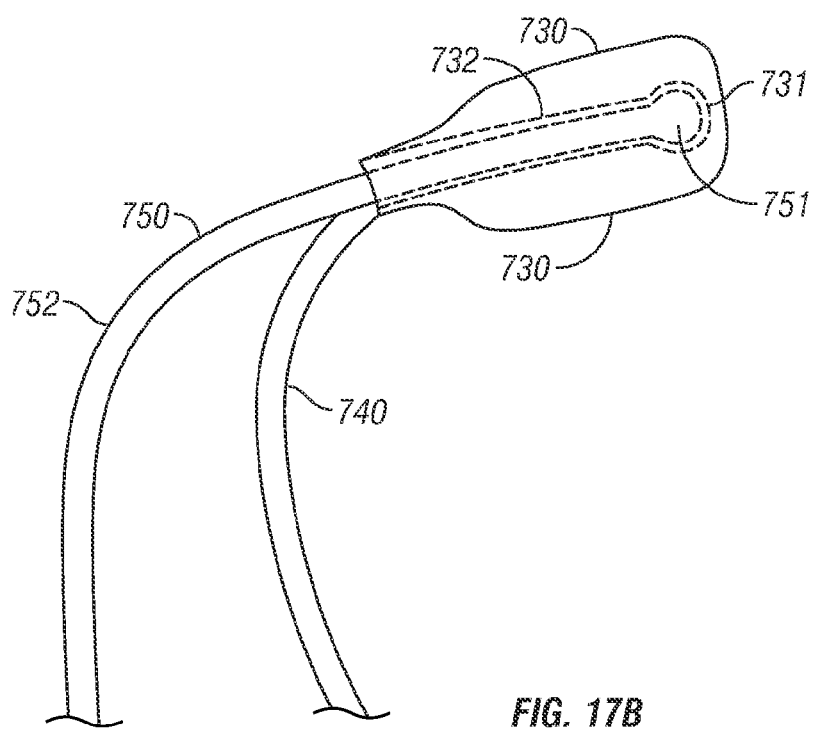
Figure 17C:
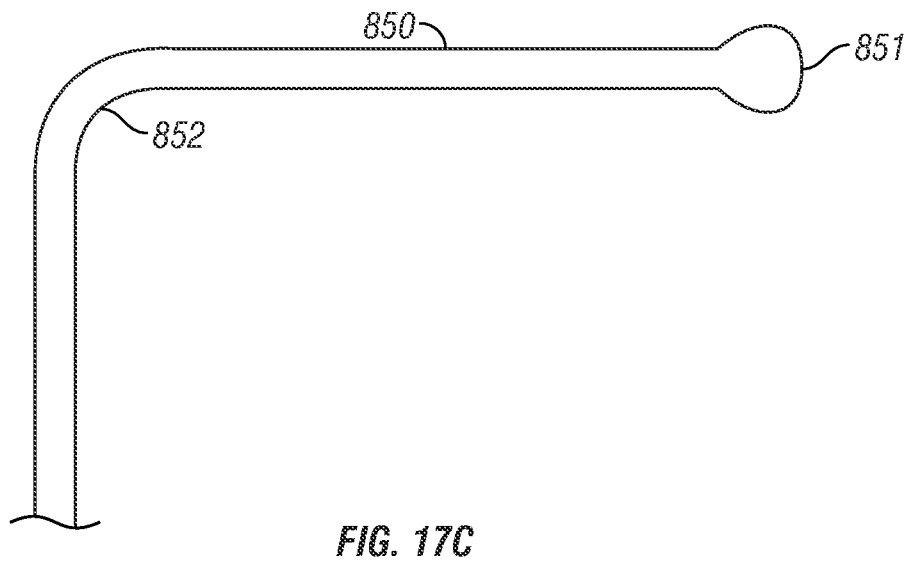
Figure 17D:
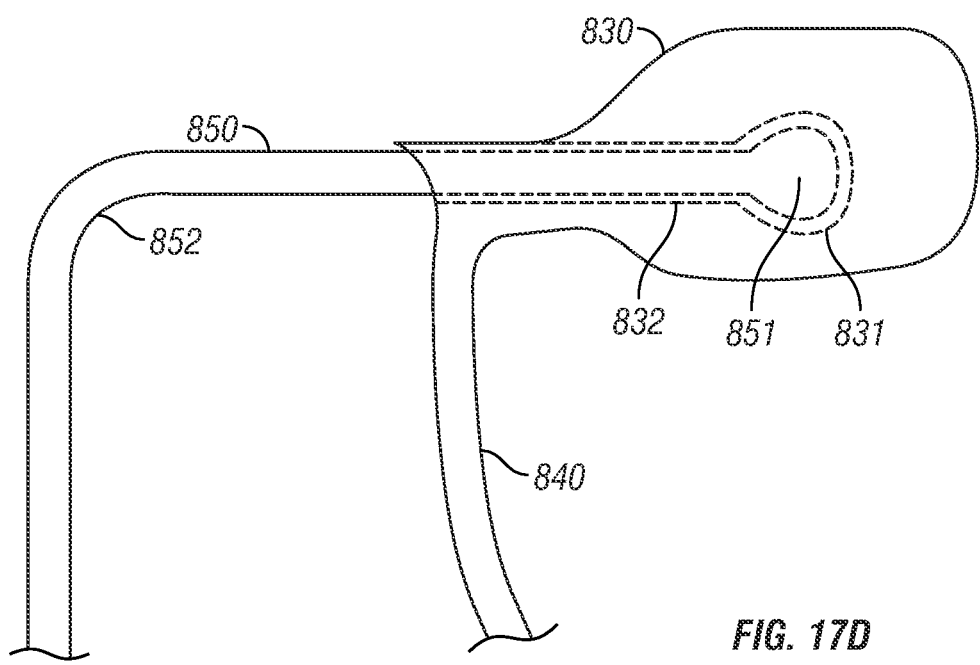

Referring now to FIGS. 17C-17D, an insertion device 850 and therapeutic component 830 are similar to that shown in FIGS. 17A-17B. For example, insertion device 850 comprises an angled portion 852, and an enlarged portion 851 at a distal end. Therapeutic component 830 also comprises a lumen 832 and a receiving member 831 configured to receive enlarged portion 851. In this embodiment, however, curved or angled portion 852 is angled at a greater degree than angled portion 752. In certain embodiments, angled portion 852 is angled at approximately 90 degrees and, in certain embodiments, is configured to be inserted into a maxillary sinus.

In certain embodiments, insertion device 750 is a device commonly known as an ostium seeker. In the embodiment shown in FIG. 17A, insertion device 750 is configured for insertion in a frontal sinus (e.g., angled portion 752 is angled to permit a user to insert enlarged portion 751 into a frontal sinus). Insertion device 750 may also be inserted into a lumen 732 of a therapeutic component 730. As shown in FIG. 17B, enlarged portion 751 can engage a receiving member 731 within therapeutic component 730. In certain embodiments, enlarged portion 751 and receiving member 731 can be similarly shaped (with receiving member 731 being a concave shape and enlarged portion 751 being a convex shape) so that therapeutic component 730 is positively engaged during use. Therapeutic component 730 may be coupled to insertion member 750 and inserted to the desired location before therapeutic component is inflated via conduit 740.

Extension Coupling Member Embodiments

Figure 18A:
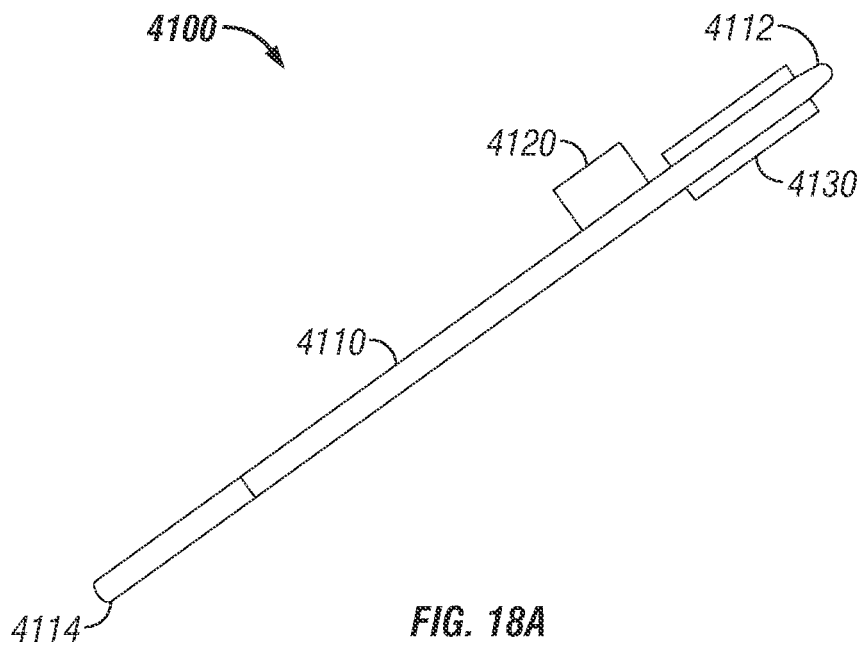
FIGS. 18A-18C illustrate side views of a therapeutic component and an elongate device according to exemplary embodiments of the present disclosure.

In certain embodiments, an insertion device may couple to a coupling member configured as a protuberance or extension from a shaft inserted into an anatomical passage. Referring now to FIG. 18A, an elongate device 4100 comprises an elongate shaft 4110, a coupling member 4120, and a therapeutic component 4130 that is proximal to a first end 4112 of elongate shaft 4110. In certain embodiments, coupling member 4120 comprises a protuberance or extension from elongate shaft 4110, and therapeutic component 4130 comprises an inflatable balloon. In certain embodiments, coupling member 4120 may be integral to elongate shaft 4110, including for example, molded into elongate shaft 4110. In other embodiments, coupling member 4120 may be a separate component. In a specific embodiment, coupling member 4120 may comprise a portion of an adhesive member (e.g., surgical tape) that has been wrapped around elongate shaft 4110. In other embodiments, coupling member 4120 may comprise a molded tab that is fit onto elongate shaft 4110. In specific embodiments, coupling member 4120 may be molded from a plastic or other polymer material.

Figure 18B:
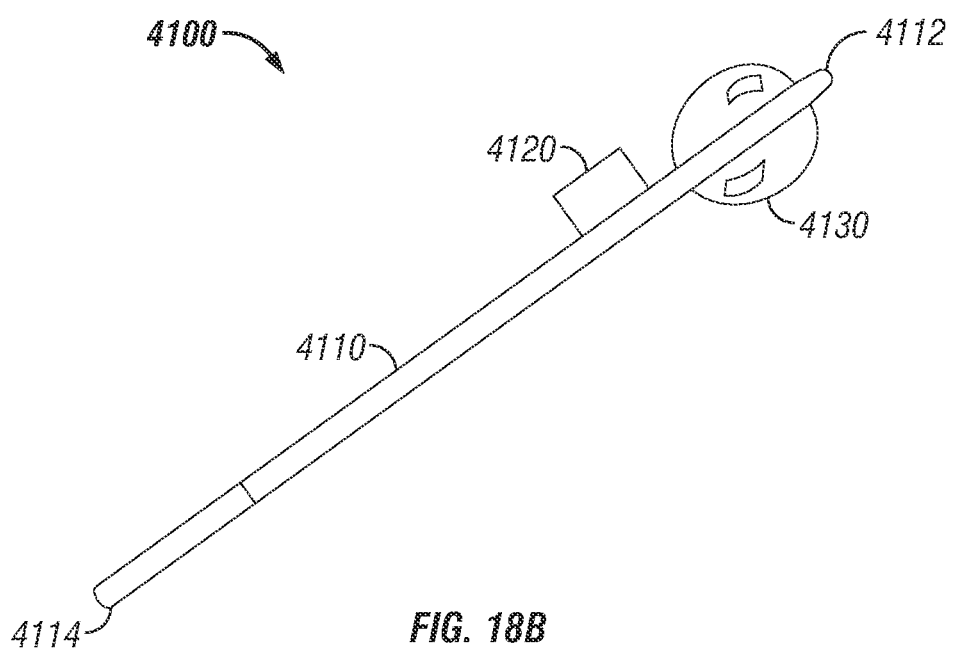

In the configuration shown in FIG. 18A, therapeutic component 4130 is shown in a contracted condition. As shown in FIG. 18B, therapeutic component 4130 can be expanded to increase the external diameter and circumference of therapeutic component 4130. In specific embodiments, elongate shaft 4110 comprises an internal conduit (not visible in the figures) that extends between therapeutic component 4130 and a second end 4114 of elongate shaft 4110. In such embodiments, therapeutic component 4130 may be inflated by introducing a higher pressure fluid (e.g., air or liquid) to increase the pressure at second end 4114 and expanding therapeutic component 4130.

Figure 18C:
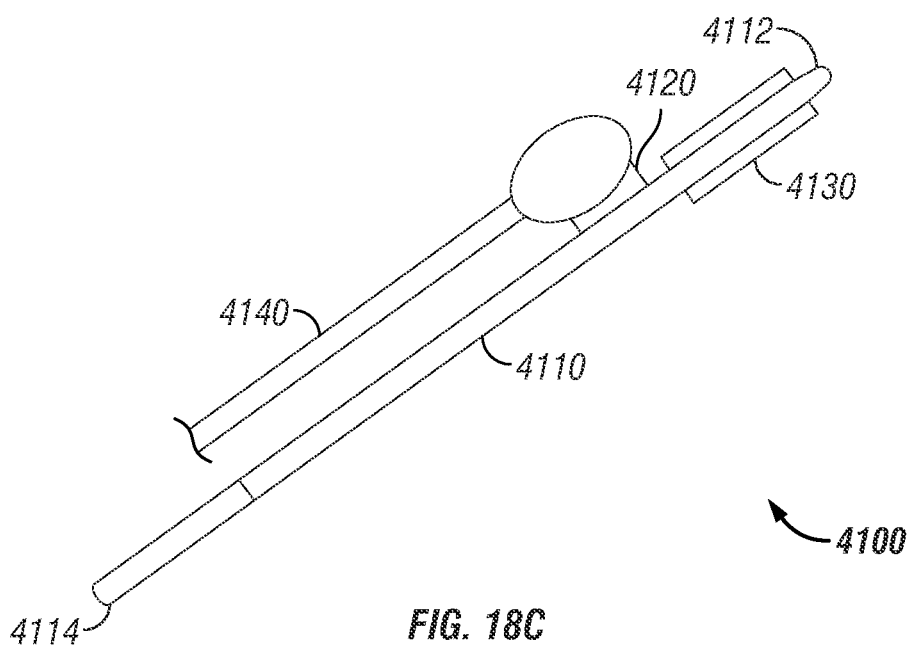

Referring now to FIG. 18C, an insertion device 4140 is shown coupled to coupling member 120. In specific embodiments, insertion device 4140 comprises either rigid or articulating grasping forceps. In certain embodiments, insertion device 4140 may comprise Blakesley-type forceps. Insertion device 4140 may be used to grasp coupling member 4120 and direct elongate device 100 within an anatomical structure.

Figure 19A:
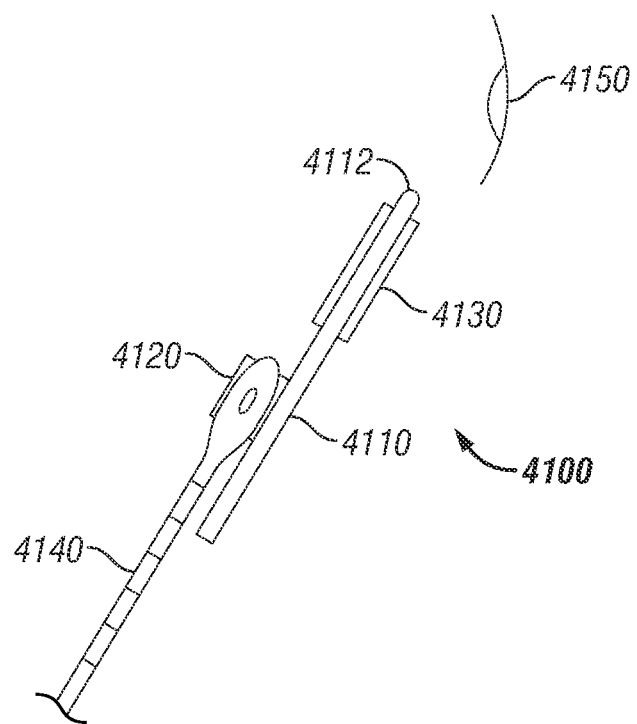
FIG. 19A illustrates a side view of the embodiment of FIGS. 18A-18C being directed towards an anatomical passageway.
Figure 19B:
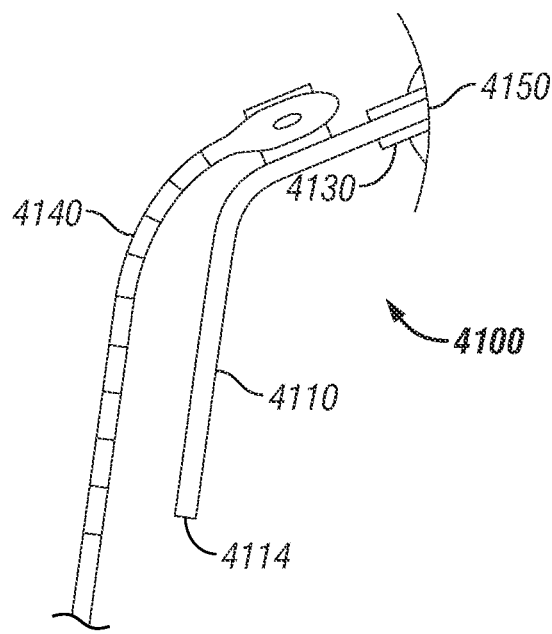
FIG. 19B illustrates a side view of the embodiment of FIGS. 18A-18C being inserted into an anatomical passageway.

Referring now to FIG. 19A-19B, elongate device 4100 has been coupled to insertion device 4140 and is being directed towards an anatomical structure 4150. In specific embodiments, anatomical structure 4150 may comprise a paranasal sinus (e.g., a maxillary or frontal sinus). As shown in FIG. 19B, insertion device 4140 has been articulated to direct elongate device 4100 into anatomical structure 4150. Elongate device 4100 can then be placed in the desired location (e.g., so that therapeutic component 130 is in the desired location within anatomical structure 150). When elongate device 4100 is in the desired location, therapeutic component 4130 can be expanded by increasing the pressure at second end 4114 of elongate shaft 4110. This will allow the pressure within the internal conduit in elongate shaft 4110 to increase, and will cause therapeutic component 4130 to be expanded. The expansion of therapeutic component 4130 can be used to dilate a paranasal sinus or other anatomical passageway.

Figure 19C:
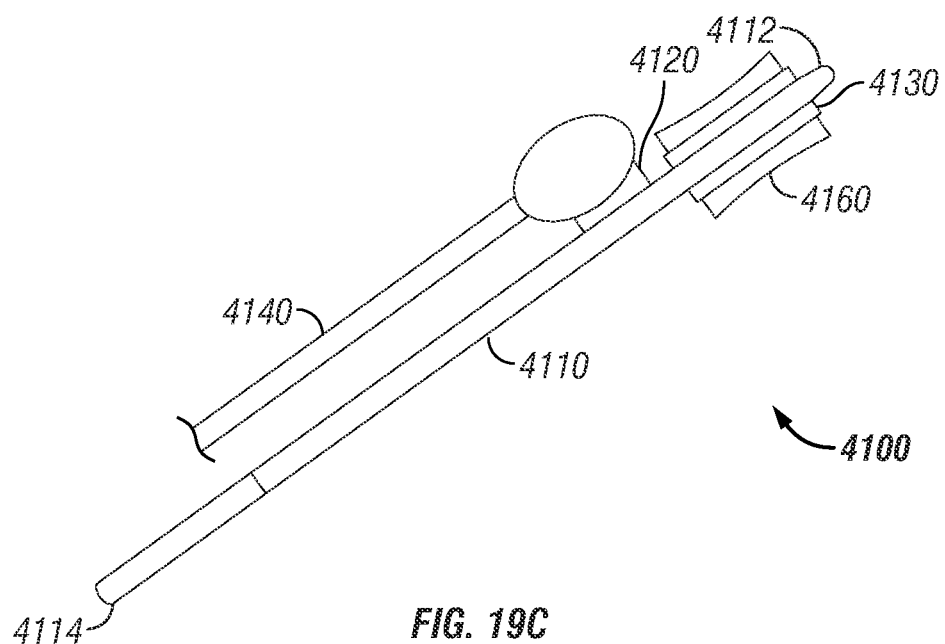
FIG. 19C illustrates a side view of the embodiment of FIGS. 18A-18C with a stent being directed towards an anatomical passageway.

In certain embodiments, elongate device 4100 may be used to place a stent in an anatomical structure. Referring now to FIG. 19C, a stent 4160 is shown disposed around therapeutic component 4130. During use, elongate device 4100 can be inserted into an anatomical structure so that therapeutic component 4130 and stent 4160 are placed in a desired location. When the device is properly positioned, therapeutic component 4130 can be expanded, as previously described. Stent 4160 can therefore also be expanded so that it engages the anatomical structure into which it has been inserted. Therapeutic component 4130 may then be contracted (e.g., via deflation by releasing the pressure within therapeutic component 4130 and the internal conduit in elongate shaft 4110). Elongate device 4100 can then be withdrawn, leaving stent 4160 in place.

Figure 20:
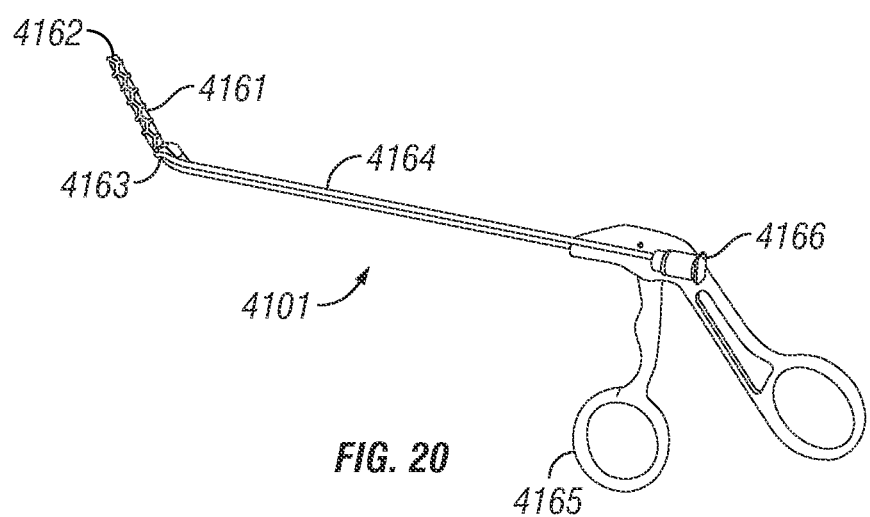
FIG. 20 illustrates a perspective view of an insertion device with a stent according to exemplary embodiments of the present disclosure.

Referring now to FIG. 20, an elongate device 4101 comprises a stent 4161 disposed on a balloon 162 that can be expanded to deploy stent 4161 in a desired location in an anatomical structure. Elongate device 4101 comprises an actuation member 4165 configured to articulate an articulation point 4163 to assist in locating balloon 4162 and stent 4161 in the desired location. Other embodiments may comprise multiple articulation points. An inflation lumen 4164 and a coupling member 4166 may be coupled to a pressurizing member (not shown) to inflate balloon 4162 and deploy stent 4161.

Figure 21A:
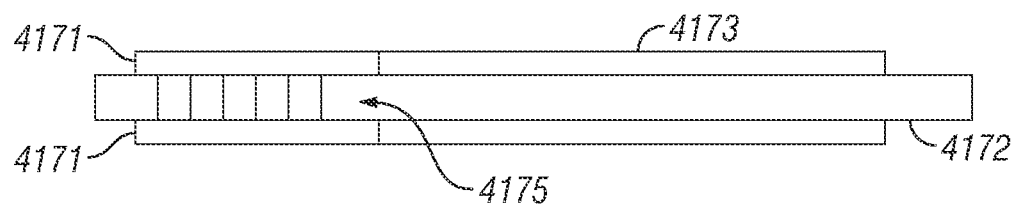
FIGS. 21A-21B illustrate a side view of an insertion device with a self-expanding stent according to exemplary embodiments of the present disclosure.
Figure 21B:
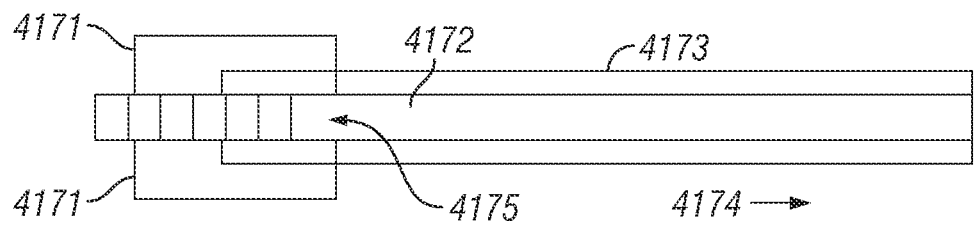

Referring now to FIG. 21A-21B, in certain embodiments, a self-expanding stent 4171 may be utilized. For example, a self-expanding stent may be placed on an inner shaft 4172 at a distal end of an instrument. Inner shaft 4172 may have retention features 4175 (e.g., ridges, grooves, or other configurations) so that the stent does not inadvertently slip off inner shaft 4172. A retention sleeve 4173 may keep self-expanding stent 4171 in a retracted configuration as shown in FIG. 21B. However, self-expanding stent 4171 may be expanded when retention sleeve 4173 is moved in direction 4174 after placement within the sinus.

Extending/Articulating Embodiments

Figure 22A:
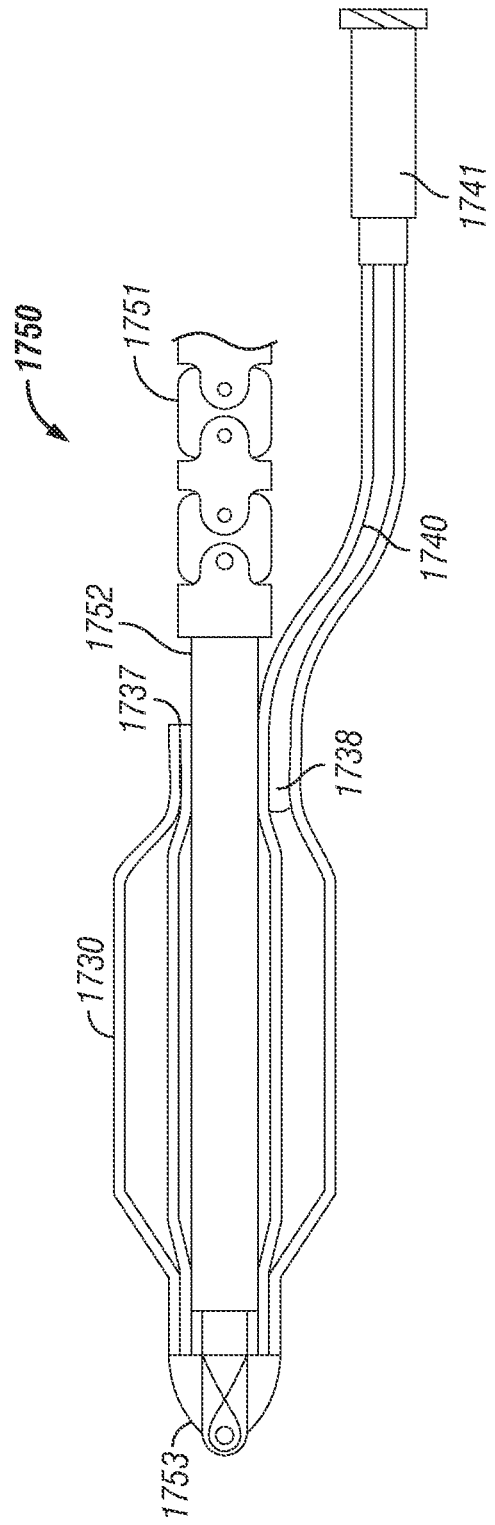

In certain embodiments, a therapeutic component may be coupled to a shaft that comprises an articulating and/or extending portion. Referring now to FIGS. 22A-22B, a therapeutic component 1730 is coupled to a shaft member 1750 that comprises an articulating portion 1751 and an extending portion 1752. In the embodiment, therapeutic component 1730 comprises a first lumen 1737 configured to receive an extending portion 1752 and a second lumen 1738 in fluid communication with a conduit 1740 and a coupling member 1741 configure couple to a pressurizing member (not shown). As shown in FIG. 22A, extending portion 1752 is in a retracted configuration and articulating portion 1751 is shown in a straight configuration. As shown in FIG. 22B, however, extending portion 1752 is shown extended, and articulating portion 1751 is articulated to approximately 90 degrees.

In the embodiment shown, shaft member 1750 comprises a coupling member 1753 that couples therapeutic component to the distal end of extending portion 1752. As a result, therapeutic component 1730 will move with extending portion 1752 as it is extended. This configuration can allow increased flexibility or access distance when therapeutic component 1730 is inserted into a sinus or other opening.

Extending/Retracting Embodiments

Referring now to FIGS. 23A-23D, schematic views illustrate an embodiment comprising an insertion device 1600 including an actuator 1647 configured to extend and retract a shaft portion 1649 and a therapeutic component 1630. In this embodiment, actuator 1647 comprises a rotating member (e.g., a thumbwheel) that engages shaft portion 1649 extending from a handle portion 1646. In particular embodiment shown, shaft portion 1649 comprises teeth or gears 1648 that engage actuator 1647. Shaft portion also comprises a retaining member 1643 that engages actuator 1647 when shaft portion 1649 is fully extended. Insertion device 1600 also comprises a port 1641 configured to receive fluid (e.g., saline or air) that may be used to expand therapeutic component 1630.

Figure 23A:
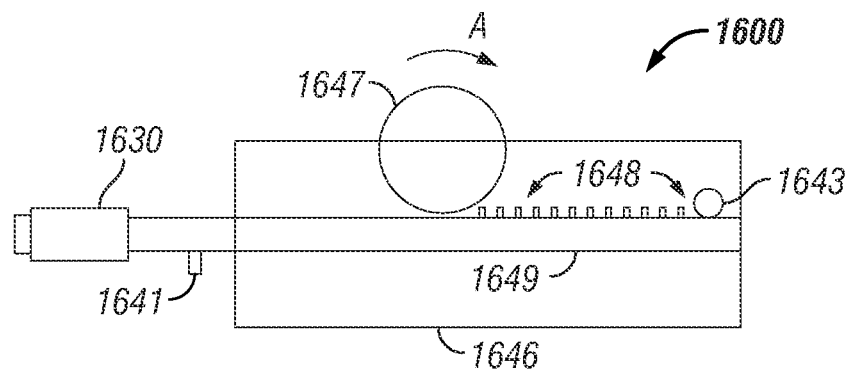
FIGS. 23A-23D illustrate schematic views of an insertion device according to exemplary embodiments of the present disclosure
Figure 23B:
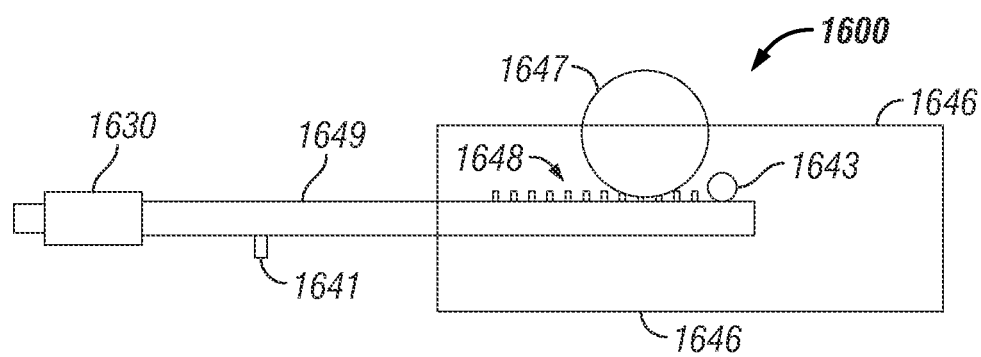

As shown in FIG. 23A, shaft portion 1649 is initially in a retracted position. However, when actuator 1647 is rotated in the direction shown by arrow "A", shaft portion 1649 will be extended from handle portion 1646 into the position shown in FIG. 23B. This position can allow a user to insert therapeutic component 1630 into a sinus or other opening prior to expanding or dilating therapeutic component 1630.

Figure 23C:
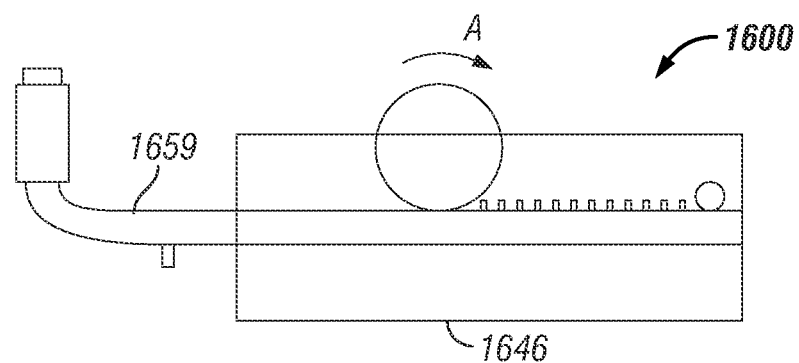
Figure 23D:
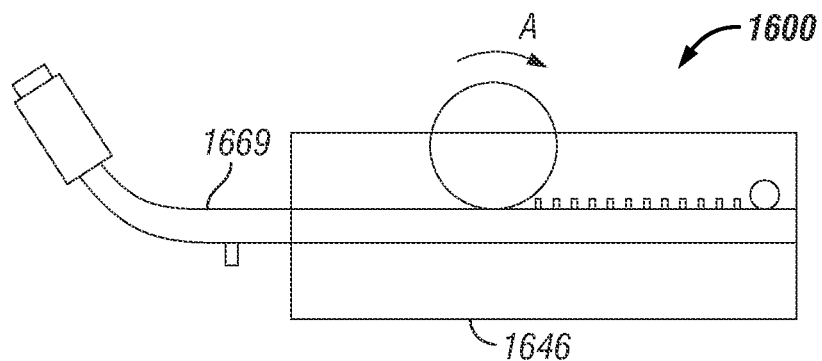

As shown in FIGS. 23C and 23D, shaft portions that are angled or curved may also be used in conjunction with handle portion 1646. In the embodiment shown in FIG. 23C, shaft portion 1659 comprises a distal end that is angled approximately 90 degrees from the proximal end (e.g. the end proximal to handle portion 1646 when shaft portion 1659 is installed in handle portion 1646). In the embodiment shown in FIG. 23D, the distal end is angled at approximately 60 degrees from the proximal end of shaft portion 1669. The other unlabeled components in FIGS. 23C and 23D are equivalent to those shown and labeled in FIGS. 23A and 23B. It is understood that other embodiments may comprise an end portion that is angled at a different angle from the proximal end. For example, certain embodiments may comprise a distal portion angled at an angle of 15, 30, 45, or 75 degrees. In still other embodiments, the shaft portion may comprise a flexible portion that allows the end portion of the shaft to be set at a desired angle prior to inserting the therapeutic component into the sinus or other opening.

Biasing Member/Shape Memory Embodiments

Figure 24A:
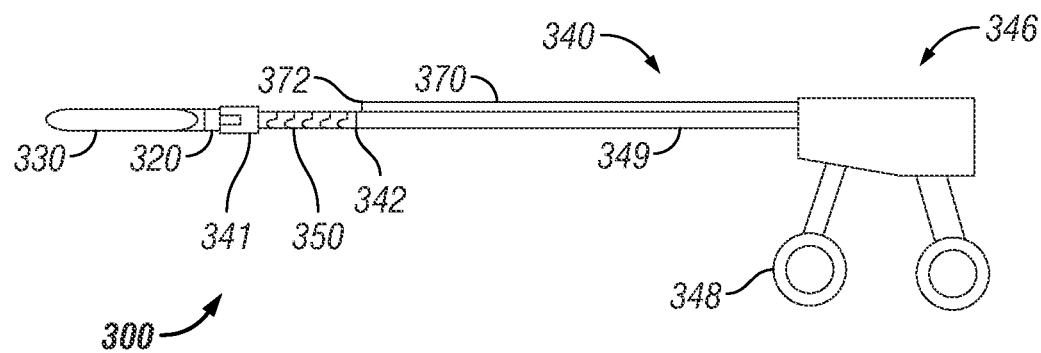
FIGS. 24A-24B illustrate side views of an insertion device configured to insert an elongate device according to exemplary embodiments of the present disclosure.
Figure 24B:
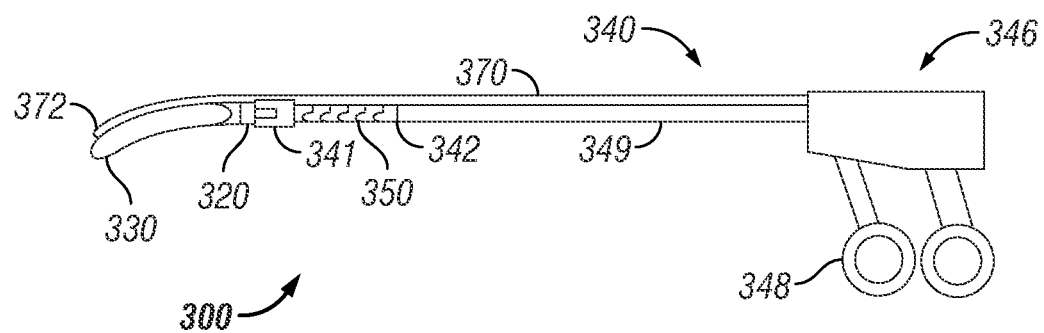

Referring now to FIGS. 24A-24B, side views are shown of an exemplary embodiment of an insertion device 340 in various positions. As shown in FIGS. 24A-24B, insertion device 340 comprises a handle portion 346 and a shaft portion 349 extending from handle portion 346. In the embodiment shown, shaft portion 349 comprises one or more articulating segments 350 proximal to first end 342 of shaft portion 349. In certain embodiments, a sheath (not shown for purposes of clarity) may cover articulating segments 350. Insertion device 340 also comprises a positioning member 370 configured to position a therapeutic component 330. In specific exemplary embodiments, positioning member 370 comprises a biasing member constructed from an elastic or super-elastic material (e.g., nitinol or stainless steel). Insertion device 349 also comprises a control member 348 configured to control the position of positioning member 370 (e.g., control member 348 can be manipulated to extend or retract positioning member 370). Other embodiments may comprise a different configuration for the handle portion and control member to control the position of positioning member 370. For example, in certain embodiments, the handle portion may be configured similar to a screwdriver handle and the control member may be a sliding mechanism configured to extend or retract positioning member 370.

Positioning member 370 is shown in refracted position in FIG. 24A and in an extended position in FIG. 24B. In the retracted position, a first end 372 of positioning member 370 does not extend past first end 342 of shaft portion 349. In this position, shaft portion 349 maintains positioning member 370 in a generally straight position parallel to shaft portion 349. In the extended position shown in FIG. 24A, first end 372 of positioning member 370 extends past first end 342 and engages therapeutic component 330. Shaft portion 349 no longer engages first end 372, and a portion of positioning member 370 (e.g., a portion proximal to first end 372) is allowed to deflect or curve to its predetermined configuration. In moving to its predetermined configuration, positioning member 370 also moves therapeutic component 370 (e.g., causes therapeutic component 330 to be placed in a curved position).

When therapeutic component 330 is in the position shown in FIG. 24A, it can be easier to place therapeutic component 330 in certain locations (e.g., a maxillary sinus). With therapeutic component 330 placed in a desired location, positioning member 370 can be moved to the refracted position and therapeutic component 330 can be expanded (e.g., inflated). Therapeutic component 330 can be expanded to dilate a sinus or other opening and then contracted (e.g., deflated). With therapeutic component 330 contracted, insertion device 340 can be retracted from the patient.

It is understood that the embodiment shown in FIGS. 24A and 24B is only one exemplary embodiment. For example, other embodiments comprising a positioning member similar to positioning member 370 may not comprise an articulating segment at a distal end of a shaft. In addition, other embodiments may comprise a positioning member configured as a sleeve the extends and retracts to position a therapeutic component.

Figure 25B:
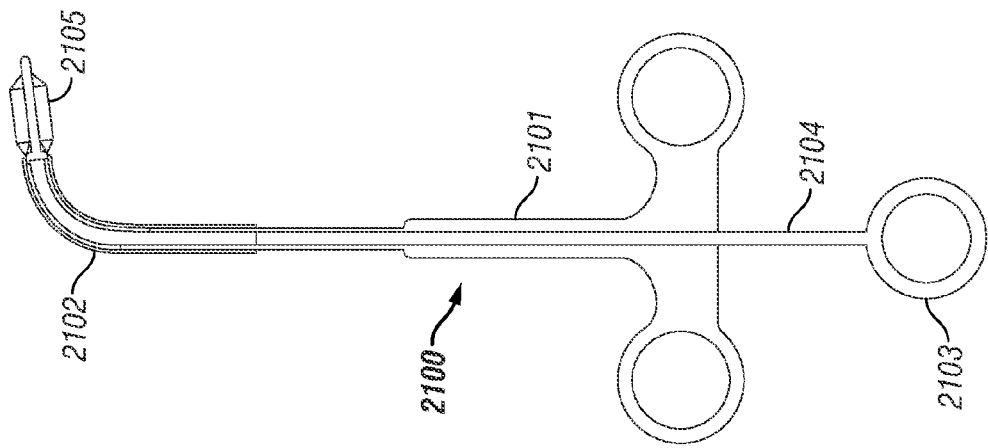
FIGS. 25A-25B illustrate side views of a therapeutic component and an insertion device according to exemplary embodiments of the present disclosure.
Figure 25A:
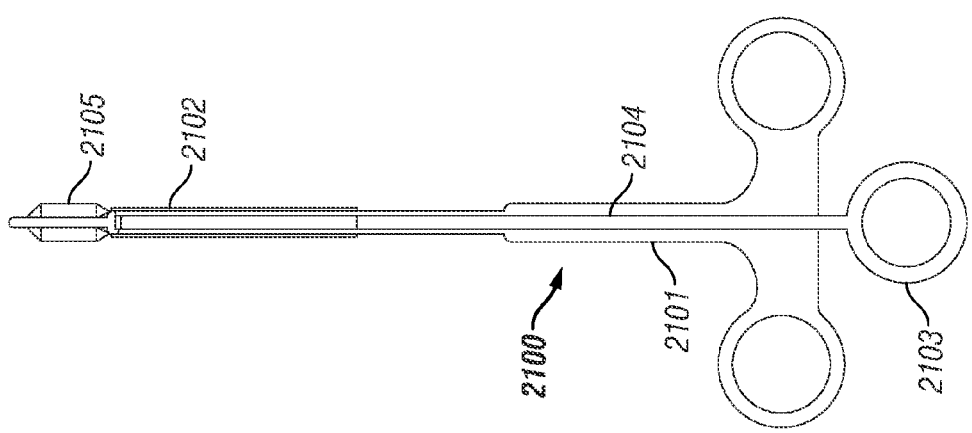

In a certain embodiment, as shown in FIGS. 25A-25B, an insertion device 2100 comprises a central tubular member 2101 having a curved or pre-bent tubular member 2102 at a distal end and an actuator 2103 at a proximal end. A therapeutic component 2105 is coupled to a distal end of pre-bent tubular member 2102. In certain embodiments, therapeutic component 2105 may comprise an expandable therapeutic component, for example an inflatable balloon, while in other embodiments therapeutic component 2105 may comprise a non-expandable therapeutic component.

Insertion device 2100 also comprises an actuation member 2104 configured to be extended or retracted via actuator 2103. In specific embodiments, actuation member 2104 is a push rod that extends through central tubular member 2101. When actuator 2103 is in the extended position shown in FIG. 25A, actuation member 2104 extends into pre-bent tubular member 2102 so that pre-bent tubular member 2102 is forced into a relatively straight configuration that conforms to the shape of actuation member 2104.

However, when actuator 2103 is retracted into the position shown in FIG. 25B, actuation member 2104 retracts so that it no longer forces pre-bent tubular member 2102 into a relatively straight configuration. In certain embodiments, pre-bent tubular member 2102 is comprised of a super elastic material (e.g., nitinol) that returns to a curved or pre-bent shape when actuation member 2104 is retracted.

The ability to move pre-bent tubular member 2102 between a straight configuration and curved or pre-bent configuration can aid in accurate positioning of therapeutic component 2105 into the target sinus ostium. For example, such a configuration can aid in assisting a user to maneuver therapeutic component 2105 around the uncinate process of the ethmoid bone. The amount of deflection may be controlled by the amount of insertion or removal of the actuation member 2104. In an alternate embodiment, the tubular member 2102 may be straight and the actuation member 2104 is pre-bent, allowing for deflection of the tubular member 2102 and the therapeutic component 2105 when the actuation member 2104 is introduced into the tubular member 2102. An actuator 2103 is located at the proximal handle for controlling the position of the actuator member 21034, thus controlling the amount of deflection of the tubular member 2102.

In a variation of the above embodiment, the actuation member 2104 is pre-bent rather than the shaft 2102. In this embodiment, the shaft 2102 may comprise a rigid proximal portion and a flexible distal portion. Therapeutic component 2106 may be positioned over the distal section of the flexible distal portion of shaft 2102. When actuation member 2104 is in a forward position such that the angled or curved section is in the flexible distal portion of shaft 2102, the shaft can conform to the pre-determined angled or curved configuration of actuation member 2104. However, when the actuation member 2104 is pulled back into the rigid section of shaft 2102, the distal portion becomes flexible and can conform to the anatomy. An example of a shaft construction with a rigid proximal portion and a flexible distal portion is a stainless steel or nitinol hypotube which has been cut in a pattern in the flexible portion.

Inflation Conduit Embodiments

Exemplary embodiments may also comprise one of various configurations of a conduit for inflating a therapeutic component. Referring now to FIG. 26A, a side view of a system 400 is shown comprising a therapeutic component 430, a coupling member 435 and an inflation conduit 440. In this embodiment, coupling member 435 extends into a central lumen 437 of therapeutic component 430. In the embodiment shown, inflation conduit 440 is external to (e.g., not co-axial with) coupling member 435. Coupling member 435 may also comprise a collar 436 configured to engage a mating receptacle (not shown) or other engagement member of an insertion device. In certain embodiments, coupling member 435 comprises a rigid shaft that extends into central lumen 437 of therapeutic component 430. System 400 may also comprise a sheath 439 configured to protect linkages contained within sheath 439, as well as tissue into which system 400 has been inserted. Inflation conduit 440 can be used to expand and contract therapeutic component 430 as desired during use (e.g., by introducing and releasing a higher pressure fluid—for example, saline or air—into therapeutic component 430).

Figure 26B:
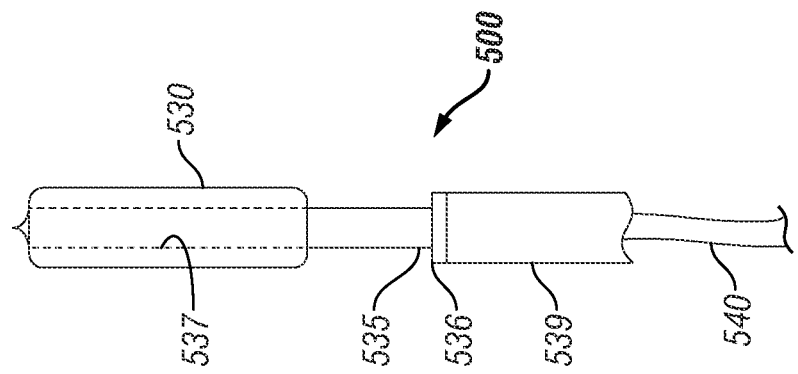
FIGS. 26A-26B illustrate side views of a therapeutic component according to exemplary embodiments of the present disclosure.
Figure 26A:
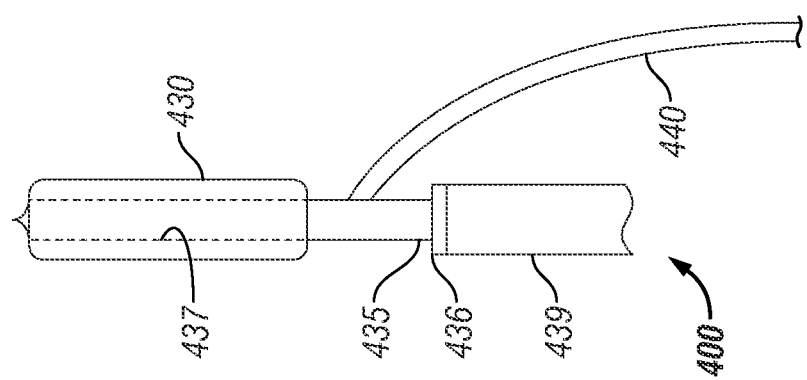

Referring now to FIG. 26B, a side view of a system 500 is shown comprising a therapeutic component 530, a coupling member 535 and an inflation conduit 540. This embodiment is similar to that shown in FIG. 26A, but inflation conduit 540 is now co-axial with coupling member 535 (e.g. inflation conduit 540 extends through sheath 539 and coupling member 535).

Figure 27A:
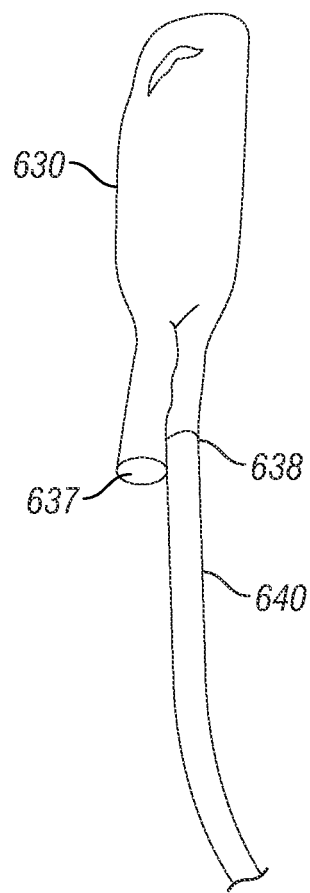
FIGS. 27A-27C illustrate side views of a therapeutic component according to exemplary embodiments of the present disclosure.
Figure 27B:
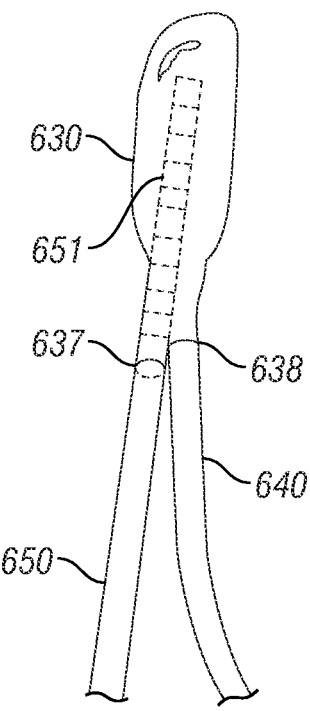
Figure 27C:
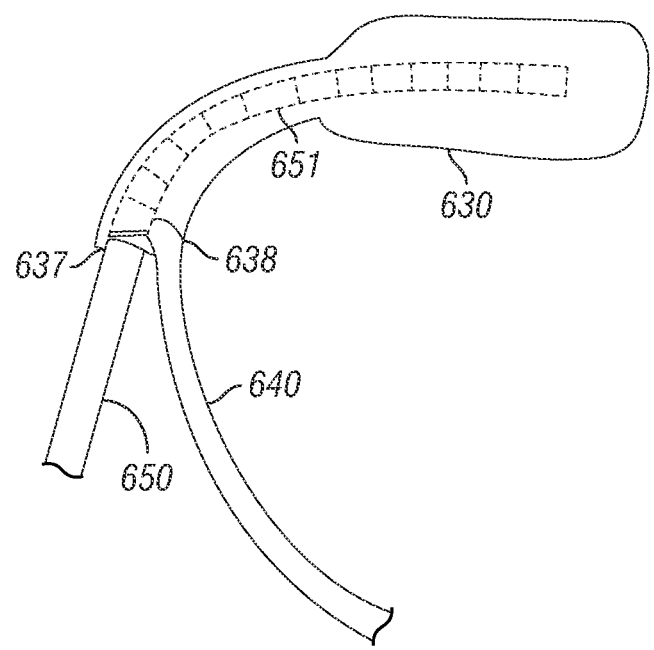

Referring now to FIGS. 27A-27C, side views of a therapeutic component 630 are shown comprising a first lumen 637 configured to receive an insertion device 650 (not shown in FIG. 27A). Therapeutic component 630 may also comprise a second lumen 638 in fluid communication with a conduit 640. In certain embodiments, conduit 640 may be integral to therapeutic component 630, while in other embodiments, therapeutic component may be separated from therapeutic component 630. As shown in FIGS. 27B and 27C, insertion device 650 comprises an articulating portion 651 configured for insertion into lumen 637. In this embodiment, therapeutic component 630 is in fluid communication with conduit 640, which is configured to inflate and deflate therapeutic component 630. As shown in FIG. 27B, an articulating portion of insertion device 650 is inserted within lumen 637. Therapeutic component 630 can remain deflated until it is in the desired location then and inflated via conduit 640 (e.g., to enlarge an opening). Therapeutic component 630 can then be deflated and removed.

Pivoting Embodiments

Figure 28A:
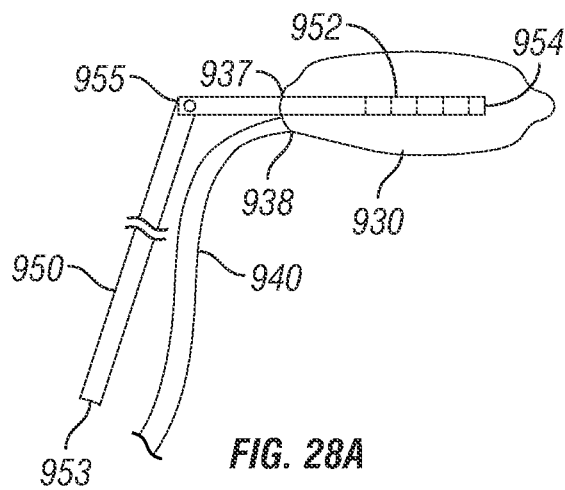
FIG. 28A illustrates a side view of a therapeutic component according to exemplary embodiments of the present disclosure.
Figure 28B:
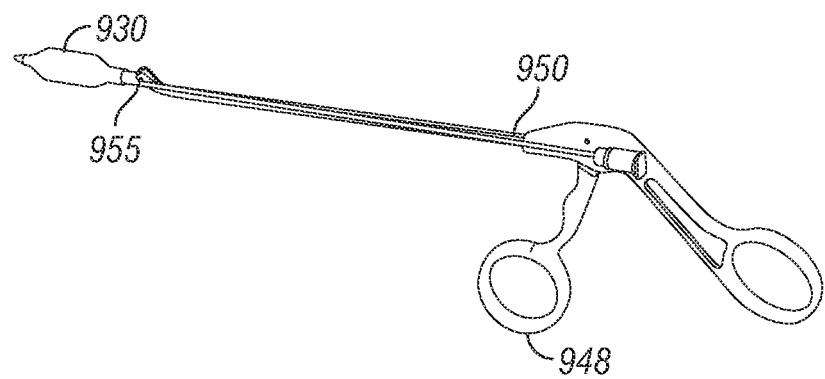
FIGS. 28B-28C illustrate perspective views of the therapeutic component of FIG. 28A coupled to an insertion device.
Figure 28C:
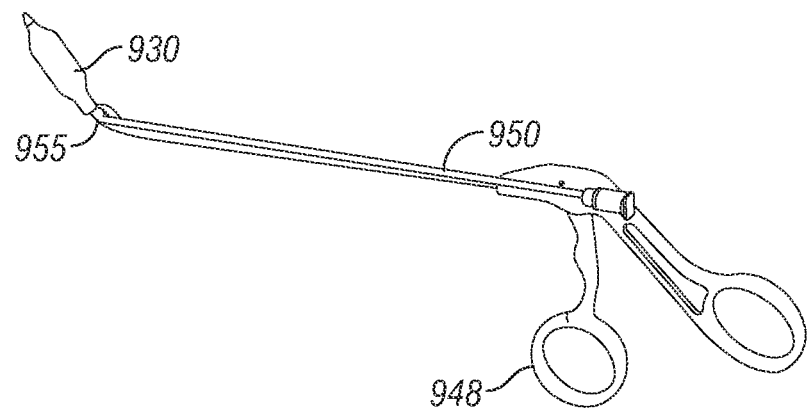

Referring now to FIG. 28A-28C, an exemplary embodiment of insertion device 950 and therapeutic component 930 are provided. In the embodiment shown, therapeutic component 930 comprises a first lumen 937, a second lumen 938, and a conduit 940, similar to previous embodiments. In this embodiment, insertion device 950 comprises a first shaft portion 953, a second shaft portion 954, and a rotation or pivot member 955.

Insertion device 950 may also comprise a coupling mechanism 952 to therapeutic component 930. In the embodiment shown coupling mechanism 952 comprises external threads. In other embodiments, the coupling mechanism may comprise other configurations, including for example, internal threads. In other embodiments, conduit 940 (which can be used to expand therapeutic component 930 during use) may be located within insertion device 950 rather than adjacent to insertion device 950.

In the embodiment shown in FIG. 28A, pivot member 955 is configured so that second shaft portion 954 can be angled between approximately 0 and 90 degrees from first shaft portion 953. As shown in FIGS. 28B and 28C, insertion device 950 may be coupled to an actuation member 948 that can be used to change the angle of second shaft portion 954. In specific embodiments, actuation member 948 may comprise detents that allow second shaft portion 954 to be angled at specific angles (e.g., 5, 10, 15, 20, 25, 30, 35, 40, 45, 50, 55, 60, 65, 70, 75, 80, 85, 90, 95, 100, or 110 degrees).

In certain embodiments, insertion device 950 may comprise one or more channels along first shaft portion 953 and/or second shaft portion 954. In certain embodiments, such channels may be used to flush, irrigate and/or suction a sinus or other opening before, during, or after dilation of the sinus. In certain embodiments, a channel may be configured to fit an endoscope to allow a user to view inside the sinus.

Non-Expandable Therapeutic Component Embodiments

Referring now to FIGS. 29A-29D, an exemplary embodiment comprises a plurality of therapeutic components 1930 that are non-expandable. This embodiment utilizes a series of therapeutic components with successively larger diameters to dilate a sinus or other opening, rather than inserting a single expandable therapeutic component into a sinus or other opening and expanding the therapeutic component. In specific embodiments, the plurality of therapeutic components 1930 may include therapeutic components that have a diameter D1 of 1 mm, 2 mm, 3 mm, 4 mm, 5 mm, 6 mm, 7 mm, 8 mm, 9 mm, or 10 mm. The therapeutic components 1930 can be coupled to a shaft portion 1949 and a handle portion 1946. The sinus or other opening may be dilated by initially inserting a therapeutic component having a diameter D1 slightly larger than the diameter of the sinus/opening. The rounded end portion and curved or tapered surfaces of the therapeutic component 1930 allow for dilation of the sinus/opening as the therapeutic component 1930 is advanced into the sinus/opening while minimizing trauma to the tissue surrounding the sinus/opening. After a specific therapeutic component has been inserted and removed from the sinus/opening, another therapeutic component having a slightly larger diameter D1 may be inserted and removed into the sinus/opening. In this manner, the sinus/opening may be successively dilated until the desired diameter is reached.

Figure 29A:
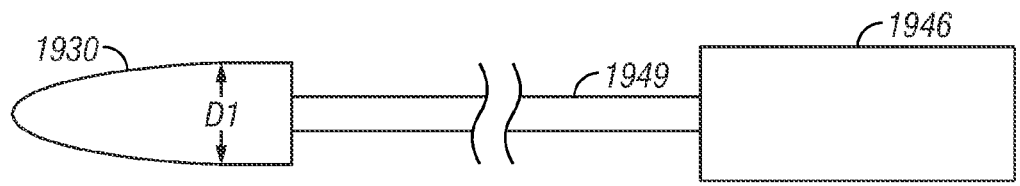
FIG. 29A illustrates a side view of a therapeutic component according to exemplary embodiments of the present disclosure.
Figure 29B:
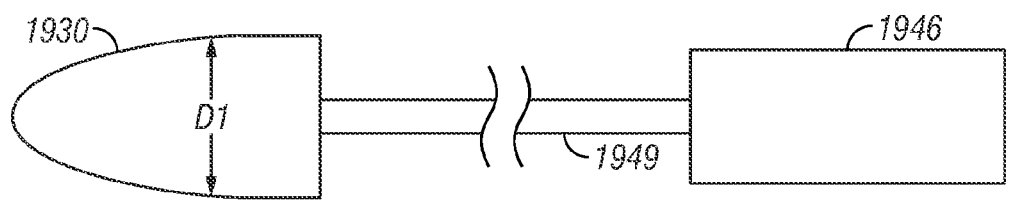
FIG. 29B illustrates a side view of a therapeutic component according to exemplary embodiments of the present disclosure.
Figure 29C:
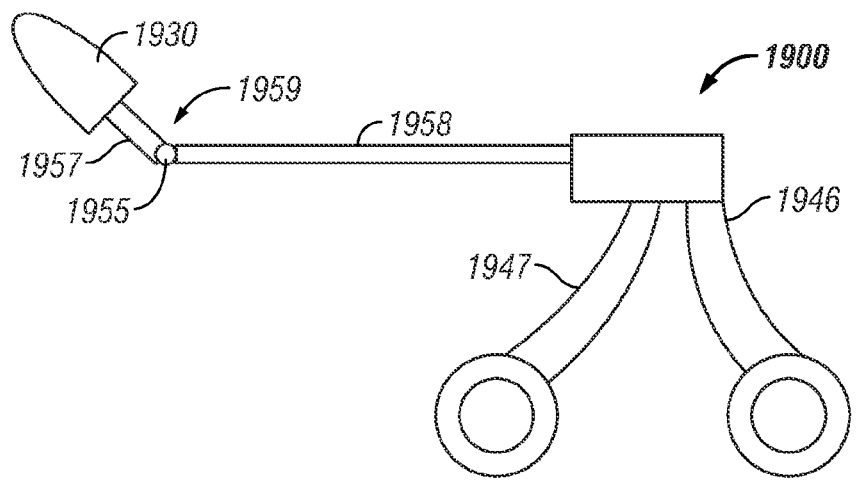
FIG. 29C illustrates a side view of a therapeutic component and an insertion device according to exemplary embodiments of the present disclosure.
Figure 29D:
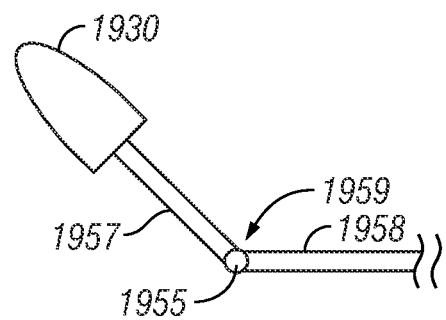
FIG. 29D illustrates a side view of the therapeutic component of FIG. 29C.

In embodiment shown in FIGS. 29C and 29D, an insertion device comprises a handle portion 1946 and a therapeutic component 1930 coupled to an articulating and/or extending shaft 1959. Shaft 1959 comprises a fixed portion 1958 and an extending portion 1957 that is configured to articulate around a pivot point 1955. As shown in FIG. 29C, shaft 1959 is articulated, but not expanded or extended. In this embodiment, handle portion 1946 comprises an actuator 1947 configured to extend and/or articulate extending portion 1957. As shown in FIG. 29D, extending portion 1957 of shaft 1959 is extended. Therapeutic components 1930 of incrementally increasing diameters can be used to dilate a sinus/opening as described in the embodiment of FIGS. 29A-29B. However, the embodiment shown in FIGS. 29C-29D may allow for greater access to certain sinuses or openings.

Guide Wire Embodiments

Figure 30A:
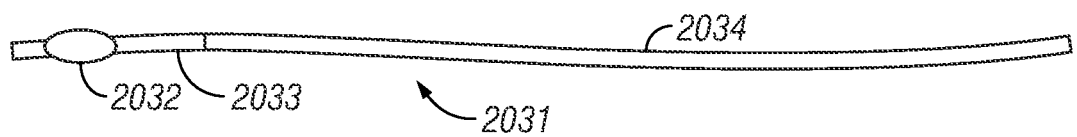
FIG. 30A illustrates a side view of a guide wire according to exemplary embodiments of the present disclosure.
Figure 30B:
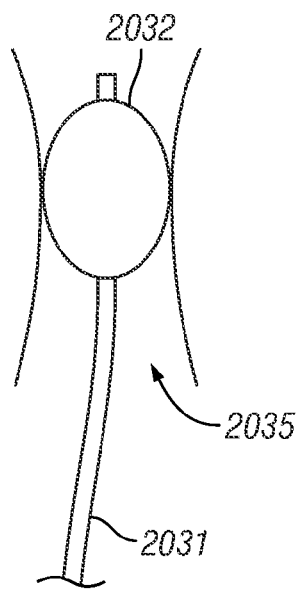
FIG. 30B illustrates a side view of the therapeutic component of FIG. 30A.

Referring now to FIGS. 30A-30B, a specific embodiment comprises a therapeutic component 2030 configured to be used with a guide wire 2031. In this embodiment, guide wire 2031 comprises an expandable anchor member 2032. In the embodiment shown, guide wire comprises a semi-rigid portion 2033 proximal to anchor member 2032 and a flexible portion 2034. Semi-rigid portion 2033 can be shaped to place anchor member 2032 in a desired location. As shown in FIG. 61, anchor member 2032 is shown in a contracted position, while in FIG. 62 anchor member 2032 is shown in an expanded position located in a sinus 2035.

Figure 30C:
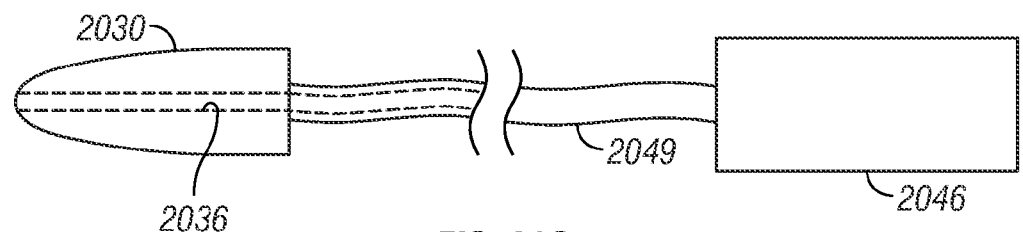
FIG. 30C illustrates a side view of a therapeutic component and an insertion device according to exemplary embodiments of the present disclosure.

Referring now to FIG. 30C, a therapeutic component 2030 is coupled to a shaft member 2049 and a handle member 2046. Therapeutic component 2030 (and the portion of shaft member 2049 proximal to therapeutic component 2030) comprise an internal lumen 2036 configured to receive guide wire 2031. During operation, guide wire therapeutic component 2030 is located so that guide wire 2031 is directed within internal lumen 2036. Anchor member 2032 anchors the distal end of guide wire 2031 in the desired sinus 2035 or other opening. As therapeutic component 2030 is advanced along guide wire 2031, therapeutic component 2030 dilates the sinus 2035 in the manner described in the previously-described embodiments utilizing therapeutic component 1930. In this embodiment, larger therapeutic components 2030 may be sequentially advanced into and out of the sinus 203.

Cable/Wire Control Embodiments

Figure 31A:
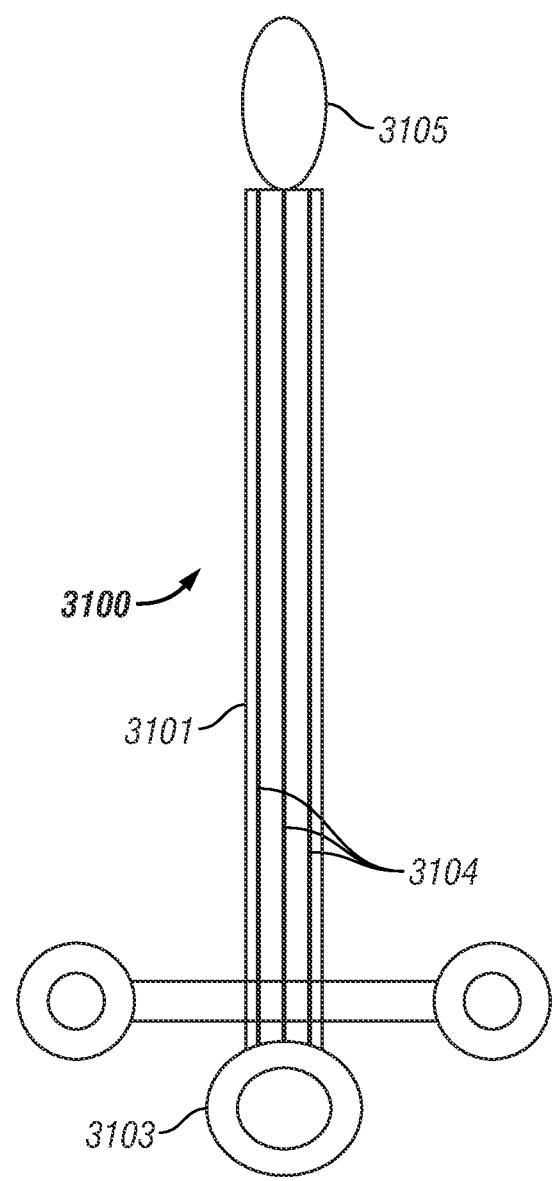
FIGS. 31A-31B illustrate side views of a therapeutic component and an insertion device according to exemplary embodiments of the present disclosure.
Figure 31B:
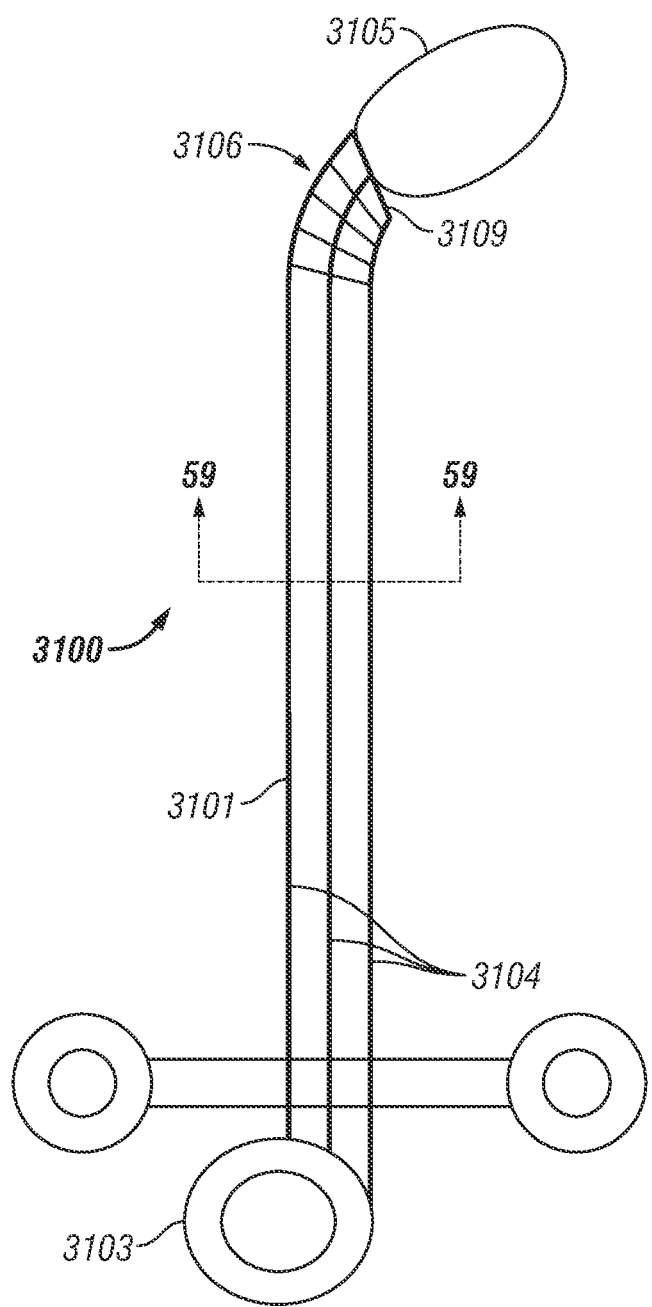
Figure 31C:
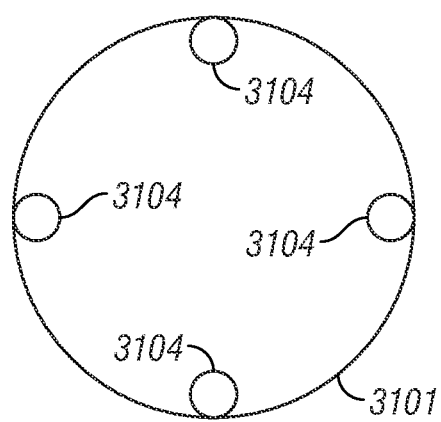
FIG. 31C illustrate a cross-section view of the embodiment of FIGS. 31A-31B.

Referring now to FIGS. 31A-31C, an alternate embodiment of an insertion device 3100 comprises a central tubular member 3101 with a plurality of flexible actuation members 3104 (e.g., cables, wires, rods, or small tubes) coupled to an actuator 3103 and a distal end 3109 of central tubular member 3101. A therapeutic component 3105 is attached to the distal end 3109 of central tubular member 3101. As actuator 3103 is manipulated (e.g. to a position similar to that shown in FIG. 31B), the effective length of actuation members 3104 are altered so that distal end 3109 and therapeutic component 3105 are deflected. For example, the point where an actuation member 3104 couples to actuator 3103 may be shifted in a direction away from distal end 3109. In certain embodiments, central tubular member 3101 may comprise a plurality of articulation points 3106 (e.g., slits or grooves formed central tubular member 3101) so that distal end 3109 can be deflected when actuator 3103 is manipulated. A cross-section of central tubular member 3101 and actuation members 3104 is shown in FIG. 31C.

The various exemplary expansion and/or therapeutic components described above may also comprise additional features. For example, the expansion/therapeutic components may be configured to elute drugs, including, e.g., steroids, anti-inflammatory drugs, etc. The expansion/therapeutic components may comprise a bioabsorbable material, e.g. poly-L-lactide (PLLA), polyhydroxyalknoates (PHA), methyl methacrylate (MMA), etc. In certain embodiments, the expansion/therapeutic components may be a metal (e.g., stainless steel, cobalt chrome [CoCR], Nitinol, etc.).

Additional Methods of Use

Certain embodiments also comprise specific methods of using the therapeutic components described herein. For example, certain methods may comprise preparing a target sinus, including if needed, performing surgical debridement as required to obtain adequate access and visualization. The methods may also comprise coupling a therapeutic component to a pressuring device and to a first insertion device. The methods may further comprise inserting the therapeutic component into a first nasal passageway and a first sinus, using articulation of the first delivery device and visualization via an endoscope to locate the therapeutic component if needed. In certain embodiments, the therapeutic component is positioned with the aid an image guidance navigation system via a location sensor coupled to the insertion device. In such embodiments, the articulating insertion device can be configured to provide rigidity at pre-set positions to provide the accuracy needed for navigation technology. In certain embodiments, the therapeutic component may be placed in the desired location without the use of a cannula or guide wire.

Additionally, exemplary methods may comprise expanding and contracting the therapeutic component to dilate the target sinus, for example by inflating a dilation balloon. The method may further comprise observing the first sinus with the endoscope, and expanding and contracting the therapeutic component again as needed in order to obtain the desired expansion of the first sinus, and/or to insert the therapeutic component into a second sinus and expanding and contracting the therapeutic component to obtain the desired expansion of a second sinus. Certain embodiments may also comprise removing the therapeutic component from the delivery device and coupling the therapeutic component to a second delivery device; and repeating the previously-described actions with a second sinus.

Specific embodiments may also comprise placing a therapeutic component into a target sinus structure using an insertion device and then removing the insertion device from the sinus while leaving the therapeutic component in the sinus. The therapeutic component may then be expanded (e.g, inflated) using a pressurizing member. The therapeutic component may then be returned to its non-expanded state (e.g. by venting the pressurizing member) and retrieved from the sinus using a tether or a conduit between the pressurizing member and the therapeutic component. One potential advantage of such an embodiment is that a single operator may perform the expansion/dilation procedure. A first operator does not have to hold the insertion device while a second operator expands the therapeutic component.

In certain embodiments, a method of use comprises coupling a therapeutic component to a flexible endoscope. This arrangement can allow the endoscope image to be used for visualization and placement of the therapeutic component without surgical debridement. In addition a light on the endoscope may be utilized to transilluminate the sinus (allowing the user to see the light externally) to assist in correct placement of the therapeutic component. In certain embodiments, a therapeutic component may be placed without external visualization or transillumination. In other methods, the therapeutic component and endoscope may be coupled to an articulating instrument to assist in delivery and positioning of the therapeutic component using visualization from the endoscope.

Certain methods of use may also include the placement of an expandable stent in a sinus structure. For example, a user may initially debride or dilate a target sinus as needed and then insert a stent and therapeutic component into a sinus. The therapeutic component may be expanded (e.g. via a pressurizing member) to expand and deploy the stent in the desired location within the sinus. In certain embodiments, an endoscope may be used to verify adequate deployment of the stent. If needed, the stent may be further expanded with a larger therapeutic component. In certain embodiments, the stent may be self-expanding and may be expanded when a retention sleeve is removed after placement within the sinus.

In alternate embodiments, the method of use may additionally include delivery of a therapeutic agent such as an antibiotic spray, powder or solution into the paranasal sinus. This agent delivery may be done before, during, or after performing a therapy on the sinus passageway. For example, a user may deliver a solution through a secondary lumen of the therapeutic component into the frontal sinus during balloon dilation of the frontal sinus recess. In this manner, the balloon both dilates the passage and blocks drainage of the solution, such that the solution remains in the frontal sinus for a period of time while the balloon is inflated.

High Frequency Pressure Wave Embodiments

Certain embodiments may comprise a method of providing therapy to a paranasal sinus outflow tract by emitting a high frequency pressure wave from a therapeutic component to expand a paranasal sinus outflow tract. In particular embodiments, the high frequency pressure wave may be generated by a piezoelectric transducer. In certain embodiments, the pressure wave may be between 50 kHz to 26.5 MHz. In particular embodiments, the pressure wave may be between 30 kHz to 46.5 MHz, or between 40 kHz to 36.5 MHz, or between 60 kHz to 16.5 MHz.

In specific embodiments, the method comprises inserting a therapeutic component into a paranasal sinus outflow tract without the use of a guide wire, cannula or guide sheath. The method may also comprise emitting a high frequency pressure wave from the therapeutic component and enlarging the paranasal sinus outflow tract via the high frequency pressure wave.

In specific embodiments, the high frequency pressure wave comprises a radio frequency pressure wave. In particular embodiments, the high frequency pressure wave comprises an ultrasonic frequency pressure wave. In certain embodiments, inserting the therapeutic component into the paranasal sinus outflow tract comprises: providing a shaft with a distal end and an articulating portion; coupling the therapeutic component to the shaft; and inserting the distal end of the shaft into the paranasal sinus outflow tract.

Certain embodiments may also comprise: moving the articulating portion of the shaft from a first position to a second position; and engaging the distal end of the shaft with tissue proximal to the paranasal sinus outflow tract, where the articulating portion of the shaft remains in the second position when the distal end of the shaft engages the tissue proximal to the paranasal sinus outflow tract. In specific embodiments, the tissue may comprise scar or granulation tissue.

Particular embodiments may also comprise tracking the location of the distal end of the shaft with a location sensor. Specific embodiments may also comprise delivering a therapeutic fluid to the paranasal sinus outflow tract. In certain embodiments, the paranasal sinus outflow tract comprises a frontal sinus.

Certain embodiments may also comprise a method of dilating a paranasal sinus outflow tract, the method comprising: inserting a therapeutic component into the paranasal sinus outflow tract, where the therapeutic component is coupled to a shaft with an articulating portion; emitting a high frequency pressure wave from the therapeutic component and enlarging the paranasal sinus outflow tract; and withdrawing the therapeutic component from the paranasal sinus outflow tract.

In specific embodiments, the paranasal sinus outflow tract is enlarged by destructing tissue and removing tissue in the paranasal sinus outflow tract. In particular embodiments, the high frequency pressure wave comprises a radio frequency pressure wave or an ultrasonic frequency pressure wave. In certain embodiments, the paranasal sinus outflow tract comprises granulation or scar tissue. In specific embodiments, the shaft comprises a proximal end and a distal end, and the therapeutic component is located between the articulating portion and the distal end.

In certain embodiments, inserting the therapeutic component into the paranasal sinus outflow tract comprises manipulating a positioning member configured to move the articulating portion of the shaft. In specific embodiments, the articulating portion is configured to retain its shape when an external force is applied to the distal end. In particular embodiments, the external force may be a radial force of approximately 0.5 pounds or less. In certain embodiments, the external force may be an force of approximately 0.5 pounds or less.

In particular embodiments, the shaft may be coupled to an insertion device comprising a positioning member configured to move the articulating portion of the shaft. In specific embodiments, the insertion device may comprise a locking member configured to lock the positioning member into a desired position. In certain embodiments, inserting the therapeutic component into the paranasal sinus may not require the use of a guide wire or cannula.

In particular embodiments, the paranasal sinus outflow tract may comprise a maxillary sinus, a frontal sinus, or a sphenoid sinus.

In certain embodiments, the therapeutic component may be an inflatable balloon or a mechanical dilator. Certain embodiments may comprise tracking the location of the therapeutic component with a location sensor.

Particular embodiments may comprise: providing a stent disposed on the therapeutic component prior to inserting the therapeutic component into the paranasal sinus outflow tract; expanding the stent while expanding the therapeutic component; and withdrawing the therapeutic component from the stent so that the stent remains in the paranasal sinus outflow tract to maintain the dilated state for a period of time.

In certain embodiments, the stent may be bioabsorbable, and in particular embodiments, the stent may be configured to elude a therapeutic agent. In specific embodiments, the therapeutic agent is selected from one or more of the following: antibiotics, anti-inflammatory agents, corticosteroids, vasoconstrictors, vasodilators, anti-allergy agents, antihistamines, cromolyn sodium, decongestants, and asthma treatments.

In certain embodiments, the stent may comprise a bioabsorbable material selected from the group consisting of: polymers, polyesters, polyanhydrides, proteins, rubber, polysaccharides, xenografts and allografts.

Particular embodiments may comprises a method of providing therapy to a paranasal sinus outflow tract, where the method comprises: inserting a therapeutic component into a paranasal sinus outflow tract, where the therapeutic component is inserted into the paranasal sinus outflow tract without the use of a guide wire, cannula or guide sheath; emitting an ultrasonic frequency from the therapeutic component; and enlarging the paranasal sinus outflow tract via the ultrasonic frequency.

Cryogenic Temperature Embodiments

Certain embodiments may also comprise method of providing therapy to a paranasal sinus outflow tract, where the method comprises: inserting a therapeutic component into the paranasal sinus outflow tract, where the therapeutic component is inserted into the paranasal sinus outflow tract without the use of a guide wire, cannula or guide sheath; and exposing tissue in the paranasal sinus outflow tract to a cryogenic temperature. In specific embodiments, the tissue in the paranasal sinus outflow tract may shrink after exposure to the cryogenic temperature. In certain embodiments, the tissue in the paranasal sinus outflow tract may be damaged after exposure to the cryogenic temperature.

Certain embodiments may comprise a method of dilating a paranasal sinus outflow tract, where the method comprises: inserting a therapeutic component into the paranasal sinus outflow tract, where the therapeutic component is coupled to a shaft with an articulating portion; emitting a cryogenic temperature from the therapeutic component; and withdrawing the therapeutic component from the paranasal sinus outflow tract. In certain embodiments, the tissue in the paranasal sinus outflow tract may shrink after the therapeutic component emits a cryogenic temperature cryogenic temperature. In particular embodiments, the tissue in the paranasal sinus outflow tract may be damaged after the therapeutic component emits a cryogenic temperature cryogenic temperature.

It is understood that exemplary embodiments include systems and devices configured to perform the methods described herein.

Equivalents And Scope

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a", "an", and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that embodiments of the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, embodiments of the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

REFERENCES

The entire disclosures of the following references are incorporated by reference herein:
U.S. Pat. No. 2,525,183
U.S. Pat. No. 4,733,665
U.S. Pat. No. 4,740,207
U.S. Pat. No. 4,877,030;
U.S. Pat. No. 4,954,126
U.S. Pat. No. 5,007,926;
U.S. Pat. No. 5,059,211
U.S. Pat. No. 5,192,307
U.S. Pat. No. 5,421,955
U.S. Pat. No. 5,441,515
U.S. Pat. No. 5,443,500
U.S. Pat. No. 5,549,662
U.S. Pat. No. 5,618,299
U.S. Pat. No. 5,643,314
U.S. Pat. No. 5,649,977
U.S. Pat. No. 5,733,328
U.S. Pat. No. 5,735,872
U.S. Pat. No. 7,462,175
U.S. Pat. No. 7,500,971
U.S. Pat. No. 7,553,275
U.S. Pat. No. 7,670,284
U.S. Pat. Pub. No. 2004/0064150
U.S. Pat. Pub. No. 2009/0125046
U.S. Pat. Pub. No. 2008/0215083
U.S. Pat. Pub. No. 2008/0208242
U.S. Pat. Pub. No. 2008/0215082
U.S. Pat. Pub. No. 2008/0208243
U.S. Pat. Pub. No. 2006/0149310
U.S. Pat. Pub. No. 2006/0136041
Göttmann, D., Strohm, M., Strecker, E. P., Karlsruhe, D. E., "Balloon dilatation of Recurrent Ostial Oclusion of the Frontal Sinus", Abstract No. B-0453, European Congress of Radiology (2001)
Strohm, M., Göttmann, D., "Treatment of Stenoses of Upper Air Routes by Balloon Dilation", Proceeding of the 83$^{rd}$ Annual Convention of the Association of West German ENT Physicians (1999).
Balcon et al., "Recommendations on Stent Manufacture, Implantation and Utilization," European Heart Journal (1997), vol. 18, pages 1536-1547.
"The Stenter's Notebook," Physician's Press (1998), Birmingham, Mich.

What is claimed is:

1. A method of providing therapy to a paranasal sinus outflow tract, the method comprising:
coupling a therapeutic component to a shaft, the shaft having a distal end and an articulating portion; the therapeutic component spaced distally from the articulating portion;
inserting the therapeutic component into a paranasal sinus outflow tract, wherein the therapeutic component is inserted into the paranasal sinus outflow tract without the use of a guide wire, cannula or guide sheath;
emitting a high frequency pressure wave from the therapeutic component so as to destroy at least a portion of the paranasal sinus outflow tract via the high frequency pressure wave.

2. The method of claim 1 wherein the high frequency pressure wave is between 24 kHz to 27 kHz.

3. The method of claim 1 wherein the high frequency pressure wave comprises a radio frequency pressure wave.

4. The method of claim 1 wherein the high frequency pressure wave comprises an ultrasonic frequency pressure wave.

5. The method of claim 1 further comprising:
moving the articulating portion of the shaft from a first position to a second position;
engaging the distal end of the shaft with tissue proximal to the paranasal sinus outflow tract, wherein the articulating portion of the shaft remains in the second position when the distal end of the shaft engages the tissue proximal to the paranasal sinus outflow tract.

6. The method of claim 5 wherein the tissue comprises scar or granulation tissue.

7. The method of claim 5 further comprising tracking the location of the distal end of the shaft with a location sensor.

8. The method of claim 1 further comprising delivering a therapeutic fluid to the paranasal sinus outflow tract.

9. The method of claim 1 wherein the paranasal sinus outflow tract comprises a frontal sinus.

10. The method of claim 1 wherein the high frequency pressure wave destroys at least a portion of the sinus outflow tract so as to enlarge the sinus outflow tract.

11. The method of claim 10 the sinus outflow tract is enlarged by the high frequency pressure wave so as to restore normal mucus drainage through the tract.

12. A method of providing therapy to a paranasal sinus outflow tract, the method consisting:
- coupling a therapeutic component to a shaft, the shaft having a distal tip and an articulating portion spaced proximally from the distal tip, the therapeutic component disposed between the articulating portion and the distal tip;
- inserting the therapeutic component into a paranasal sinus outflow tract, wherein the therapeutic component is inserted into the paranasal sinus outflow tract without the use of a guide wire, cannula or guide sheath;
- emitting a high frequency pressure wave from the therapeutic component, the pressure wave operable to destroy a portion of the paranasal sinus outflow tract via the high frequency pressure wave;
- halting the step of emitting; and
- withdrawing the therapeutic component from the paranasal sinus outflow tract.

13. The method of claim 12 wherein the sinus tract comprises scar and granular tissue and wherein the step of emitting a high frequency pressure wave so as to destroy a portion of the paranasal sinus outflow tract destroys scar and granular tissue.

14. The method of claim 12 wherein the step of emitting a high frequency pressure wave so as to destroy a portion of the paranasal sinus outflow tract enlarges the sinus outflow tract, the enlarged outflow tract configured to restore normal mucus drainage through the tract.

* * * * *